(12) United States Patent
St-Arnaud

(10) Patent No.: US 7,414,109 B2
(45) Date of Patent: Aug. 19, 2008

(54) FIAT NUCLEIC ACIDS AND PROTEINS AND USES THEREOF

(75) Inventor: René St-Arnaud, St-Laurent (CA)

(73) Assignee: Shriners Hospital for Children, Tampa, FL (US)

( * ) Notice: Subject to any disclaimer, the term of this patent is extended or adjusted under 35 U.S.C. 154(b) by 0 days.

(21) Appl. No.: 11/118,809

(22) Filed: Apr. 29, 2005

(65) Prior Publication Data

US 2005/0278796 A1 Dec. 15, 2005

Related U.S. Application Data

(60) Provisional application No. 60/566,698, filed on Apr. 29, 2004.

(51) Int. Cl.
*C07K 14/00* (2006.01)
*C07H 21/02* (2006.01)
(52) U.S. Cl. .................... 530/350; 536/23.1
(58) Field of Classification Search ............... 530/350; 536/23.1
See application file for complete search history.

(56) References Cited

U.S. PATENT DOCUMENTS 5,948,643 A * 9/1999 Rubinfeld et al. .......... 435/69.1
2002/0123619 A1* 9/2002 Benson et al. ............. 536/23.1

FOREIGN PATENT DOCUMENTS

EP 1 07 4617 A2 * 2/2001

OTHER PUBLICATIONS

Obazaki et al. 2002; Analysis of the mouse transciptome based on functional annotation of 60,770 full-length cDNAs. Nature. 420:563-573.*
Boyden et al., "High bone density due to a mutation in LDL-receptor-related protein 5," N. Engl. J. Med. 346(20):1513-21, May 16, 2002.
Butscher et al., "Coordinate transactivation of the interleukin-2 CD28 response element by c-Rel and ATF-1/CREB2," J. Biol. Chem. 2;273(1):552-60, Jan. 2, 1998.
Chevray et al., "Protein interaction cloning in yeast: identification of mammalian proteins that react with the leucine zipper of Jun," Proc. Natl. Acad. Sci. USA 89:5789-93, 1992.
Dacquin et al., "Mouse alpha1(I)-collagen promoter is the best known promoter to drive efficient Cre recombinase expression in osteoblast," Dev. Dyn. 224(2):245-51, Jun. 2002.
Ducy et al., "Two distinct osteoblast-specific cis-acting elements control expression of a mouse osteocalcin gene," Mol. Cell Biol. 15(4):1858-69, Apr. 1995.
Ecarot-Charrier et al., "Osteoblasts isolated from mouse calvaria initiate matrix mineralization in culture," J. Cell Biol. 97(3):639-43, Mar. 1983.
Fawcett et al., "Complexes containing activating transcription factor (ATF)/cAMP-responsive-element-binding protein (CREB) interact with the CCAAT/enhancer-binding protein (C/EBP)-ATF composite site to regulate Gadd153 expression during the stress response," Biochem. J. 339 (Pt 1):135-41, Apr. 1, 1999.

Franceschi et al., "Relationship between collagen synthesis and expression of the osteoblast phenotype in MC3T3-E1 cells," J. Bone Miner. Res. 7(2):235-46, Feb. 1992.
Gachon et al., "CREB-2, a cellular CRE-dependent transcription repressor, functions in association with Tax as an activator of the human T-cell leukemia virus type 1 promoter," J Virol. 72(10):8332-7, Oct. 1998.
Gong et al., "LDL receptor-related protein 5 (LRP5) affects bone accrual and eye development," Cell 107(4):513-23, Nov. 16, 2001.
Hai et al., "Cross-family dimerization of transcription factors Fos/Jun and ATF/CREB alters DNA binding specificity," Proc. Natl. Acad. Sci. U S A 88(9):3720-4, May 1, 1991.
Hai et al., "The molecular biology and nomenclature of the activating transcription factor/cAMP responsive element binding family of transcription factors: activating transcription factor proteins and homeostasis," Gene 273(1):1-11, Jul. 15, 2001.
Hai et al., "Transcription factor ATF cDNA clones: an extensive family of leucine zipper proteins able to selectively form DNA-binding heterodimers," Genes Dev. 3(12B):2083-90, Dec. 1989, Erratum in: Genes Dev 4(4):682, Apr. 1990.
Harding et al.,"An integrated stress response regulates amino acid metabolism and resistance to oxidative stress," Mol. Cell 11(3):619-33, Mar. 2003.
Hettmann et al., "Microphthalmia due to p53-mediated apoptosis of anterior lens epithelial cells in mice lacking the CREB-2 transcription factor," Dev. Biol. 222(1):110-23, Jun. 1, 2000.
Jungling et al., "Differential regulation of chromogranin B and synapsin I gene promoter activity by cAMP and cAMP-dependent protein kinase," Eur. J. Biochem. 226(3):925-35, Dec. 15, 1994.
Karpinski et al., "Molecular cloning of human CREB-2: an ATF/CREB transcription factor that can negatively regulate transcription from the cAMP response element," Proc. Natl. Acad. Sci. U S A 89(11):4820-4, Jun. 1, 1992.
Kawai et al., "ZIP kinase, a novel serine/threonine kinase which mediates apoptosis," Mol. Cell Biol. 18(3):1642-51, Mar. 1998.
Lassot et al., "ATF4 degradation relies on a phosphorylation-dependent interaction with the SCF(betaTrCP) ubiquitin ligase," Mol Cell Biol. 21(6):2192-202, Mar. 2001.
Lepourcelet et al., "Small-molecule antagonists of the oncogenic Tcf/β-catenin protein complex," Cancer Cell, 5:91-102, Jan. 2004.
Liang and Hai, "Characterization of human activating transcription factor 4, a transcriptional activator that interacts with multiple domains of cAMP-responsive element-binding protein(CREB)-binding protein," J. Biol. Chem. 272(38):24088-95, Sep. 19, 1997.
Lim et al., "Latency-associated nuclear antigen of Kaposi's sarcoma-associated herpesvirus (human herpesvirus-8) binds ATF4/CREB2 and inhibits its transcriptional activation activity,"J. Gen. Virol. 81(Pt 11):2645-52, Nov. 2000.
Majeska et al., "Parathyroid hormone-responsive clonal cell lines from rat osteosarcoma," Endocrinology 107(5):1494-503, Nov. 1980.

(Continued)

*Primary Examiner*—Karen Cochrane Carlson
(74) *Attorney, Agent, or Firm*—Fish & Richardson P.C.

(57) ABSTRACT

The invention provides FIAT nucleic acids and proteins, and methods of using such nucleic acids and proteins.

15 Claims, 23 Drawing Sheets

OTHER PUBLICATIONS

Masuoka et al., "Targeted disruption of the activating transcription factor 4 gene results in severe fetal anemia in mice," Blood 99(3):736-45, Feb. 1, 2002.

Mielnicki et al., "Isolation and nucleotide sequence of a murine cDNA homologous to human activating transcription factor 4," Nucleic Acids Res. 19(22):6332, Nov. 25, 1991.

Mielnicki et al., "Mutated Atf4 suppresses c-Ha-ras oncogene transcript levels and cellular transformation in NIH3T3 fibroblasts," Biochem. Biophys. Res. Commun. 228(2):586-95, Nov. 12, 1996.

Moreau et al., "Bone-specific expression of the alpha chain of the nascent polypeptide-associated complex, a coactivator potentiating c-Jun-mediated transcription," Mol. Cell Biol. 18(3):1312-21, Mar. 1998.

Nogami et al., "Identification and characterization of taxilin isoforms," Biochem. Biophys. Res. Comm. 319: 936-43, 2004.

Pati et al., "Human Cdc34 and Rad6B ubiquitin-conjugating enzymes target repressors of cyclic AMP-induced transcription for proteolysis," Mol. Cell Biol. 19(7):5001-13, Jul. 1999.

Persengiev et al.;, "Inhibition of apoptosis by ATFx: a novel role for a member of the ATF/CREB family of mammalian bZIP transcription factors," Genes Dev. 16(14):1806-14, Jul. 15, 2002.

Porter et al., "Effect of dexamethasone withdrawal on osteoblastic differentiation of bone marrow stromal cells," J. Cell Biochem. 90(1):13-22, Sep. 1, 2003.

Quarles et al., "Distinct proliferative and differentiated stages of murine MC3T3-E1 cells in culture: an in vitro model of osteoblast development," J. Bone Miner. Res. 7(6):683-92, Jun. 1992.

Reddy et al., "Functional interaction of the HTLV-1 transactivator Tax with activating transcription factor-4 (ATF4)," Oncogene 14(23):2785-92, Jun. 12, 1997.

Rossert et al., "Separate cis-acting DNA elements of the mouse pro-alpha 1(I) collagen promoter direct expression of reporter genes to different type I collagen-producing cells in transgenic mice," J. Cell Biol. 129(5):1421-32, Jun. 1995.

Schinke et al., "Characterization of Osf1, an osteoblast-specific transcription factor binding to a critical cis-acting element in the mouse Osteocalcin promoters," J. Biol. Chem. 274(42):30182-9, Oct. 15, 1999.

Shimizu et al., "Activation of the rat cyclin A promoter by AFT2 and Jun family members and its suppression by ATF4," Exp. Cell Res. 239(1):93-103, Feb. 25, 1998.

Sudo et al., "In vitro differentiation and calcification in a new clonal osteogenic cell line derived from newborn mouse calvaria," J Cell Biol. 96(1):191-8, Jan. 1983.

Talukder et al., "Heregulin induces expression, DNA binding activity, and transactivating functions of basic leucine zipper activating transcription factor 4," Cancer Res. 60(2):276-81, Jan. 15, 2000.

Tanaka et al., "Targeted disruption of ATF4 discloses its essential role in the formation of eye lens fibres," Genes Cells 3(12):801-10, Dec. 1998.

Tsujimoto et al., "Isolation of cDNAs for DNA-binding proteins which specifically bind to a tax-responsive enhancer element in the long terminal repeat of human T-cell leukemia virus type I," J. Virol. 65(3):1420-6, Mar. 1991.

Vallejo et al., "C/ATF, a member of the activating transcription factor family of DNA-binding proteins, dimerizes with CAAT/enhancer-binding proteins and directs their binding to cAMP response elements," Proc. Natl. Acad. Sci. U S A 90(10):4679-83, May 15, 1993.

Wiedmann et al., "A protein complex required for signal-sequence-specific sorting and translocation," Nature 370(6489):434-40, Aug. 11, 1994.

Yang et al., "ATF4 is a substrate of RSK2 and an essential regulator of osteoblast biology; implication for Coffin-Lowry Syndrome," Cell 117(3):387-98, Apr. 10, 2004.

Yang et al., "Effects of dexamethasone on proliferation, differentiation and apoptosis of adult human osteoblasts in vitro," Chin. Med. J. (Engl). 116(9):1357-60, Sep. 2003.

Yotov et al., "The alpha chain of the nascent polypeptide-associated complex functions as a transcriptional coactivator," Mol. Cell Biol. 18(3):1303-11, Mar. 1998.

Yoshida et al., "Interaction of the taxilin family with the nascent polypeptide-associated complex that is involved in the transcriptional and translational processes," *Genes to Cells* 10:465-76, 2005.

* cited by examiner

FIG. 1A

```
GAGATTCTGTGCCCCTTGTCGGGCCGCTTGTTGGCTGCTGCCGTCACCTCATGGCGACGCGGGTAGAGAGGAGGCAGCGCGGGGAAGAGGCGGCGGCCG
AAGAGGCGACTGAGGCCGGACGGCGACGGCCAGCGCGGCGACGCAGAAGTTTGAAATTGCACAAGAAGCTGAATTGTGGGCTAGGGT
GAAAGCAGATATGTTGTACTCTCAATCAAATGATATTCTTCAACATCAAGGCTCAAATTGTGGTGCACAAGTAACAAGCATTCATTGGAAGAGGAT
GAAGGCAGTGACTTTATAAACAGAGAACAGGAATTTGGTGAGCCCAGTACTGCACGCATATGTGAGCAACAAGAGAGTTTATTACTGCAAGCCTAAACACCCTTTC
ATCCCCCTGATGGTCAGCAGAAGCTCAGAGTGCAACAGGAGAATTCAGAGTGCAACAGGAAAATATGCTGAACATGAAGCAAAATGAAGATCCTGCAAGAAG
AACCCCAGAGAGAGAAGCTGGCAGCTCTCTGTAAGAAATATGCTGAACATAGCAAGCTATCTTGGCAGAAGCTAGAATCTCTTTGCAGAGAACTTCAGC
CAAGCCAGATTGTGAAAGAGAAAGTTCACTTGCAGAGTGAACATGCAGCAGTGAACACGACGTAAAGAAGCAACTGCACATTCCAGATTACCTTAGATGA
GTCACAATAAGACGTTAAAGGAGCAGCATGAGAAAATATGACACTCCGACAGGAAGAAGACATTGAGCTGGGGGAGCCAAACTGCAACACAACTGATAAAG
AATTCAAGCCCAGCTGGAGCAGCACATTGATAAGGTGTTCAAACTGAAGGAACTGCAAGTACAAGGTAAGAAGCTCAACAAATGAACGACACAGAGAAGTACAACT
AAGCTGATGAAACATCAGAGAGAGAGAGAGTTTTATTAAAAGAAATTCCAGACTACTAAGTTTGAAGAATTCCAGACTTACCTTTACAACCTTCAGACAGGAAATGGAA
AAACAGCAGCTTTCTCTTATATGATAAGTTTGAAGAATTCCAGACTACTAAGTTTGAAGAATTCCAGACTTACCTTTACAACCTTCAGACAGGAAATGGAA
AAGATGACAAGAAATTAAAGAAGAGTACAAGGCAGTGCTGCAGGAGCATCAAAGGAAAATAAAACTGGAAGCTGTGCAGGAATGAAGACACTGAGTCAATGA
GAAGTGGAAGTTCCTGATAAAGAGTACAAGGCAGTTCCTCCGCCCCATGCAGGTGGGGCAGGGCACATCAAAGCTGTGAAGAAGCGCTGTGCAAAGCCCCGT
GATTCTCACAAGGAGCTGAACACTTCCGGTCCTCGCCCCAGCTCGGTCAGGGATGAGGTGTGATCAATCTGTATTTGTGTATGGTACAGGCTGCTTAGCAGT
CAGAGCGCTCTGCTCCGGCCATCCGAGTCGGTTGACAATGAGGTGTGATCACTGTATTTTCTTAGAACTCGACTATGGTACAGGCTGCTTAGCAGT
AACTATTGGTTTGTGTGGTGAAAATTTAATCTATAATTATTCCTCAGCTGTGTTGCACATGCTGTTCTCCGTTCCTCCCTGAATGCCATGCTGTGTTCTTCTT
TTTGAATATGTTAATCTATAATTATTCCTCAGCTGTGTTGCACATGCTGTTCTCCGTTCCTCCCTGAATGCCATGCTGTTCTCTGCTGTCCTTTCTCT
CCCTGCTCCTTGCACATTATGACATTATCATCCTAATGAAAATTTCACTGACAGGGCCGACCATTACAAGGGAACTTTGTTCTGACGATGGTTCCTTGATGTGAAAAC
AATATTATTAAAGTCTTAGCACCCCCCCCCATAATATTATTC (SEQ ID NO:1)
```

FIG. 1B

```
MATRVEEAAR   GRGGGAEEAT   EAGRGGRRRS   PRQKFEIGTM   EEAGICGLGV   KADMLCNSQS   NDILQHQGSN
CGGTSNKHSL   EEDEGSDFIT   ENRNLVSPAY   CTQESREEIP   GGEARTDPPD   GQQDSECNRN   KEKTLGKEVL
LLMQALNTLS   TPEEKLAALC   KKYADLLEES   RSVQKQMKIL   QKKQAQIVKE   KVH LQSEHSK   AILARSKLES
LCRELQRHNK   TI KEENMQQA   REEEERRKEA   TAHFQITLDE   IQAQLEQHDI   HNAKLRQENI   ELGEKLKKLI
EQYALREEHI   DKVFKRKELQ   QQLVDAKLQQ   TTQLIKEADE   KHQREREFLL   KEATESRHKY   EQMKQQEVQL
KQQLSLYMDK   FEEFQTTMAK   SNELFTTFRQ   EMEKMTKKIK   KLEKETIIWR   TKWENNNKAL   LQMAEEKTVR
DKEYKALQIK   LERLEKLCRA   LQTERNELNE   KVEVLKEQVS   IKAAIKAANR   DLATPVMQPC   TALDSHKELN
TSSKRALGAH   LEAEPKSQRS   AVQKPPSTGS   APAIESVD  (SEQ ID NO:2)
```

FIG. 1C

```
TGGCCCCTGAGAGGTTCCGTGCCCCTGTCGTCCAGCCGCTTGTTGGCTGCTGCCGTCACCTCATGGCGACTCGGCTTGAGGAGGTAACGCGAGGAAGAGGCG
GCGGTACTGAGGAGGCTAGTGAGGGCGGACGGGGCGGACGGCGACGGCGACGGCGGCCCCCCAGAAGTTTGAAATTGGCACAATGGAAGAAGCTAGAATTTGTGG
TTAGGAGTAAAAGCAGACAGACATGGTATGTAACTCTCAAGCAAATGATATTCTTCAACATCAAGACCCCAGTTGTGGTGGCACGACTAAGAACATTCACTGGA
AGGGGATGAAGGCAGTGACTTTATTACAAGAACAGAAATTTGGTGAGCTCAGTATTCTGTACACAGAGAAAGAAGTTTATTACTGACGAGAAGCTC
GAACAGGTCCCTCCTGATGGCCAGCAAGATTCAGAGTGCCAGCAGAACAAAGAGAAGACCTTAGGAGAAGAGACCATCTCAGAAACAAATGAAGATTCTGCAGAA
CTTTCAACCCCAGAGGAGGAAGCTGGCAGCTCTCTGTAAGAAATATGCTAACACAGCAAGGCCATCTTGGCAAGAAGCAAACTGGAATCTCTTTGCAGGGAACTTC
GAAGCAAGCCCAGATTGTGAAAGAGGAGAAAGTTCACCTTCAGAGTGAACACAGCCAAGCACGTAAAGAAGCACGACGCACACATTTCAGATAACTCTAAAT
AGCGTCATAATAAGACCTTGGAACAACATGCAGCAGGAATATGCACGAGGGAGAACATTGAACTGGAGCAGAACTGCGACAGGAAGTTGAAGAAGCTTATTGAGCAGTA
GAAATCCAAGCTCAGTTGGAACAACATGCCAAATGCGACAACAGCTTGTGGATGCCAAACTTCAGCAACAACACACAGCTGATAAAAG
TGCACTAAGGGAAGAGCATATTGATAAAGTATTCAAACACAAGGAATTGCAACAACAGCTGCAAAAATGAACAATGAACAGCAAGAAGTACAACTA
AAGCTGATGAAAAACATCAGAGAGAGAGTTTATATGGATAAATTTGAAGAATTCCAGACTACTTTGAAGAATTAAGCACTTCTCAGGCAGGAAATGAAAA
AAACAGCAGCTTTCTTTTTAGATAAAATTTAAAACAACTGAAAAAGAAAAATAATAAGCAATCCAGACTACTATGGCAAATGGGAAAACAATAATAAAGCACTTCTGCAGAGAGAAATGAGCTCAACGAGAG
GATCACAAAGAAATTAAAACACTGGAAAAGAAAAGAACAATAATAAAACTGGAAAGCTGTGCAGGGCTCTTCAGACAGAGAAATGAGCTCAACGAGAG
CTGTCCGTGATAAAGAGTACAAGGCTTTCAAATAAACTGAAGCAGCAGATGGGACTTGGTGTCACCTGTGAGAAAAGTGCTGCACAAAAGCCCTCATCTTCAGTTCTCCTGCTCAAG
GTCGAAGTCCTGAAAGACCCTGGAATGCACTTGGAAGTATGATCACTGTATTGAGAACTACTGACTTTGAGAACTACTGGACTTGTGTATACAGGAGGCTGCTTAGCAGTTTGAATAGTTTTTACTCTATA
TTCAAGAAGAACCCTGGGACTGAGTAGGGTGACTAGGTGAAGTATGATCACTGTATTCTGTATTCTTAGAACTACTGGACTTGTGTATACAGGAGGCTGCTTAGCAGTTTGAATAGTTTTTACTCTATA
AGATTTTCTTACTTTTCTACCATATGTTGCACATATCTGTATTTCTGCCTCATTTCCCCGTTGGAGTGCATGCTATAATTAGTGAAAGAAGTAAAATAACCTTAATAACCATTTAATAAAACAAGGCCATTAGAGG
AATTATATATCTCCGATGGTCAGAAACATTTTCATTTGAATTGAGGATAGATGAAGTTTTGTTCATTTGCATTAAGACTCAACAAGCAGGGCTGCTACATGTGTGTAGCTCAGTGCAA
TCATAAAGTAGTCCTAATATGTTCCTCACCATACATTCTGGCTTTGCTTTGTTGACAAGTTTCATCAGCAAAGAACACTAGTTATTTTGTTTCCTAATAGAGAATTTAAATTATAGATCAGATA
GCTCCCCTCCTCCACCATACATTCTGGCTTTGCTTTGTTGACAAGTTTCATCAGCAAAGAACACTAGTTATTTTGTTTCCTAATAGAGAATTTAAATTATAGATCAGATA
GCATTGCCTATCATAAGAGGCTCTGGGTTGAACAACACTGGAACCAGCTTGGAACCAGCTTGGAACACTGTTACATAGTCAAGAGACGCCTAGCTTTCTAGTCTATT
ACATAAGATAACATTTCCAAAGTAAAACACTGAAGTAAAACATAATAAACCAGTATTACAGTCAGAGAGACTGTTGACACTTGTTGATATTTATGGCTCAGCATGCAAATTACTTATACTCCTTAGCACATTTATT
TCTCCGTTTTTGATGCTATCACTTCACTTAAAGTTCTAGTAAAGTCAAATAATTGAAAAATGGCCAAAGCCAGAAAACAGTCCCTGTAGATGTTATTTCTAAACTAATCAAGGGGTCAAAA
GTAAAGTAAATTTATTAAAGTTCAAATAATTGAAAAATGGCCAAAGCCAGAAAACAGTCCCTGTAGATGTTATTTCTAAACTAATCAAGGGGTCAAAA
TTTATGGTCAAATCTAGGTTCAAATAATTGAAGTCAGAAACAACAAAAAAACCCCTTCAGTAGCCTTCAAATCAAATCTGGACTTTTTCCCCATGAACGTGTCAGAAATA
GTAAAGAAGTGAAAAAAGTGAACAACACAAAAAAACCCCTTCAGTAGCCTTCTTATCAAATCTGATTATTGATAAGCACTGTGTAGCCTGCCACATGTTTGTGGTAC
TTGAAATTACTACTAATGATTACATTCACAGTCTGCTGATACAGCTCTTAACATTGATTAAGCAATAACAGTCCCCTGCCCCTGTAGACTACAGTCATTTCAGCTAGA
TTGTCCTGTGTGAATATTGCATATTTCAAGGCTTTATAAGCAATGCATTAACAGTCCCCTGCCCCCTGTAGACTACAGTCATTCAAGAGATGCCCCTCCCC
TCTTTAGAGACAGATTCGATTATGAAATATGCATATGTTGTGCTTGTGCACGCCGTATTCTAGACACTGTATGCTACTGTGCTGGCCAGA
TCCCCTAAAGTGATCACCTCAGCAGCCCAGTGTTGTGGCTTGTGACTACCATTCTAGACACTGTATGCTACTGTGCTGGCCAGA
AAAGATTTCTATGTTGAATTCACTTCATCCTCAGACTTGGACATATGGTGCACATACATTTCTGGTCTTGAGACCTGTATATTTTAGTGTCAGTAGTAGTATGTATGATCAACTGCCTTTATTACACACCT
GGTATCAGGCCATTTCATCCTCAGACTTGTTGCAGAAAAAAATCTACCTCTTTCAGACTGTAGATGAAATGTGAAAAATGATGCAGATATAGTTT
GGTTATCACAATTCAACTCTCAGGTGTTGCAGAAAAAAATCTACCTCTTTCAGACTGTAGATGAAATAACTGTAAGAGGCAGTCTGTTTGCTTTTGCTTTTCAAAGAACATTTTGTAGAG
GTGCTAAACACACTGCTAAATCGTAAATCTGATTTTATTCTACTCAATTCTGTAGAGATTCTGTAGAGATTAAGTAATATGTATGATGAAATT (SEQ ID NO:3)
ATTTTCACTACCGTAAATCTGATTTTATTCTACTCAATTCTGTAGAGATTAAGTAATATGTATGATGAAATT (SEQ ID NO:3)
```

FIG. 1D

MATRLEEVTRGRGGTEEASEGGRGGRRRSPPPQKFEIGTMEEARICGLGVKADMVCN
SQANDILQHQDPSCGGTTKKHSLEGDEGSDFITKNRNLVSSVFCTQEKREEIPGREA
RTGPPDGQQDSECSRNKEKTLGKEVLLLMQALNTLSTPEEKLAALCKKYADLLEESR
NVQKQMKILQKKQAQIVKEKVHLQSEHSKAILARSKLESLCRELQRHNKTLKEENMQ
QAREEEERRKEATAHFQITLNEIQAQLEQHDIHNAKLRQENIELGEKLKKLIEQYAL
REEHIDKVFKHKELQQQLVDAKLQQTTQLIKEADEKHQREREFLLKEATESRHKYEQ
MKQQEVQLKQQLSLYMDKFEEFQTTMAKSNELFTTFRQEMEKMTKKIKKLEKETIIW
RTKWENNNKALLQMAEEKTVRDKEYKAFQIKLERLEKLCRALQTERNELNEKVEVLK
EQVSIKAADGDLVSPATQPCAVLDSFKETSRRTLGMHLEARAKSVCEKSAAQKPSSS
GSPAQGIESVD (SEQ ID NO:4)

FIG. 2A

```
gtctgcgctgtgcgtgtttccctcctcccgccctcaggtgtccacggccaccatggcgtattaggggcagcagtgcct
gcgcagcattggcctttgcagcggcggcagcaggctctgcagcggcaaccccagcggcttaagccatggc
gcttctcacggcattccagcagcagcgttgctgtaaccgacaagacacacccttcgaattaagcacattcctgattccag
caaagcaccgcaacatgaccgaaatgagcttcctgagcagcgaggtgttggtggggacttgatgtcccccttcgacc
agtcggggtttgggggctgaaagaagctaaggcgggctcctccgaatggctggctgtggatggttgttgaaggagtt
ggtcctccagcgacaaggctaaggcgggctcctccgaatggctggctgtggatggttgttgaaggagttcgactgatgccctgt
gcaaggaggatgcctctctccggagcacagatgccagatgccttgaccacgttggatgacttctgacactctccagaaagtt
tggtatagatgacctggaaatcagcagccccccagacgtgaacccaattggccatctcccagggcgtcctccactgctgttgccatga
tagtccaggagactaataagcagcccccccagacgtgaacccaattggccatctcccagggtcctgtcctccactgctacgttgccatga
accaggttgccccctcaccttcttccagttgaagtgcagtggatataacactgaaggagataagtggagctcttgatgagccagagtcctatctgg
ttagtttagagctgggcagtggatataacactgaaggagataagtggagctcttgatgagccagagtcctatctgg
tccctcagtgcatcataaaggaggagacacccctctagataatgatagtggagctcagatctgtagaagagagcgaaaagttatact
ggtctcctcagcacagccccctacgatcctccaggggctctccagagaagatggtagcagccgccagaagagggatccctctactg
ccgtcctccaaacctacggcacagcccctaccgatcctccaggggctctccagagaagatggtagcagccgccagaagagggatccctactg
tgaaaaaatggagcaaagagctgataaaacaagacaagaagctctaaaaggaggggaaagaaaggtccgcaaggagatccagtacc
gtgagtgcaaagagctgataagaagaggtccgcaaggctgtgtgttccaataaattattttgtagggaaaaaaaaaaaaaaaaa
tgaagatttgatagaatagaatgttccgcaaggctgtgtgttccaataaattattttgtagggaaaaaaaaaaaaaaaaaa
atgtgcttgtacatagagtgtgtgttccaataaattattttgtagggaaaaaaaaaaaaaaaaaa
aaaaaaaaaaaaaaaaaaaaaa    (SEQ ID NO:5)
```

FIG. 2B

```
MTEMSFLSSEVLVGDLMSPFDQSGLGAEESLGLLDDYLEVAKHFKPHGFSSDKAKAGSSEWLAVDGLVSPSNNSKEDA
FSGTDWMLEKMDLKEFDLDALLGIDDLETMPDDLLTTLDDTCDLFAPLVQETNKQPPQTVNPIGHLPESLTKPDQVAP
FTFLQPLPLSPGVLSSTPDHSFSLELGSEVDITEGDRKPDYTAYVAMIPQCIKEEDTPSDNDSGICMSPESYLGSPQH
SPSTRGSPNRSLPSPGVLCGSARPKPYDPPGEKMVAAKVKGEKLDKKLKKMEQNKTAATRYRQKKRAEQEALTGECKE
LEKKNEALKERADSLAKEIQYLKDLIEEVRKARGKKRVP    (SEQ ID NO:6)
```

FIG. 2C

GCCGGTTTGAGTTGTGCGCTCGGGTGTCCCTTCCTCTTCCCCTCCCGCAGGCTTGCGGCCACCATGGCGTAT
TAGAGGCAGCAGTGCCTGCCGGCGTTGGCCTTGCAGCGGCGCAGCAGCAGGCTCTGCAGCGGCAACC
CCACCGGCCTAAGCCATGGCGCTCTTCACGAAATCCAGCAGCAGTGTTGCTGTAACGGACAAAGATACCTTCG
AGTTAAGCACATTCCTGGAATGTCCCCCTTGATGTCCCCCCTTCGACCACTTGAAACTTGAAACAGCGAAGTGTT
GGCGGGGACTTGATGTCCCCCTTCGACCAGTCGGGTTTGGGGCTGAAGAAAGCCTAGTCTCTTAGATGACT
ATCTGAGGTGGCCAAGCACTTGAAACTTGAAACCTGGTCTTCAGCGACACAAGCGGGCTCCTCGAATGCCGGCT
ATGGATGATGGCTTGGCCAGTGCCTCAGACACCGGCAAGGAGGATGCCTTTCCGGACAGATTGGATGTTGA
GAAAATGGATCTGAAAGAGTTTGACTTGACTGTCTGTTTGAATGGATGACCTGGAAACCATGCCAGATGAGC
TCTTGACCACGTTGATGACACATGTGATCTTTTTGCCCCTCTAGTCCAAGAGACTAATAAGGAGCCCCCTCAG
ACAGTGAACCCAATTGGCCATCTCCCAGAAAGTTAATAAAAGTCGACCAGGTTGCCCCTTTACATTCTTGCA
GCCTTTCCCCTGTTCCCCAGGGGTTCTGTCTTCCAGAGCATTCCTTAGTTTAGAGCTAGGCAGTGAAG
TTGATATCTCTGAAGGAGACAGGAAGCCTGACTCTGCTTACATTACTCCTAATCCCTACCTGGCTCTCCCAGCATAG
GAAGACACTCCCTCTGACAATGACAGTGGCATCTGTATGAGCCCGGAGTCCTACCTGGTTCCCGGTGCCTCTCCCGGCCCAAAC
CCCCTCCACCTCCAGGGCCCCACCAGTTAGTTTGACAGCTAAAGTGAAGACTAAAGTGAGAGAATTGGATAAGAAGCTGAAAAGATG
CTTATGACCACCTGGAGTTAGTTTGACAGCTAAAGTGAAGACTAAAGTGAGAGAATTGGATAAGAAGCTGAAAAGATG
GAGCAAAACAAGACAGCAGTACCGCCAGGTACCGCCAGAAGAGAAGGCAGATTCTCTGCCAAGGAGATCCAGTATCTGA
TAAGGAGCTAGAAAAAAGAGGTCCGTAAGGCAAGGAAGAAGAGTTCCGTAATAGGGTAGTCAGGTGCTTTGT
AAGACCTGATAGACATAGTCTTGTGTTGCTGTGTTGCTGTTTGCTGTAATAATAAATTATTTGTAGTGAAAGT (SEQ ID NO:7)

FIG. 2D

MSFLNSEVLAGDLMSPFDQSGLGAEESLGLLDDYLEVAKHLKPHGFSSDKAGSSEWPAMDDGLASASDTGKED
AFSGTDWMLEKMDLKEFDFDALFRMDDLETMPDELLTTLDDTCDLFAPLVQETNKEPPQTVNPIGHLPESLIK
VDQVAPFTFLQPFPCSPGVLSSTPEHSFSLELGSEVDISEGDRKPDSAAYITLIPPCVKEEDTPSDNDSGICM
SPESYLGSPQHSPSTSRAPPDNLPSPGGSRGSPRPKPYDPPGVSLTAKVKTEKLDKKLKKMEQNKTAATRYRQ
KKRAEQEALTGECKELEKKNEALKEKADSLAKEIQYLKDLIEEVRKARGKKRVP (SEQ ID NO:8)

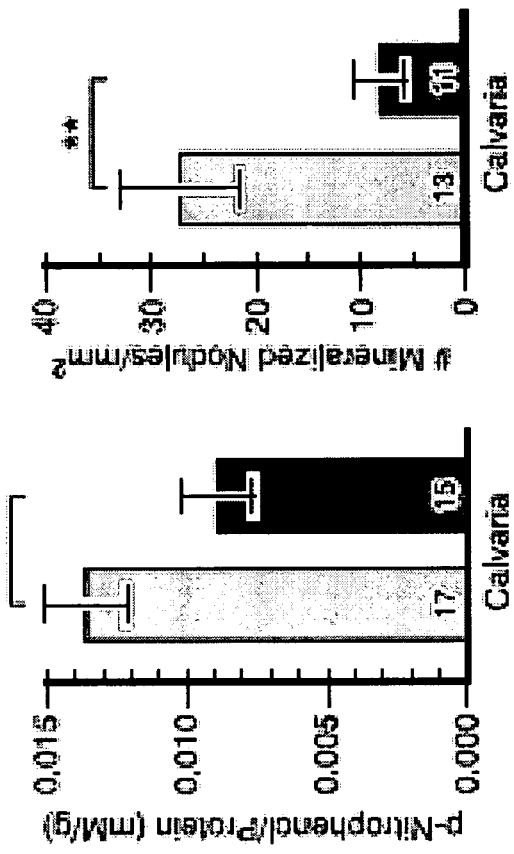
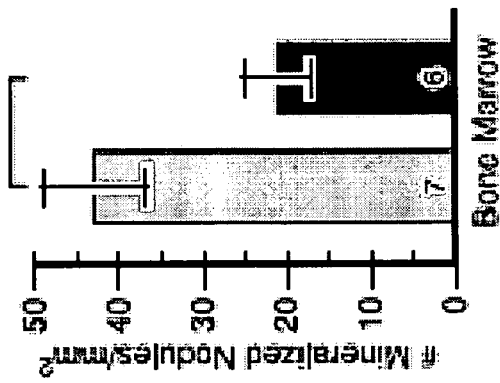
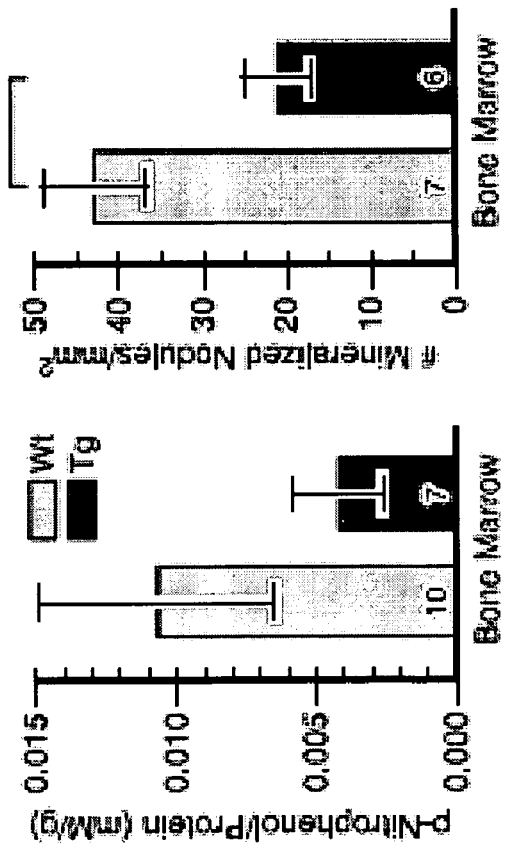
FIG. 9A  FIG. 9B  FIG. 9C  FIG. 9D

FIAT NUCLEIC ACIDS AND PROTEINS AND USES THEREOF

CROSS-REFERENCE TO RELATED APPLICATION

This application claims the benefit of the filing date of U.S. Provisional Patent Application Ser. No. 60/566,698, filed on Apr. 29, 2004. The contents of this prior application are hereby incorporated by reference in their entirety.

TECHNICAL FIELD

This invention relates to FIAT nucleic acids and proteins, and methods of using such nucleic acids and proteins.

BACKGROUND

The activating transcription factor (ATF)/cyclic adenosine monophosphate responsive element-binding (CREB) family consists of transcription factors that bind the cyclic adenosine monophosphate (cAMP) response element (CRE) through highly related, carboxy-terminal basic leucine-zipper (bZip) dimerization domains (Hai et al. (2001) Gene 273, 1-11). Several cDNA clones encoding proteins that can bind to the ATF/CRE site have been isolated. All these cDNAs encode proteins with the bZip DNA binding domain, and the proteins can be grouped into subgroups on the basis of their amino acid similarity. Proteins within each subgroup share significant similarity both inside and outside the bZip domain. Proteins between the subgroups, however, do not share much similarity other than the bZip "motif." The ATF4 subgroup includes ATF4 (also known as CREB2, TAXREB67, mATF4, C/ATF, or mTR67) (Chevray et al. (1992) Proc. Natl. Acad. Sci. USA 89:5789-93; Hai et al. (1989) Genes Dev. 3:2083-90; Karpinski et al. (1992) Proc. Natl. Acad. Sci. 89:4820-4; Mielnicki et al. (1991) Nucleic Acids Res. 19:6332; Tsujimoto et al. (1991) J. Virol. 65:1420-6; Vallejo et al. (1993) Proc. Natl. Acad. Sci. USA 90:4679-83) and ATFx (also known as ATF5) (Hai et al. (2001) Gene 273:1-11; and Persengiev (2002) Genes Dev. 16:1806-14).

ATF4 is a 381 amino acid protein containing 3 acidic regions, a hallmark of transactivation domains. Its mRNA is ubiquitously expressed and the protein exhibits a short half-life controlled through ubiquitination. ATF4 can form homodimers, but can also heterodimerize with a variety of partners, including transcription factors and kinases. It interacts with transcriptional coactivators and components of the basal transcriptional machinery. Although ATF4-dependent transcriptional repression has been reported, it is thought that the repressive activity was an experimental artifact, and it is generally assumed that ATF4 acts as a transcriptional activator. Disruption of ATF4 activity has been shown to cause severe microphthalmia, anemia, runting, and reduced bone mass in mice.

SUMMARY

The present invention is based, in part, on the identification and characterization of the protein Factor Inhibiting ATF4-mediated Transcription (FIAT). FIAT is an ATF-4 transcriptional repressor and is involved, for example, in modulating bone mass.

The present invention provides nucleic acid sequences encoding FIAT polypeptides and parts thereof, complete FIAT amino acid sequences, and examples for utilizing these sequences to repress ATF4-mediated transcription in vitro or to reduce bone mass in vivo. Descriptions of nucleic acids, proteins, vectors, host cells, and antibodies are provided. Methods for identifying compounds capable of modulating FIAT activity, pharmaceutical compositions to incorporate such compounds, and diseases that could be treated with such compounds are described. Useful animal models for testing the activity of compounds modulating FIAT activity and for the study of disorders of bone formation are detailed. The invention demonstrates that FIAT is a transcriptional repressor controlling bone mass and identifies a target for pharmacological intervention in bone cells.

Accordingly, in one aspect, the invention provides isolated nucleic acid molecules encoding polypeptides that: (i) include a FIAT polypeptide (e.g., at least six and up to all of the amino acids of a FIAT polypeptide); and (ii) display activating transcription factor-4 (ATF4) protein binding ability. In certain embodiments, the amino acid sequence of the full length FIAT polypeptide is SEQ ID NO:2, SEQ ID NO:4, or an amino acid sequence substantially identical to SEQ ID NO:2 or SEQ ID NO:4. The isolated nucleic acid molecules can further include nucleic acid sequences that encode a fusion partner, e.g., a hexa-histidine tag, a hemagglutinin tag, an immunoglobulin constant (Fc) region, a secretory sequence, and/or a detectable marker (e.g., β-galactosidase, invertase, green fluorescent protein, luciferase, chloramphenicol, acetyltransferase, beta-glucuronidase, exo-glucanase and glucoamylase. In other embodiments, the invention includes vectors that include such nucleic acid molecules, host cells that contain such vectors and/or nucleic acid molecules, polypeptides encoded by such isolated nucleic acid molecules and antibodies (e.g., polyclonal or monoclonal antibodies) or fragments thereof capable of binding to such polypeptides.

In another aspect, the invention provide cells that include exogenously—introduced nucleic acid molecules that encode FIAT or an ATF4-binding fragment thereof. In certain embodiments, the nucleic acid molecules encode SEQ ID NO:2 or SEQ ID NO:4, or a fragment thereof.

In another aspect, the invention includes isolated polypeptides that include at least six and less than all of the amino acids of SEQ ID NO: 2 or SEQ ID NO:4, and antibodies that bind to those polypeptides.

The invention also includes nucleic acid sequences that encode FIAT polypeptides with internal deletions, e.g., nucleic acids of the sequence SEQ ID NO:26, SEQ ID NO:27, or SEQ ID NO:28. The invention also includes the polypeptides encoded by these sequences.

In still another aspect, the invention includes fusion proteins that include (i) a first amino acid sequence comprising the amino acid sequence of a FIAT polypeptide, or an ATF4-binding fragment thereof; and (ii) a second amino acid sequence unrelated to the first amino acid sequence, wherein the fusion protein displays ATF4 binding ability. In certain embodiments, the first amino acid sequence includes SEQ ID NO:2 or SEQ ID NO:4, or an ATF4-binding fragment thereof. In other embodiments, the second amino acid sequence is a hexa-histidine tag, a hemagglutinin tag, an immunoglobulin constant (Fc) region, a secretory sequence, or a detectable marker. In still other embodiments, the invention includes vectors that encode such fusion proteins, host cells that include such a vector, and cells that include such fusion proteins.

In yet another aspect, the invention includes methods for identifying candidate compounds capable of interacting with a FIAT polypeptide. The methods include (a) contacting a FIAT polypeptide with a test compound; and (b) detecting an interaction of the test compound with the FIAT polypeptide, wherein an interaction indicates that the test compound is a candidate compound. Optionally, the method can further include (c) determining whether the candidate compound modulates FIAT activity in vivo or in vitro, wherein modulation indicates that the candidate compound is a FIAT modulating agent. In other embodiments, the test compound is immobilized on a substrate, and interaction of the candidate compound with the polypeptide is detected as immobilization of the polypeptide on the immobilized test compound. In still other embodiments, the test compound is selected from the group consisting of polypeptides, ribonucleic acids, small molecules, and deoxyribonucleic acids. In yet other embodiments, the FIAT polypeptide is provided as a fusion protein that includes the FIAT polypeptide fused to (i) a transcription activation domain of a transcription factor or (ii) a DNA-binding domain of a transcription factor; the test compound is a fusion protein that includes the polypeptide fused to (i) a transcription activation domain of a transcription factor or (ii) a DNA-binding domain of a transcription factor, to interact with the fusion protein; and interaction of the test compound with the FIAT polypeptide is detected as reconstitution of a transcription factor.

In still another aspect, the invention includes methods for identifying candidate compounds by: (a) providing a first polypeptide that: (i) includes a FIAT polypeptide or a fragment thereof; and (ii) displays ATF4-binding ability; (b) providing a second polypeptide that: (i) includes an ATF4 polypeptide or a fragment thereof; and (ii) displays FIAT binding ability; (c) contacting the first and second polypeptides in the presence of a test compound; and (d) comparing the level of binding between the first and second polypeptides in the presence of the test compound with the level of binding in the absence of the test compound, wherein a different level of binding in the presence of the test compound than in its absence indicates that the test compound is a candidate compound. Optionally, the method can further include (e) determining whether the candidate compound modulates FIAT activity in vivo or in vitro, wherein modulation indicates that the candidate compound is a FIAT modulating agent. In certain embodiments, the test compound is a polypeptide, ribonucleic acid, small molecule, or a deoxyribonucleic acid. In other embodiments, the first polypeptide is provided as a fusion protein that includes the FIAT polypeptide fused to (i) a transcription activation domain of a transcription factor or (ii) a DNA-binding domain of a transcription factor; the second polypeptide is a fusion protein comprising the polypeptide fused to (i) a transcription activation domain of a transcription factor or (ii) a DNA-binding domain of a transcription factor, to interact with the fusion protein; and binding of the first and second polypeptides is detected as reconstitution of a transcription factor.

In another aspect, the invention includes methods for identifying candidate compounds capable of interacting with a FIAT polypeptide by (a) contacting a FIAT polypeptide with a test compound; (b) detecting a decrease in activity of the FIAT polypeptide contacted with the test compound, wherein a compound that causes a decrease in FIAT activity is a candidate compound; and (c) determining whether the candidate compound inhibits FIAT activity in vivo, relative to FIAT activity in the absence of the test compound, wherein inhibition of FIAT activity in vivo indicates that the candidate compound is a FIAT modulating agent. In certain embodiments, the test compound is a polypeptide, ribonucleic acid, small molecule, or deoxyribonucleic acid.

In yet another aspect, the invention includes a method for identifying a candidate compound, the method comprising: (a) contacting a nucleic acid encoding FIAT with a test compound; and (b) detecting an interaction of the test compound with the nucleic acid, wherein an interaction indicates that the test compound is a candidate compound. Optionally, the method can include (c) determining whether a candidate compound inhibits FIAT activity in vivo, relative to FIAT activity in the absence of the test compound that interacts the nucleic acid, wherein inhibition of FIAT activity in vivo indicates that the candidate compound is a FIAT modulating agent. In certain embodiments, the test compound is selected from the group consisting of polypeptides, ribonucleic acids, small molecules, and deoxyribonucleic acids.

In another aspect, the invention includes pharmaceutical formulations that include a candidate compound and/or FIAT modulating agent identified by a method described herein and a pharmaceutically acceptable carrier.

In still another aspect, the invention include methods for enhancing bone formation in a subject by administering to the subject (e.g., a human or rodent) a therapeutically effective amount of a pharmaceutical formulation described herein.

In another aspect, the invention includes methods for treating subjects having inappropriate bone production by inhibiting an interaction (e.g., binding) between a FIAT polypeptide and an ATF4 polypeptide in the patient.

In another aspect, the invention includes transgenic non-human mammals, one or more of the cells of which comprise a transgene encoding a FIAT polypeptide, wherein the transgene is expressed in one or more cells of the transgenic mammal such that the mammals exhibit a FIAT-mediated disorder. All of the cells of the mammal can comprise the transgene or the mammal can be a mosaic for cells comprising the transgene. The mammal can display a changed (e.g., an increased or decreased) level of FIAT expression compared to a wild-type mammal. In some embodiments, the transgene includes a disrupted FIAT sequence. In other embodiments, the mammal constitutively expresses the FIAT transgene. In still other embodiments, the transgene is expressed in a specific cell type. In yet other embodiments, the mammal is a mouse.

In another aspect, the invention includes transgenic non-human mammals the somatic and germ cells of which comprise a disrupted FIAT gene, the disruption being sufficient to affect the expression or activity of FIAT compared to a wild-type mammal, the disrupted gene being introduced into the transgenic mammal or an ancestor of the mammal at an embryonic stage, wherein the mammal, if homozygous for the disrupted gene exhibits a FIAT-mediated disorder. In certain embodiments, the mammal has decreased (e.g., no detectable) levels of FIAT expression or activity compared to a wild type mammal. In other embodiments, the mammal is a mouse.

In another aspect, the invention includes methods of inhibiting a FIAT in a cell (e.g., a human cell) by providing a double-stranded RNA molecule (dsRNA) that targets a FIAT gene (e.g., a human FIAT gene) and exposing the cell to the dsRNA under conditions that permit induction of ribonucleic acid interference (RNAi) and inhibition of FIAT. In certain embodiments, each strand of the dsRNA molecule is 15-30 nucleotides (e.g., 19-23 nucleotides) long. The dsRNA can have a 3'dTdT sequence and/or a 5' phosphate group ($PO_4$). In certain embodiments, each strand of the dsRNA, and optionally a loop, is encoded by a sequence contained within a plasmid.

In another aspect, the invention includes methods of enhancing bone formation in a patient by administering to the patient a therapeutically effective amount of a composition that includes a nucleic acid sequence complementary to a portion of the coding strand of a FIAT DNA sequence, e.g., a nucleic acid sequence that includes a dsRNA that inhibits the activity, expression, biochemical, cellular and/or physiological function of FIAT. In certain embodiments, the composition includes a one or more nucleic acids of the sequence SEQ ID NO:14, SEQ ID NO:15, SEQ ID NO:16, SEQ ID NO:17, SEQ ID NO:18, and SEQ ID NO:19.

In another aspect, the invention includes isolated nucleic acid molecules, e.g., dsRNA molecules, that specifically inhibit expression of FIAT nucleic acids. The isolated nucleic acid molecules can include the nucleotide sequence of SEQ ID NO:15, SEQ ID NO:17, or SEQ ID NO:19. The invention also includes vectors that, when transcribed, produce isolated nucleic acid molecules that specifically inhibit expression of FIAT nucleic acids. The invention also includes pharmaceutical compositions and cells that include isolated nucleic acid molecules that specifically inhibit expression of FIAT nucleic acids.

In another aspect, the invention includes isolated dsRNAs that include the sequences SEQ ID NO:14 and SEQ ID NO:15; or SEQ ID NO:16 and SEQ ID NO:17; or SEQ ID NO:18 and SEQ ID NO:19.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

DESCRIPTION OF DRAWINGS

FIG. 1A is a nucleic acid sequence listing of human FIAT cDNA (SEQ ID NO:1). The ATG translation start codon and TAA translation stop codons are boxed.

FIG. 1B is an amino acid sequence listing of a human FIAT polypeptide (SEQ ID NO:2). The leucine zipper is boxed. An alanine residue substitutes for the second leucine in the zipper (alanine can substitute for leucine in functional zippers).

FIG. 1C is a nucleic acid sequence listing of a mouse FIAT cDNA (SEQ ID NO:3).

FIG. 1D is an amino acid sequence listing of a mouse FIAT polypeptide (SEQ ID NO:4).

FIG. 2A is a nucleic acid sequence listing of a human ATF4 cDNA (SEQ ID NO:5).

FIG. 2B is an amino acid sequence listing of a human ATF4 polypeptide (SEQ ID NO:6).

FIG. 2C is a nucleic acid sequence listing of a mouse ATF4 cDNA (SEQ ID NO:7).

FIG. 2D is an amino acid sequence listing of a mouse ATF4 polypeptide (SEQ ID NO:8).

FIG. 4A depicts growth on two-minus selection media. FIG. 4B depicts growth on three-minus selection media. Growth on three-minus selection media confirms protein-protein interactions.

FIG. 4C: Endogenous ATF4 was immunoprecipitated from ROS 17/2.8 osteoblastic cells using an anti-ATF4 antibody, and the immunoprecipitates were probed with the anti-FIAT antibody (left panel). FIG. 4D: Endogenous FIAT was immunoprecipitated from ROS 17/2.8 cells using the anti-FIAT antibody, and the immunoprecipitates were probed with an anti-ATF4 antibody (right panel).

FIG. 5A: Cos-7 cells were transfected with a luciferase reporter gene under the control of three canonical ATF4 binding sites, together with expression vectors for human ATF4 and human FIAT. FIG. 5B: MC3T3-E1 osteoblastic cells were transfected with a reporter construct in which the luciferase gene was regulated by six copies of the wild-type (OSE1-luc) or mutated (mut OSE1) OSE1 sequence from the mouse osteocalcin gene promoter. Co-transfected plasmids included expression vectors for ATF4, RSK2, or FIAT (2× signifies that twice the amount of plasmid was used).

FIG. 7A depicts bone mineral density. FIG. 7B depicts bone volume. FIG. 7C depicts mineralized volume. FIG. 7D depicts trabecular thickness. FIG. 7E depicts trabecular number. FIG. 7F depicts ultimate displacement. FIG. 7G depicts osteoblast number. FIG. 7H depicts mineral apposition rate. FIG. 7I depicts bone formation rate.

FIGS. 9A-9B are bar graphs of activity of primary cultures of osteoblasts obtained from 6-8 days old calvaria. *, $p<0.05$;

**, p<0.01. FIG. 9A depicts alkaline phosphatase activity at day 7 of culture normalized to protein concentration. FIG. 9B depicts alizarin red staining at day 14 of culture.

FIGS. 9C-9D are bar graphs of activity of primary cultures of osteoblasts obtained from 3 months old bone marrow stromal cells. *, p<0.05; **, p<0.01. FIG. 9A depicts alkaline phosphatase activity at day 7 of culture normalized to protein concentration. FIG. 9B depicts alizarin red staining at day 14 of culture.

FIG. 10A depicts expression of OCN. FIG. 10B depicts expression of Fiat. FIG. 10C depicts expression of Atf4. FIG. 10D depicts expression of Runx2. FIG. 10E depicts expression of Osx. FIG. 10F depicts expression of Bsp.

FIG. 11A depicts expression of calvarial Col1A1 mRNA levels quantified by Real Time PCR. FIG. 11B depicts collagen protein content in whole tibias from 3 month-old mice as estimated using hydroxyproline quantification. FIG. 11C depicts type I collagen synthesis analysis. The graph shows expression of $^3$H-proline-labeled α1 and α2 chains of type I collagen relative to β-actin expression (n=9 independent primary osteoblast cultures from different litters for each bar). NEAA, non-essential amino acids.

DETAILED DESCRIPTION

Figures 3A, 3B:
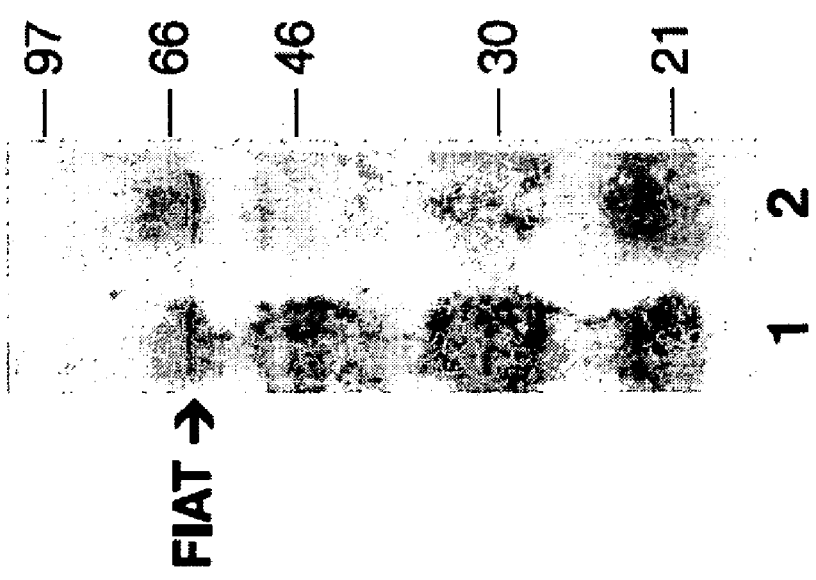
FIG. 3A is a Western blot of nuclear extracts from MC3T3-E1 osteoblastic cells at confluence (line 1) or after 6 days of growth in the presence of ascorbic acid and beta-glycerophosphate (line 2), which were separated by sodium dodecylsulfate-polyacrylamide gel electrophoresis, transferred to nitrocellulose, and probed with an anti-FIAT peptide antibody. The arrow identifies the 66 kDa FIAT protein in both lanes.
FIG. 3B is a micrograph of fixed calvarial osteoblasts from primary cultures stained with the anti-FIAT antibody and an anti-rabbit secondary antibody coupled to rhodamine. The endogenous FIAT protein is detected in the nucleus of the cells.

The present invention is based, in part, on the isolation and characterization of a leucine zipper-containing transcriptional regulatory molecule, FIAT. FIAT is a 66 kDa protein that can localize to the nucleus to inhibit ATF4-mediated gene transcription. Transgenic animals that overexpress FIAT in osteoblasts have decreased bone mass. FIAT nucleic acids and polypeptides are useful, for example, as targets for identifying compounds that modulate FIAT activity and, therefore, bone formation.

I. Nucleic Acids, Proteins, Vectors, and Host Cells

In one aspect, the invention includes certain FIAT nucleic acids. Exemplary FIAT nucleic acids include human and mouse FIAT nucleic acid sequences, such as SEQ ID NOS:1 and 3 as shown in FIGS. 1A and 1C, respectively.

Also included within the present invention are fragments of FIAT and certain fragments of ATF-4 nucleic acids, e.g., fragments of SEQ ID NOS:1, 3, 5, or 7. Fragments of FIAT or ATF-4 nucleic acids encode at least one useful fragment of a FIAT or ATF-4 polypeptide (e.g., a human or rodent polypeptide), respectively, such as a binding domain (e.g., a leucine zipper or fragment thereof), or other useful fragment. For example, a useful fragment of a FIAT nucleic acid may encode a fragment of a FIAT polypeptide having binding activity, e.g., a fragment corresponding to amino acids from about 194 to about 222, inclusive, of SEQ ID NO.:1. As another example, a useful fragment of an ATF-4 nucleic acid may encode a fragment of a ATF-4 polypeptide having binding activity, e.g., a fragment corresponding to amino acids from about 300 to about 346, inclusive, of SEQ ID NO:6.

FIAT and ATF-4 nucleic acids described herein include both RNA and DNA, including genomic DNA and synthetic (e.g., chemically synthesized) DNA. Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "isolated nucleic acid" means a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated FIAT or ATF-4 nucleic acid includes some or all of the 5' non-coding (e.g., promoter) sequences that are immediately contiguous to the FIAT or ATF-4 nucleic acid coding sequence. The term includes, for example, recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence.

The term "purified" refers to a FIAT or ATF-4 nucleic acid (or FIAT or ATF-4 polypeptide) that is substantially free of cellular or viral material with which it is naturally associated, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

In some embodiments, the invention includes nucleic acid sequences that are substantially identical to a FIAT or ATF-4 nucleic acid. A nucleic acid sequence that is "substantially identical" to a FIAT or ATF-4 nucleic acid is at least 75% identical (e.g., at least about 80%, 85%, 90%, or 95% identical) to the FIAT or ATF-4 nucleic acid sequences represented by SEQ ID NOS:1, 3, 5, or 7. For purposes of comparison of nucleic acids, the length of the reference nucleic acid sequence will be at least 50 nucleotides, but can be longer, e.g., at least 60 nucleotides, or more nucleotides.

To determine the percent identity of two amino acid or nucleic acid sequences, the sequences are aligned for optimal comparison purposes (i.e., gaps can be introduced as required in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). The two sequences can be of the same length.

The percent identity or homology between two sequences is determined using the mathematical algorithm of Karlin and Altschul (1990) *Proc. Nat'l Acad. Sci. USA* 87:2264-2268, modified as in Karlin and Altschul (1993) *Proc. Nat'l Acad. Sci. USA* 90:5873-5877. Such an algorithm is incorporated into the NBLAST and XBLAST programs of Altschul, et al. (1990); *J. Mol. Biol.* 215:403-410. BLAST nucleotide searches are performed with the NBLAST program, score=100, wordlength=12 to obtain nucleotide sequences homologous to FIAT nucleic acid molecules of the invention. BLAST protein searches are performed with the XBLAST program, score=50, wordlength=3 to obtain amino acid sequences homologous to FIAT protein molecules of the invention. To obtain gapped alignments for comparison purposes, Gapped BLAST is utilized as described in Altschul et al., (1997) *Nucleic Acids Res.* 25:3389-3402. When utilizing BLAST and Gapped BLAST programs, the default parameters of the respective programs (e.g., XBLAST and NBLAST) are used. See online at ncbi.nlm.nih.gov.

In other embodiments, the invention includes variants, homologs, and/or fragments of certain FIAT or ATF-4 nucleic acids, e.g., variants, homologs, and/or fragments of FIAT or ATF-4 nucleic acid sequences represented by SEQ ID NOs: 1, 3, 5, or 7. The terms "variant" or "homolog" in relation to FIAT or ATF-4 nucleic acids include any substitution, variation, modification, replacement, deletion, or addition of one (or more) nucleotides from or to the sequence of a FIAT or ATF-4 nucleic acid. The resultant nucleotide sequence may encode a FIAT or ATF-4 polypeptide that is generally at least as biologically active as the referenced FIAT or ATF-4 polypeptide (e.g., as represented by SEQ ID NOs:2, 4, 6, or 8). In particular, the term "homolog" covers homology with respect to structure and/or function provided that the resultant nucleotide sequence codes for or is capable of coding for a FIAT or ATF-4 polypeptide being at least as biologically active as FIAT or ATF-4 encoded by a sequence shown herein as SEQ ID NOs:1, 3, 5, or 7, respectively. With respect to sequence homology, there is at least 75% (e.g., 85%, 90%, 95%, 98%, or 100%) homology to the sequence shown as SEQ ID NOs:1, 3, 5, or 7.

Also included within the scope of the present invention are certain alleles of certain FIAT or ATF-4 genes. As used herein, an "allele" or "allelic sequence" is an alternative form of FIAT or ATF-4. Alleles result from a mutation, i.e., a change in the nucleotide sequence, and generally produce altered mRNAs or polypeptides whose structure or function may or may not be altered. Any given gene can have none, one, or more than one allelic form. Common mutational changes that give rise to alleles are generally ascribed to deletions, additions or substitutions of amino acids. Each of these types of changes can occur alone, or in combination with the others, one or more times in a given sequence.

The invention also includes nucleic acids that hybridize, e.g., under stringent hybridization conditions (as defined herein) to all or a portion of the nucleotide sequences represented by SEQ ID NOs: 1, 3, 5, or 7, or a complement thereof. The hybridizing portion of the hybridizing nucleic acids is typically at least 15 (e.g., 20, 30, or 50) nucleotides in length. The hybridizing portion of the hybridizing nucleic acid is at least about 75%, e.g., at least about 80%, 95%, 98% or 100%, identical to the sequence of a portion or all of a nucleic acid encoding an FIAT or ATF-4 polypeptide, or to its complement. Hybridizing nucleic acids of the type described herein can be used as a cloning probe, a primer (e.g., a PCR primer), or a diagnostic probe. Nucleic acids that hybridize to the nucleotide sequence represented by SEQ ID NO: 1, 3, 5, or 7, are considered "antisense oligonucleotides."

High stringency conditions are hybridizing at 68° C. in 5×SSC/5× Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Stringent conditions include washing in 3×SSC at 42° C. The parameters of salt concentration and temperature can be varied to achieve the optimal level of identity between the probe and the target nucleic acid. Additional guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

The present invention also encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire FIAT coding strand, or to only a portion thereof, e.g., all or part of the protein coding region (or open reading frame). An antisense nucleic acid molecule can be antisense to a noncoding region of the coding strand of a nucleotide sequence encoding FIAT. The noncoding regions ("5' and 3' untranslated regions") are the 5' and 3' sequences which flank the coding region and are not translated into amino acids. Given the coding strand sequences encoding FIAT disclosed herein, antisense nucleic acids of the invention can be designed according to the rules of Watson and Crick base pairing. The antisense nucleic acid molecule can be complementary to the entire coding region of FIAT mRNA, or, in some instances, complementary to only a portion of the coding or noncoding region of FIAT mRNA. An antisense oligonucleotide can be, for example, about 5, 10, 15, 18, 20, 25, 30, 35, 40, 45 or 50 nucleotides in length. Exemplary useful antisense oligonucleotides include, but are not limited to, antisense oligonucleotides that include a sequence of at least 8 nucleotides complementary to a SEQ ID NO:1 or SEQ ID NO:3, e.g., SEQ ID NOs: 15, 17, 19, 21, 23, and 25.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides that can be used to generate antisense nucleic acids include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, an antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention can be administered to a subject or generated in situ such that they hybridize with or bind to cellular mRNA and/or genomic DNA encoding a FIAT protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix.

Antisense nucleic acids can be administered, for example, by direct injection at a tissue site. Alternatively, antisense nucleic acid molecules can be modified to target selected cells for systemic administration. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. Antisense nucleic acid molecules can also be delivered to cells using certain vectors described herein. Vector constructs in which the antisense nucleic acid molecule is placed under the control of a strong pol II or pol III promoter can be used to achieve sufficient intracellular concentrations of antisense molecules.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330).

The invention also includes nucleic acids capable of inhibiting expression of FIAT by way of RNA interference (RNAi). RNAi is a process whereby double-stranded RNA (dsRNA) induces the sequence-specific degradation of homologous mRNA in animals and plant cells (Hutvagner and Zamore, Curr. Opin. Genet. Dev., 12:225-232, 2002; Sharp, Genes Dev. 15:485-490, 2001). In mammalian cells, RNAi can be triggered by, e.g., 21-nucleotide (nt) duplex RNAs, also called small inhibitory RNAs (siRNAs) (Chiu et al., Mol. Cell. 10:549-561, 2002; Elbashir et al., Nature 411:494-498, 2001), or by micro-RNA (mRNA), functional small-hairpin RNA (shRNA), or dsRNAs that are expressed in vivo using DNA templates with RNA polymerase III promoters (Zeng et al., Mol. Cell 9:1327-1333, 2002; Paddison et al., Genes Dev. 16:948-958, 2002; Lee et al., Nature Biotechnol. 20:500-505, 2002; Paul et al., Nature Biotechnol. 20:505-508, 2002; Tuschl, Nature Biotechnol. 20:440-448, 2002; Yu et al., Proc. Natl. Acad. Sci. USA 99:6047-6052, 2002; McManus et al., RNA 8:842-850, 2002; Sui et al., Proc. Natl. Acad. Sci. USA 99:5515-5520, 2002; see also Hannon, Nature 418:244-251, 2002). The suppression, also known as "silencing" is predominantly a cytoplasmic, post-transcriptional event that is evolutionarily conserved (see Hutvagner and Zamore, Curr. Opin. Genet. Dev. 12:225-232, 2002). While the silencing mechanism is not fully understood, current models suggest that dsRNA is processed into siRNA by the RNAse III enzyme, Dicer. The siRNA then forms a complex called RNA-induced silencing complex (RISC). This complex then interacts with the target mRNA, which is then cleaved and degraded (Martinez et al., Cell 110:563-574, 2002; Schwarz et al., Mol. Cell. 10:537-548, 2002). shRNAs have been studied in mammalian cells (Paul et al., Genes & Dev. 16:948-958, 2002), and can be expressed effectively in human cells (Sui et al., Nature Biotechnol. 20:505-508, 2002). A DNA vector-based RNAi technology to suppress gene expression in mammalian cells is described by Yu and Turner (Proc. Natl. Acad. Sci. USA 99:5515-5520, 2002). RNAi by expression of siRNAs and shRNAs in mammalian cells has also been described by Yu et al. (Proc. Natl. Acad. Sci. USA 99:6047-6052, 2002). More information about shRNA design and use, or about RNAi generally, may be found on the internet (e.g., at katahdin.cshl.org:9331/RNAi/docs/BseRI-BamHI_Strategy.pdf and katahdin.cshl.org:9331/RNAi/docs/Web_version_of_PCR_strategy1.pdf).

The present invention includes siRNAs, duplexes thereof (i.e., dsRNAs), shRNAs, and mRNAs, which interact with (e.g., bind) a FIAT target sequence (e.g., a FIAT mRNA (e.g., an mRNA corresponding to human FIAT sequences such as those shown herein)). Such nucleic acids can be, e.g., chemically synthesized RNA oligonucleotides (see Elbashir et al., supra). Exemplary siRNAs encompassed by and useful in the present invention are those that include SEQ ID NOs:14-19, as shown in Example 5, below.

Plasmids can be used to encode shRNAs that can function as siRNAs (see Sui et al., Proc. Natl. Acad. Sci. USA 99:5515-5520, 2002; Brummelkamp et al., Science 296:550-553, 2002). Such plasmids can contain, e.g., an RNA polymerase III promoter, followed by sequence encoding a sense sequence, a loop structure, and an antisense sequence. A variety of loops have been successfully employed, as have several polymerase III promoters (Brummelkamp et al., Science 296:550-553, 2002; Miyagishi and Taira, Nucl. Acids Res. 2:113-114, 2002). Vectors (e.g., plasmids) containing a promoter (e.g., an RNA polymerase III promoter) operably linked to a FIAT "sense" sequence, a loop structure, and the corresponding FIAT "antisense" sequence can be made using procedures that are routine in the art. As U6-promoter-driven siRNAs with four uridine 3' overhangs have been shown to suppress targeted gene expression in mammalian cells (Paddison et al., Nature Biotechnol. 20:497-500, 2002), vectors of the present invention can include a U6 promoter and siRNAs with uridine overhangs (e.g., 1-6 uridines at the 3' terminus). Exemplary shRNAs encompassed by and useful in the present invention are described in the Examples section and comprise the sense and antisense sequences set forth herein as SEQ ID NOs: 20-25, as shown in Example 5, below.

Typically, mRNAs are excised from an approximately 70-nucleotide precursor RNA stem-loop (the shRNA), possibly by the RNase III-type enzyme known as Dicer or a homolog thereof. By substituting the stem sequences of the mRNA precursor with mRNA sequence complementary to the target mRNA (here, a FIAT mRNA), a vector construct that expresses the mRNA can be used to produce siRNAs to initiate RNAi against specific mRNA targets in mammalian cells (Zeng, supra).

The nucleic acids of the invention can also be included in, and expressed by, viral vectors. Accordingly, the invention features viral vectors that induce specific silencing of FIAT through expression of siRNA. For example, FIAT-specific adenoviral vectors can be constructed by generating recombinant adenoviruses harboring siRNA under RNA Pol II promoter transcription control (Xia et al., supra).

siRNAs or other nucleic acid-based inhibitors can be administered to animals and humans using any method know in the art. For example, a "high-pressure" delivery technique can be used, such as a rapid injection (for example, an injection that is complete within a few seconds (e.g., 5 seconds)) of a large volume of an siRNA-containing solution into the animal via an artery or vein (see Liu, supra; McCaffrey, supra; and Lewis, Nature Genetics 32:107-108, 2002. Nanoparticles and liposomes can also be used to deliver siRNAs, and such siRNAs that target FIAT and that are associated with a nanoparticle or liposome, or that are otherwise formulated for delivery to a biological cell, are within the scope of the present invention.

dsRNA molecules of the present invention can include about 15 or more (e.g., 12, 13, 14, 15, 16, 17, 18, 19, 20, 21, 22, 23, 24, 25, 26, 27, 28, 29, 30 or more) nucleotides in each strand. The strands of the dsRNA can be substantially complementary to a target region of FIAT mRNA. For example, the first and second strands can be about 70% (e.g., about 70%, 75%, 85%, 90%, 95%, or 100%) complementary to a target region of FIAT mRNA. The target region can be any region of the FIAT nucleic acid sequence, e.g., a region corresponding to SEQ ID NO:1 or SEQ ID NO:3.

dsRNA molecules of the invention can be produced by, e.g., chemically synthesizing the molecule, transcribing the molecule in vitro from a DNA template, making the molecule in vivo from, e.g., shRNA (generation of dsRNAs and other inhibitory nucleic acids is discussed further above), or using any other method known in the art. For example, each strand of a dsRNA can be chemically synthesized using naturally occurring nucleotides or variously modified nucleotides designed to increase the biological stability of the molecules or to increase the physical stability of the duplex formed between the antisense and sense strands of the dsRNA (e.g., phosphorothioate derivatives and acridine substituted nucleotides can be used). The dsRNA can also be produced using an expression vector into which a nucleic acid including both the sense and antisense sequences has been cloned (e.g., an RNA transcribed from the inserted nucleic acid may form a hairpin, the stem of which forms the dsRNA that includes an antisense strand that is complementary to a FIAT RNA). Accordingly, one can make a dsRNA that inhibits a FIAT by providing a FIAT nucleic acid sequence and generating (or designing) a dsRNA that includes a sequence that is the reverse and complement of the FIAT nucleic acid sequence. A method of making a dsRNA can further include testing the dsRNA by its exposure to FIAT-expressing cells. An anti-FIAT dsRNA will decrease expression of FIAT (e.g., will decrease the levels of FIAT protein and FIAT RNA) in the cells. FIAT expression can be assayed by methods known in the art. For example, levels of FIAT protein can be assayed by Western blot analysis, and levels of FIAT RNA can be assayed by Northern blot, in situ analysis, or reverse transcription coupled with polymerase chain reaction (RT-PCR).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave FIAT mRNA transcripts to thereby inhibit translation of FIAT mRNA. A ribozyme having specificity for a FIAT-encoding nucleic acid can be designed based upon the nucleotide sequence of a FIAT cDNA disclosed herein. For example, a derivative of a Tetrahymena L-19 IVS RNA can be constructed in which the nucleotide sequence of the active site is complementary to the nucleotide sequence to be cleaved in a FIAT-encoding mRNA. See, e.g., Cech et al. U.S. Pat. No. 4,987,071; and Cech et al. U.S. Pat. No. 5,116,742. Alternatively, FIAT mRNA can be used to select a catalytic RNA having a specific ribonuclease activity from a pool of RNA molecules. See, e.g., Bartel and Szostak (1993) Science 261:1411-1418.

The invention also encompasses nucleic acid molecules which form triple helical structures. For example, FIAT gene expression can be inhibited by targeting nucleotide sequences complementary to the regulatory region of the FIAT (e.g., the FIAT promoter and/or enhancers) to form triple helical structures that prevent transcription of the FIAT gene in target cells. See generally, Helene (1991) Anticancer Drug Des. 6(6):569-84; Helene (1992) Ann. N.Y. Acad. Sci. 660:27-36; and Maher (1992) Bioassays 14(12):807-15.

In certain embodiments, the nucleic acid molecules of the invention are modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670-675.

PNAs of FIAT can be used for therapeutic and diagnostic applications. For example, PNAs can be used as antisense or antigene agents for sequence-specific modulation of gene expression by, e.g., inducing transcription or translation arrest or inhibiting replication. PNAs of FIAT can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670-675).

In another embodiment, PNAs of FIAT can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of FIAT can be generated, which may combine the advantageous properties of PNA and DNA. Such chimeras allow DNA recognition enzymes, e.g., RNAse H and DNA polymerases, to interact with the DNA portion while the PNA portion provides high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag et al. (1989) Nucleic Acid Res. 17:5973-88). PNA monomers are then coupled in a stepwise manner to produce a chimeric molecule with a 5' PNA segment and a 3' DNA segment (Finn et al. (1996) Nucleic Acids Research 24(17):3357-63). Alternatively, chimeric molecules can be synthesized with a 5' DNA segment and a 3' PNA segment (Peterser et al. (1975) Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958-976) or intercalating agents (see, e.g., Zon (1988) Pharm. Res. 5:539-549). To this end, the oligonucleotide may be conjugated to another molecule, e.g., a peptide, hybridization triggered cross-linking agent, transport agent, hybridization-triggered cleavage agent, etc.

Also included in the invention are genetic constructs (e.g., vectors and plasmids) that include a FIAT and/or ATF-4 nucleic acid described herein, operably linked to a transcription and/or translation sequence to enable expression, e.g., expression vectors. A selected nucleic acid, e.g., a DNA molecule encoding a FIAT or ATF-4 polypeptide, is "operably linked" to another nucleic acid molecule, e.g., a promoter, when it is positioned either adjacent to the other molecule or in the same or other location such that the other molecule can direct transcription and/or translation of the selected nucleic acid.

Also included in the invention are various engineered cells, e.g., transformed host cells, which contain a FIAT and/or ATF-4 nucleic acid described herein. A transformed cell is a cell into which (or into an ancestor of which) has been introduced, by means of standard techniques, a nucleic acid encoding an FIAT or ATF-4 polypeptide. Both prokaryotic and eukaryotic cells are included, e.g., mammalian cells (e.g., osteoblasts) fungi (such as yeast), and bacteria (such as *Escherichia coli*), and the like. An engineered cell exemplary of the type included in the invention is an osteoblast that overexpresses a FIAT transgene, as described in the Examples section.

Certain FIAT and ATF-4 polypeptides are also included within the present invention. Examples of FIAT polypeptides are human and mouse FIAT polypeptides, such as those shown in SEQ ID NOS:2 or 4, respectively. Examples of ATF-4 polypeptides are human and mouse ATF-4 polypeptides, such as those shown in SEQ ID NOS:6 and 8. Included within the present invention are FIAT polypeptides encoded by FIAT nucleic acids described herein. Also included within the present invention are certain fragments of FIAT and ATF-4 polypeptides, e.g., fragments of SEQ ID NOS:2, 4, 6, and 8. Fragments of FIAT and ATF-4 polypeptides may include at least one binding domain, or other useful portion of a full-length FIAT or ATF-4 polypeptide. For example, useful fragments of FIAT and ATF-4 polypeptides include, but are not limited to, fragments having binding activity (e.g., amino acids about 194 to about 222, inclusive, of SEQ ID NO.:2, and amino acids about 300 to about 346 of SEQ ID NO:6, respectively) and portions of such fragments.

The terms "protein" and "polypeptide" both refer to any chain of amino acids, regardless of length or post-translational modification (e.g., glycosylation or phosphorylation). Thus, the terms "FIAT protein," "ATF-4 protein," "FIAT polypeptide," and "ATF-4 polypeptide" include full-length naturally occurring isolated proteins, as well as recombinantly or synthetically produced polypeptides that correspond to the full-length naturally occurring proteins, or to a fragment of the full-length naturally occurring or synthetic polypeptide.

As discussed above, the terms "FIAT polypeptide," and "ATF-4 polypeptide" include biologically active fragments of naturally occurring or synthetic FIAT and ATF-4 polypeptides, respectively. Fragments of a protein can be produced by any of a variety of methods known to those skilled in the art, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of such mutagenized DNA can produce polypeptide fragments. Digestion with "end-nibbling" endonucleases can thus generate DNAs that encode an array of fragments. DNAs that encode fragments of a protein can also be generated, e.g., by random shearing, restriction digestion, chemical synthesis of oligonucleotides, amplification of DNA using the polymerase chain reaction, or a combination of the above-discussed methods. Fragments can also be chemically synthesized using techniques known in the art, e.g., conventional Merrifield solid phase FMOC or t-Boc chemistry. For example, peptides of the present invention can be arbitrarily divided into fragments of desired length with no overlap of the fragments, or divided into overlapping fragments of a desired length.

A purified or isolated compound is a composition that is at least 60% by weight the compound of interest, e.g., a FIAT polypeptide, ATF-4 polypeptide, or antibody. Typically, the preparation is at least 75% (e.g., at least 90%, 95%, or 99%) by weight the compound of interest. Purity can be measured by any appropriate standard method, e.g., column chromatography, polyacrylamide gel electrophoresis, or HPLC analysis.

In certain embodiments, FIAT and ATF-4 polypeptides include sequences substantially identical to all or portions of a naturally occurring FIAT and ATF-4 polypeptides. Polypeptides "substantially identical" to the FIAT and ATF-4 polypeptide sequences described herein have an amino acid sequence that is at least 65% (e.g., at least 75%, 80%, 85%, 90%, 95% or 99%, e.g., 100%), identical to the amino acid sequences of the FIAT and ATF-4 polypeptides represented by SEQ ID NOs:2, 4, 6, and 8 (measured as described herein). For purposes of comparison, the length of the reference FIAT or ATF-4 polypeptide sequence can be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also can be, e.g., a 100 amino acid long polypeptide that is 50% identical to the reference polypeptide over its entire length.

FIAT and ATF-4 polypeptides of the invention include, but are not limited to, recombinant polypeptides and natural polypeptides. Also included are nucleic acid sequences that encode forms of FIAT and ATF-4 polypeptides in which naturally occurring amino acid sequences are altered or deleted. Certain nucleic acids of the present invention may encode polypeptides that are soluble under normal physiological conditions.

Also within the invention are nucleic acids encoding fusion proteins in which a portion of a FIAT and/or ATF-4 polypeptide is fused to an unrelated polypeptide, also referred to herein as a "heterologous polypeptide" (e.g., a marker polypeptide or a fusion partner) to create a fusion protein. For example, the polypeptide can be fused to a hexa-histidine tag or a FLAG tag to facilitate purification of bacterially expressed polypeptides or to a hemagglutinin tag or a FLAG tag to facilitate purification of polypeptides expressed in eukaryotic cells. The invention also includes, for example, isolated polypeptides (and the nucleic acids that encode these polypeptides) that include a first portion and a second portion, where the first portion includes, e.g., a FIAT or ATF-4 polypeptide, and the second portion includes an immunoglobulin constant (Fc) region or a detectable marker (e.g., β-galactosidase, invertase, green fluorescent protein, luciferase, chloramphenicol acetyltransferase, beta-glucuronidase, exoglucanase, and/or glucoamylase).

The fusion partner can be, for example, a polypeptide that facilitates secretion, e.g., a secretory sequence. Such a fused polypeptide is typically referred to as a preprotein. The secretory sequence can be cleaved by the host cell to form the mature protein. Also within the invention are nucleic acids that encode a FIAT and/or ATF-4 polypeptide fused to a polypeptide sequence to produce an inactive preprotein. Preproteins can be converted into the active form of the protein by removal of the inactivating sequence.

II. Antibodies

The invention features purified or isolated antibodies that bind, e.g., specifically bind, to a FIAT polypeptide, i.e., anti-FIAT antibodies. An antibody "specifically binds" to a particular antigen, e.g., a FIAT polypeptide, when it binds to that antigen, but recognizes and binds to a lesser extent (e.g., does not recognize and bind) to other molecules in a sample, e.g., a biological sample that includes a FIAT polypeptide. Antibodies of the invention include monoclonal antibodies, polyclonal antibodies, humanized or chimeric antibodies, single chain antibodies, Fab fragments, F(ab')$_2$ fragments, and molecules produced using a Fab expression library.

An example of a type of antibody included in the present invention is the polyclonal anti-FIAT antibody described herein. Such an antibody can be produced as follows: a peptide corresponding to FIAT amino acid residues about 111 to about 125 (e.g., of SEQ ID NO:2 or SEQ ID NO:4), inclusive, is synthesized, coupled to ovalbumin, and injected into rabbits to raise rabbit polyclonal antibodies.

As used herein, the term "antibody" refers to a protein comprising at least one, e.g., two, heavy (H) chain variable regions (abbreviated herein as VH), and at least one, e.g., two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917). Each VH and VL is composed of three CDR's and four FRs, arranged from amino-terminus to carboxy-terminus in the following order: FR1, CDR1, FR2, CDR2, FR3, CDR3, FR4.

An anti-FIAT antibody can further include a heavy and light chain constant region, to thereby form a heavy and light immunoglobulin chain, respectively. The antibody can be a tetramer of two heavy immunoglobulin chains and two light immunoglobulin chains, wherein the heavy and light immunoglobulin chains are interconnected by, e.g., disulfide bonds. The heavy chain constant region is comprised of three domains, CH1, CH2, and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

A "FIAT binding fragment" of an antibody refers to one or more fragments of a full-length antibody that retain the ability to specifically bind to FIAT polypeptide or a portion thereof. Examples of FIAT polypeptide binding fragments of an anti-FIAT antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "FIAT binding fragment" of an antibody. These antibody fragments can be obtained using conventional techniques known to those with skill in the art.

To produce antibodies, FIAT polypeptides (or antigenic fragments (e.g., fragments of FIAT that appear likely to be antigenic by criteria such as high frequency of charged residues) or analogs of such polypeptides), e.g., those produced by standard recombinant or peptide synthetic techniques (see, e.g., Ausubel et al., supra), can be used. In general, the polypeptides can be coupled to a carrier protein, such as KLH, as described in Ausubel et al., supra, mixed with an adjuvant, and injected into a host mammal. A "carrier" is a substance that confers stability on, and/or aids or enhances the transport or immunogenicity of, an associated molecule. For example, nucleic acids encoding FIAT or fragments thereof can be generated using standard techniques of PCR, and can be cloned into a pGEX expression vector (Ausubel et al., supra). Fusion proteins can be expressed in *E. coli* and purified using a glutathione agarose affinity matrix as described in Ausubel, et al., supra.

Typically, to produce antibodies, various host animals are injected with FIAT polypeptides. Examples of suitable host animals include rabbits, mice, guinea pigs, rats, and fowl. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Such procedures result in the production of polyclonal antibodies, i.e., heterogeneous populations of antibody molecules derived from the sera of the immunized animals. Antibodies can be purified from blood obtained from the host animal, for example, by affinity chromatography methods in which the FIAT polypeptide antigen is immobilized on a resin.

The present invention also includes anti-FIAT monoclonal antibodies. Monoclonal antibodies (mAbs), which are homogeneous populations of antibodies to a particular antigen, can be prepared using FIAT polypeptides and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; Ausubel et al., supra).

Typically, monoclonal antibodies are produced using any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., *Monoclonal Antibodies and Cancer Therapy*, Alan R. Liss, Inc., pp. 77-96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies can be tested for recognition, e.g., specific recognition, of FIAT in an immunoassay, such as a Western blot or immunoprecipitation analysis using standard techniques, e.g., as described in Ausubel et al., supra. Antibodies that specifically bind to a FIAT polypeptide, or conservative variants thereof, are useful in the invention. For example, such antibodies can be used in an immunoassay to detect a FIAT polypeptide in a sample, e.g., a tissue sample.

Alternatively or in addition, an antibody can be produced recombinantly, e.g., produced by phage display or by combinatorial methods as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982.

Anti-FIAT antibodies can be fully human antibodies (e.g., an antibody made in a mouse which has been genetically engineered to produce an antibody from a human immunoglobulin sequence), or non-human antibodies, e.g., rodent (mouse or rat), goat, primate (e.g., monkey), camel, donkey, porcine, or fowl antibodies.

An anti-FIAT antibody can be one in which the variable region, or a portion thereof, e.g., the CDRs, are generated in a non-human organism, e.g., a rat or mouse. The anti-FIAT polypeptide antibody can also be, for example, chimeric, CDR-grafted, or humanized antibodies. The anti-FIAT polypeptide antibody can also be generated in a non-human organism, e.g., a rat or mouse, and then modified, e.g., in the variable framework or constant region, to decrease antigenicity in a human.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against a FIAT polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies (or fragments thereof) that specifically bind to a FIAT polypeptide can be used, for example, to detect expression of FIAT in various tissues of a patient. For example, a FIAT polypeptide can be detected in conventional immunoassays of biological tissues or extracts. Examples of suitable assays include, without limitation, Western blotting, ELISAs, radioimmune assays, and the like.

III. Methods for Identifying Compounds Capable of Modulating FIAT Activity

The invention provides methods for identifying compounds, e.g., small organic or inorganic molecules (e.g., molecules having a molecular weight less than 1,000 Da), oligopeptides, oligonucleotides, or carbohydrates, capable of modulating (i.e., reducing or increasing) FIAT activity and, therefore, bone mass.

Libraries of Test Compounds

In certain embodiments, screens of the present invention utilize libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include peptides, peptidomimetics (e.g., peptoids), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp., San Diego, Calif. Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. *Acc. Chem. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of Hobbs DeWitt et al. (*Proc. Natl. Acad. Sci. USA* 90:6909 (1993)). Other synthesis methods, including the "tea-bag" technique of Houghten (see, e.g., Houghten et al., *Nature* 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., *J. Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening libraries of test compounds are described herein.

Screening Methods

The invention provides methods for identifying compounds capable of modulating FIAT activity. Although applicants do not intend to be bound by any particular theory as to the biological mechanism involved, such compounds are thought to modulate specifically (1) the function of a FIAT polypeptide (e.g., the ability to bind ATF4 polypeptides and/or to reduce (e.g., prevent) ATF4-mediated transcription and/or to modulate bone production) and/or (2) expression of the FIAT gene.

In certain aspects of the present invention, screening for such compounds is accomplished by (i) identifying from a group of test compounds those that bind to a FIAT polypeptide, modulate an interaction between FIAT and ATF4, and/or modulate (i.e., increase or decrease) transcription and/or translation of FIAT; and, optionally, (ii) further testing such compounds for their ability to modulate FIAT activity in vitro or in vivo. Test compounds that bind to FIAT, modulate an interaction between FIAT and ATF4, or modulate transcription and/or translation of FIAT, are referred to herein as "candidate compounds." Candidate compounds further tested and found to be capable of modulating in vivo the activity of a FIAT polypeptide and/or bone production are considered "FIAT modulating agents." In the screening methods of the present invention, candidate compounds can be, but do not necessarily have to be, tested to determine whether they are FIAT modulating agents. Assays of the present invention can be carried out in whole cell preparations and/or in ex vivo cell-free systems.

In one aspect, the invention includes methods for screening test compounds to identify compounds that bind to FIAT polypeptides. Binding of a test compound to a FIAT polypeptide can be detected, for example, in vitro by reversibly or irreversibly immobilizing the test compound(s) on a substrate, e.g., the surface of a well of a 96-well polystyrene microtiter plate. Methods for immobilizing polypeptides and other small molecules are well known in the art. For example, microtiter plates can be coated with a FIAT polypeptide by adding the polypeptide in a solution (typically, at a concentration of 0.05 to 1 mg/ml in a volume of 1-100 µl) to each well, and incubating the plates at room temperature to 37° C. for a given amount of time, e.g., for 0.1 to 36 hours. Polypeptides not bound to the plate can be removed by shaking excess solution from the plate, and then washing the plate (once or repeatedly) with water or a buffer. Typically, the polypeptide is in water or a buffer. The plate can then be washed with a buffer that lacks the bound polypeptide. To block the free protein-binding sites on the plates, plates can be blocked with a protein that is unrelated to the bound polypeptide. For example, 300 µl of bovine serum albumin (BSA) at a concentration of 2 mg/ml in Tris-HCl can be used. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate. Test compounds can then be added to the coated plate and allowed to bind to the FIAT polypeptide (e.g., at 37° C. for 0.5-12 hours). The plate can then be rinsed as described above.

Binding of FIAT to a second compound, e.g., the test compound described above or to an ATF4 polypeptide (discussed in further detail below), can be detected by any of a variety of art-known methods. For example, an antibody that specifically binds to a FIAT polypeptide (i.e., an anti-FIAT antibody, e.g., the polyclonal antibody described in the Examples section, below) can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds to the Fc portion of the anti-FIAT antibody). In an alternative detection method, the FIAT polypeptide is labeled (e.g., with a radioisotope, fluorophore, chromophore, or the like), and the label is detected. In still another method, a FIAT polypeptide is produced as a fusion protein with a protein that can be detected optically, e.g., green fluorescent protein (which can be detected under UV light). In an alternative method, the polypeptide is produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen, which can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various methods for identifying polypeptides (e.g., test polypeptides or ATF4 polypeptides) that bind to a FIAT polypeptide, the conventional two-hybrid assays of protein/ protein interactions can be used (see e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:876, 1995; Vidal et al., *Proc. Natl. Acad. Sci. USA*, 93:10315-10320, 1996; and White, *Proc. Natl. Acad. Sci. USA*, 93:10001-10003, 1996). Generally, two-hybrid methods involve reconstitution of two separable domains of a transcription factor. One fusion protein contains the FIAT polypeptide fused to either a transactivator domain or DNA binding domain of a transcription factor (e.g., of Gal4). The other fusion protein contains a test polypeptide (or ATF4 polypeptide) fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the FIAT polypeptide to the test polypeptide (or ATF4 polypeptide) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

In another aspect, the invention includes methods for screening test compounds to identify a compound that modulates a protein-protein interaction between a FIAT polypeptide and an ATF4 polypeptide. A method useful for high throughput screening of compounds capable of modulating protein-protein interactions between transcriptional regulators is described in Lepourcelet et al., Cancer Cell 5:91-102 (2004), which is incorporated herein by reference in its entirety. Typically, a first compound is provided. The first compound is a FIAT polypeptide or biologically active fragment thereof, or the first compound is an ATF4 polypeptide or biologically active fragment thereof. A second compound is provided which is different from the first compound and which is labeled. The second compound is a FIAT polypeptide or biologically active fragment thereof, or the second compound is a ATF4 polypeptide or biologically active fragment thereof. A test compound is provided. The first compound, second compound and test compound are contacted with each other. The amount of label bound to the first compound is then determined. A change in protein-protein interaction between the first compound and the second compound as assessed by label bound is indicative of the usefulness of the compound in modulating a protein-protein interaction between FIAT and the ATF4 polypeptide. In some embodiments, the change is assessed relative to the same reaction without addition of the test compound.

In certain embodiments, the first compound provided is attached to a solid support. Solid supports include, e.g., resins (e.g., agarose), beads, and multiwell plates. In certain embodiments, the method includes a washing step after the contacting step, so as to separate bound and unbound label.

In certain embodiments, a plurality of test compounds is contacted with the first compound and second compound. The different test compounds can be contacted with the other compounds in groups or separately. In certain embodiments, each of the test compounds is contacted with both the first compound and the second compound in separate wells. For example, the method can screen libraries of test compounds. Libraries of test compounds are discussed in detail above. Libraries can include, e.g., natural products, organic chemicals, peptides, and/or modified peptides, including, e.g., D-amino acids, unconventional amino acids, and N-substituted amino acids. Typically, the libraries are in a form compatible with screening in multiwell plates, e.g., 96-well plates. The assay is particularly useful for automated execution in a multiwell format in which many of the steps are controlled by computer and carried out by robotic equipment. The libraries can also be used in other formats, e.g., synthetic chemical libraries affixed to a solid support and available for release into microdroplets.

In certain embodiments, the first compound is a FIAT polypeptide or fragment thereof, and the second compound is an ATF4 polypeptide or fragment thereof. In other embodiments, the first compound is ATF4 polypeptide or fragment thereof, and the second compound is a FIAT polypeptide or fragment thereof. The solid support to which the first compound is attached can be, e.g., sepharose beads, SPA beads (microspheres that incorporate a scintillant) or a multiwell plate. SPA beads can be used when the assay is performed without a washing step, e.g., in a scintillation proximity assay. Sepharose beads can be used when the assay is performed with a washing step. The second compound can be labeled with any label that will allow its detection, e.g., a radiolabel, a fluorescent agent, biotin, a peptide tag, or an enzyme fragment. The second compound can also be radiolabeled, e.g., with $^{125}$I or $^3$H.

In certain embodiments, the enzymatic activity of an enzyme chemically conjugated to, or expressed as a fusion protein with, the first or second compound, is used to detect bound protein. A binding assay in which a standard immunological method is used to detect bound protein is also included. In certain other embodiments, the interaction of a FIAT polypeptide or fragment thereof and ATF4 or fragment thereof is detected by fluorescence resonance energy transfer (FRET) between a donor fluorophore covalently linked to FIAT (e.g., a fluorescent group chemically conjugated to FIAT, or a variant of green fluorescent protein (GFP) expressed as a FIAT-GFP chimeric protein) and an acceptor fluorophore covalently linked to a substrate protein, where there is suitable overlap of the donor emission spectrum and the acceptor excitation spectrum to give efficient nonradiative energy transfer when the fluorophores are brought into close proximity through the protein-protein interaction of FIAT and ATF4.

In other embodiments, the protein-protein interaction is detected by reconstituting domains of an enzyme, e.g., beta-galactosidase (see Rossi et al., Proc. Natl. Acad. Sci. USA 94:8405-8410 (1997)).

In still other embodiments, the protein-protein interaction is assessed by fluorescence ratio imaging (Bacskai et al., Science 260:222-226 (1993)) of suitable chimeric constructs of FIAT polypeptides and ATF4 polypeptides in cells, or by variants of the two-hybrid assay (Fearon et al., Proc. Natl. Acad. Sci. USA 89:7958-7962 (1992); Takacs et al., Proc. Natl. Acad. Sci. USA 90:10375-10379 (1993); Vidal et al., Proc. Natl. Acad. Sci. USA 93:10315-10320 (1996); Vidal et al., Proc. Natl. Acad. Sci. USA 93:10321-10326 (1996)) employing suitable constructs of FIAT and ATF4 polypeptides and tailored for a high throughput assay to detect compounds that inhibit the FIAT/ATF4 interaction. These embodiments have the advantage that the cell permeability of compounds that act as modulators in the assay is assured.

For example, in one assay, a FIAT polypeptide or fragment thereof is adsorbed to ELISA plates. The FIAT polypeptides are then exposed to test compounds, followed by a glutathione-S-transferase (GST)-ATF4 polypeptide fusion protein. Bound protein is detected with goat anti-GST antibody, alkaline phosphatase (AP)-coupled anti-goat IgG, and AP substrate. Compounds that interfere with protein-protein interactions yield reduced AP signals in the ELISA plates.

In still another aspect, the invention provides methods of identifying test compounds that modulate expression of a FIAT polypeptide. The method includes contacting a FIAT nucleic acid with a test compound and then measuring expression of the encoded FIAT polypeptide. In a related aspect, the invention features a method of identifying compounds that modulate the expression of FIAT polypeptides by measuring expression of a FIAT polypeptide in the presence of the test compound or after the addition of the test compound in: (a) a cell line into which has been incorporated a recombinant construct including the FIAT nucleic acid sequence or fragment or an allelic variation thereof; or (b) a cell population or cell line that naturally selectively expresses FIAT, and then measuring the activity of FIAT and/or the expression thereof.

Since the FIAT nucleic acids described herein have been identified, they can be cloned into various host cells (e.g., fungi, *E. coli*, or yeast) for carrying out such assays in whole cells.

In certain embodiments, an isolated nucleic acid molecule encoding a FIAT polypeptide is used to identify a compound that modulates (e.g., increases or decreases) the expression of FIAT in vivo (e.g., in a FIAT-producing cell). In such embodiments, cells that express FIAT are cultured, exposed to a test compound (or a mixture of test compounds), and the level of FIAT expression or activity is compared with the level of FIAT expression or activity in cells that are otherwise identical but that have not been exposed to the test compound(s). Standard quantitative assays of gene expression and FIAT activity can be used.

Expression of a FIAT polypeptide can be measured using art-known methods, for example, by Northern blot, PCR analysis, or RNAse protection analyses using a nucleic acid molecule of the invention as a probe. Other examples include enzyme-linked immunosorbent assay (ELISA), radioimmunoassay (RIA), and fluorescent activated cell sorting (FACS). The level of expression in the presence of the test molecule, compared with the level of expression in its absence, will indicate whether or not the test compound modulates the expression of FIAT.

In still another aspect, the invention provides methods of screening test compounds utilizing cell systems that are sensitive to perturbation to one or several transcriptional/translational components. In one embodiment, the cell system is a modified FIAT-expressing cell in which one or more of the transcriptional/translational components of the cell are present in an altered form or in a different amount compared with a corresponding wild-type FIAT-expressing cell. This method involves examining a test compound for its ability to perturb transcription/translation in such a modified cell.

In certain embodiments, the methods include identifying candidate compounds that interfere with steps in FIAT translational accuracy, such as maintaining a proper reading frame during translation and terminating translation at a stop codon. This method involves constructing cells in which a detectable reporter polypeptide can only be produced if the normal process of staying in one reading frame or of terminating translation at a stop codon has been disrupted. This method further involves contacting the cell with a test compound to examine whether it increases or decreases the production of the reporter polypeptide.

In other embodiments, the cell system is a cell-free extract and the method involves measuring transcription or translation in vitro. Conditions are selected so that transcription or translation of the reporter is increased or decreased by the addition of a transcription modifier or a translation modifier to the cell extract.

One method for identifying candidate compounds relies upon a transcription-responsive gene product. This method involves constructing a cell in which the production of a reporter molecule changes (i.e., increases or decreases) under conditions in which cell transcription of a FIAT nucleic acid changes (i.e., increases or decreases). Specifically, the reporter molecule is encoded by a nucleic acid transcriptionally linked to a sequence constructed and arranged to cause a relative change in the production of the reporter molecule when transcription of a FIAT nucleic acid changes. A gene sequence encoding the reporter may, for example, be fused to part or all of the gene encoding the transcription-responsive gene product and/or to part or all of the genetic elements that control the production of the gene product. Alternatively, the transcription-responsive gene product may stimulate transcription of the gene encoding the reporter, either directly or indirectly. The method further involves contacting the cell with a test compound, and determining whether the test compound increases or decreases the production of the reporter molecule in the cell.

Alternatively, the method for identifying candidate compounds can rely upon a translation-responsive gene product. This method involves constructing a cell in which cell translation of a FIAT nucleic acid changes (i.e., increases or decreases). Specifically, the reporter molecule is encoded by nucleic acid either translationally linked or transcriptionally linked to a sequence constructed and arranged to cause a relative increase or decrease in the production of the reporter molecule when transcription of a FIAT nucleic acid changes. A gene sequence encoding the reporter may, for example, be fused to part or all of the gene encoding the translation-responsive gene product and/or to part or all of the genetic elements that control the production of the gene product. Alternatively, the translation-responsive gene product may stimulate translation of the gene encoding the reporter, either directly or indirectly. The method further involves contacting the cell with a test compound, and determining whether the test compound increases or decreases the production of the first reporter molecule in the cell.

For these and any method described herein, a wide variety of reporters may be used, with typical reporters providing conveniently detectable signals (e.g., by spectroscopy). By way of example, a reporter gene may encode an enzyme that catalyses a reaction that alters light absorption properties.

Examples of reporter molecules include but are not limited to β-galactosidase, invertase, green fluorescent protein, luciferase, chloramphenicol acetyltransferase, beta-glucuronidase, exo-glucanase and glucoamylase. Alternatively, radiolabeled or fluorescently-labeled nucleotides can be incorporated into nascent transcripts that are then identified when bound to oligonucleotide probes. For example, the production of the reporter molecule can be measured by the enzymatic activity of the reporter gene product, such as β-galactosidase.

Any of the methods described herein can be used for high throughput screening of numerous test compounds to identify candidate compounds. High-throughput screening methods are those that can be used to screen a large number of candidate compounds relatively easily and quickly.

Having identified a test compound as a candidate compound, the candidate compound can be further tested to confirm whether it is a FIAT modulating agent, i.e., to determine whether it can modulate FIAT activity and/or bone formation in vitro and/or in vivo (e.g., using an animal, e.g., rodent, model system). Using other, art-known variations of such methods, one can test the ability of a nucleic acid (e.g., DNA or RNA) used as the test compound to bind FIAT polypeptides or nucleic acids.

In vitro testing of a candidate compound can be accomplished by means known to those in the art, such as assays involving the use of osteoblasts, e.g., wild type osteoblasts and/or transgenic osteoblasts. Exemplary assays for monitoring osteoblast activity, as well as a useful transgenic osteoblast that can be used in such assays, are described in the Examples section, below. For example, such an assay might be carried out as follows: osteoblastic cells (wild type or transgenic) are plated at $10^6$ cells per well in a 6-well plate and grown in αMEM containing 10% FBS, 2% Glutamax, 1% penicillin, 1% streptomycin, 1% Fungizone, 50 μg/ml ascorbic acid, 10 mM β-glycerol phosphate, and $10^{-8}$ M dexamethasone. After 7 days in culture, cells are assayed for alkaline phosphatase activity, e.g., after the cells are fixed by 4% paraformaldehyde (PFA) and lysed. One mg/ml 4-nitrophenyl phosphate (Sigma) is added to each well and incubated for 30 minutes before reading at 405 nm. Protein concentration in cell lysate is determined, e.g., by the Bradford assay. Alkaline phosphatase concentration is expressed as relative activity (absorbance at 405 nm) per mg protein per well. Alternatively, osteocalcin gene expression can be monitored using techniques (e.g., Northern blotting, RT-PCR, and the like) and probes known to those skilled in the art. In still another assay, mineralization is monitored by staining with alizarin red after 14 days in culture. Briefly, cells are fixed with 4% PFA and stained with 0.5% alizarin red (Sigma) at pH 5.0. Dark red mineralized nodules can be counted and mineralization expressed as number of nodules per square millimeter.

Alternatively or in addition, in vivo testing of candidate compounds can be performed by means known to those in the art. For example, the candidate compound(s) can be administered to a mammal, such as a rodent (e.g., murine) or rabbit. Such animal model systems are art-accepted for testing potential pharmaceutical agents to determine their therapeutic efficacy in patients, e.g., human patients. Animals that are particularly useful for in vivo testing are wild type animals or non-wild type animals (e.g., mice) that over-produce FIAT polypeptides, e.g., animals that overexpresses a FIAT transgene, or that display reduced production of FIAT polypeptides (e.g., FIAT −/− animals). A transgenic mouse that over-expresses a FIAT transgene is described in the Examples section, below. Other animals that are useful for in vivo testing are animals that over-produce ATF4 polypeptides, e.g., animals that overexpresses an ATF4 transgene, or that display reduced production of ATF4 polypeptides (e.g., ATF4 −/− animals). In a typical in vivo assay, an animal (e.g., a wild type or transgenic mouse) is administered, by any route deemed appropriate (e.g., by injection), a dose of a candidate compound. Conventional methods and criteria can then be used to monitor animals for signs of modulation of FIAT activity, e.g., signs of increased or decreased bone formation. If needed, the results obtained in the presence of the candidate compound can be compared with results in control animals that are not treated with the test compound.

Medicinal Chemistry

Once a compound (or agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al. (1988) *J. Antibiot.* 41: 1430-8. Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

IV. Pharmaceutical Compositions

The compounds and agents, nucleic acids, polypeptides, and antibodies (all of which can be referred to herein as "active compounds"), can be incorporated into pharmaceutical compositions. Such compositions typically include the active compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™ EL (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent which delays absorption, e.g., aluminum monostearate and gelatin in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, to reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For the compounds described herein, an effective amount, e.g. of a protein or polypeptide (i.e., an effective dosage), ranges from about 0.001 to 30 mg/kg body weight, e.g. about 0.01 to 25 mg/kg body weight, e.g. about 0.1 to 20 mg/kg body weight. The protein or polypeptide can be administered one time per week for between about 1 to 10 weeks, e.g., between 2 to 8 weeks, about 3 to 7 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a protein, polypeptide, antibody, or other compound can include a single treatment or, preferably, can include a series of treatments.

For antibodies, a useful dosage is about 5 mg/kg of body weight (e.g., 3 mg/kg to 20 mg/kg). Generally, partially human antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described by Cruikshank et al. ((1997) *J. Acquired Immune Deficiency Syndromes and Human Retrovirology* 14:193).

If the compound is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules (e.g., FIAT DNA) of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Conditions Associated with Inappropriate Bone Formation and Treatments therefor A variety of conditions have been linked to inappropriate or unregulated bone formation and patients suffering from or at risk for such conditions can be treated according to the methods of the present invention. Conditions linked to excessive bone formation include, but are not limited to acromegaly, gigantism, multiple osteocartilaginous exostoses, and non-syndromic high bone mass disease (e.g., gain-of-function mutation in LRP5 receptor, Boyden et al., 2002, NEJM 346: 1513-21). Conditions associated with insufficient bone formation include, but are not limited to, dwarfism, cleidocranial dysplasia, osteoporosis, e.g., postmenopausal osteoporosis, corticosteroid-induced osteoporosis, senile osteoporosis, vitamin D-deficiency-related osteoporosis, idiopathic juvenile osteoporosis, immobilization- and weightlessness-induced bone loss, renal failure, and osteoporosis-pseudoglioma (e.g., loss-of-function mutation in LRP5 receptor, Gong et al., 2001, Cell 107: 513-23)

Other conditions that involve bone formation can also be treated according to the present invention. Such conditions include, but are not limited to, craniofacial-skeletal discrepancies, bone damage resulting from traumatic injury (e.g., bone fractures), osteoarthritis, rheumatoid arthritis, failed arthrodesis, dyschondroplasia, achondroplasia, or congenital pseudoarthrosis. Examples of "bone fractures" include, but are not limited to, nonunion, delayed union, pathological fractures, and those caused by surgery.

The term "patient" is used throughout the specification to describe an animal, human or non-human, rodent or non-rodent, to whom treatment according to the methods of the present invention is provided. Veterinary and non-veterinary applications are contemplated. The term includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Typical patients include humans, farm animals, and domestic pets such as cats and dogs.

One strategy for treating patients suffering from or at risk for conditions that involve bone formation is to modulate FIAT activity and, therefore, the formation of bone, in the patient. The goal is to normalize bone formation, e.g., to increase formation where formation is too low and to decrease formation where formation is too high. Modulation of FIAT activity falls into two basic categories: decreasing (i.e., reducing or eliminating) FIAT activity and increasing (i.e., supplementing or providing) FIAT activity where there is insufficient or no activity. Whether FIAT activity should be inhibited or increased depends upon the intended application. FIAT activity can be modulated using the active compounds (e.g., candidate compounds and/or FIAT modulating agents) described herein. Compounds that increase FIAT activity can be used, e.g., as treatments for conditions linked to excessive bone formation. Compounds that decrease activity can be used, e.g., as treatments for conditions linked to insufficient bone formation or, e.g., to enhance bone formation in patients suffering from a bone fracture.

Decreasing FIAT Activity

Art-known methods for decreasing the expression of a particular protein in a patient can be modified as described herein to decrease FIAT activity. For example, an antisense nucleic acid effective to inhibit expression of an endogenous FIAT gene can be utilized. As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide that hybridizes under physiological conditions to DNA comprising a particular gene or to an mRNA transcript of that gene and, thereby, inhibits the transcription of that gene and/or the translation of that mRNA.

Antisense molecules are designed so as to interfere with transcription or translation of a target gene upon hybridization with the target gene or transcript. The antisense nucleic acid can include a nucleotide sequence complementary to an entire FIAT RNA or only a portion of the RNA. On one hand, the antisense nucleic acid needs to be long enough to hybridize effectively with FIAT RNA. Therefore, the minimum length is approximately 12 to 25 nucleotides. On the other hand, as length increases beyond about 150 nucleotides, effectiveness at inhibiting translation may increase only marginally, while difficulty in introducing the antisense nucleic acid into target cells may increase significantly. Accordingly, an appropriate length for the antisense nucleic acid may be from about 15 to about 150 nucleotides, e.g., 20, 25, 30, 35, 40, 45, 50, 60, 70, or 80 nucleotides. The antisense nucleic acid can be complementary to a coding region of FIAT mRNA or a 5' or 3' non-coding region of a FIAT mRNA, or both. One approach is to design the antisense nucleic acid to be complementary to a region on both sides of the translation start site of the FIAT mRNA. Antisense nucleic acids are described in greater detail herein.

Similarly, RNA interference (RNAi) techniques can be used to inhibit FIAT activity, in addition or as an alternative to, the use of antisense techniques. For example, small interfering RNA (siRNA) duplexes directed against FIAT nucleic acids could be synthesized and used to prevent expression of the encoded protein(s). Nucleic acids useful for RNAi are described in greater detail herein.

Another approach to inhibiting FIAT activity involves administering to a patient a candidate compound or FIAT modulating agent that binds to (e.g., blocks) FIAT polypeptides and prevents them from interacting with a target protein (e.g., ATF4). With respect to FIAT and its interaction with ATF4, such compounds and agents may, for example, bind to the FIAT polypeptide (e.g., to the leucine zipper of the FIAT polypeptide) and/or to the ATF4 polypeptide (e.g., to the leucine zipper of the ATF4 polypeptide) and prevent interaction (e.g., binding) between these two polypeptides. Such candidate compounds and FIAT modulating agents can be identified using screening methods described herein. An example of a compound that can bind to a FIAT polypeptide and, therefore, can be used to reduce FIAT activity, is an ATF4 polypeptide (e.g., the ATF4 polypeptide as set forth in SEQ ID NO:6) or a FIAT polypeptide-binding fragment thereof. Exemplary ATF4 polypeptides, and nucleic acids that encode them, are described herein, particularly in the Examples section, below.

Increasing FIAT Activity

New or supplemental FIAT activity can be provided in vivo by direct administration of a naturally occurring and/or recombinant FIAT polypeptide to a patient. FIAT polypeptides that can be used to supplement FIAT activity, e.g., in humans, are described herein, e.g., SEQ ID NO:2, or fragments thereof. Other exemplary FIAT polypeptides are described in the Example section, below. Such polypeptides can be used in modified or unmodified form. Examples of typical modifications are derivation of amino acid side chains, glycosylation, conservative amino acid substitutions, and chemical conjugation or fusion to other, non-FIAT polypeptide moieties.

Alternatively or in addition, a FIAT polypeptide can be generated directly within an organism, e.g., a human, by expressing within the cells of the organism a nucleic acid construct containing a nucleotide sequence encoding a FIAT polypeptide. Any appropriate expression vector suitable for transfecting the cells of the organism of interest can be used for such purposes. The nucleic acid construct can be derived from a non-replicating linear or circular DNA or RNA vector, or from an autonomously replicating plasmid or viral vector. Methods for constructing suitable expression vectors are known in the art, and useful materials are commercially available. Exemplary expression vectors that encode a FIAT polypeptide are described in the Examples section, below.

Expression vectors can be introduced to cells by any method known in the art, e.g., lipofection, chemical methods (e.g., using calcium phosphate or DEAE-dextran), electroporation, or biolistics (gene gun). Viral vectors can be introduced by the above methods or by infection of the cells with viral particles.

VI. Transgenic Animals

The present invention also features transgenic animals that express FIAT polypeptides. Such animals represent model systems for the study of disorders that are caused by or exacerbated by overexpression or underexpression of FIAT polypeptides and for the development of therapeutic agents that modulate the expression or activity of FIAT. For example, dominant-negative and constitutively activated alleles could be expressed in mice to establish physiological function.

Transgenic animals can be, for example, farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats). A "transgene" is exogenous DNA that is integrated into the genome of a cell from which a transgenic animal develops and which remains in the genome of the mature animal, thereby directing the expression of an encoded gene product in one or more cell types or tissues of the transgenic animal. A transgene can also be created to remove or disrupt the expression of an endogenous gene.

Any technique known in the art can be modified as described herein to introduce a FIAT transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci. USA* 82:6148, 1985); gene targeting into embryonic stem cells (Thompson et al., *Cell* 56:313, 1989); and electroporation of embryos (Lo, *Mol. Cell. Biol.* 3:1803, 1983). Especially useful are the methods described in Yang et al. (*Proc. Natl. Acad. Sci. USA* 94:3004-3009, 1997). Construction of a transgenic animal that overexpresses a FIAT transgene is described below in the Examples section.

The present invention provides for transgenic animals that carry the FIAT transgene in all their cells, as well as animals that carry the transgene in some, but not all, of their cells. That is, the invention provides for mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that the FIAT transgene be integrated into the chromosomal site of the endogenous FIAT gene, gene targeting is preferred. Briefly, when such a technique is to be used, vectors containing some nucleotide sequences homologous to an endogenous FIAT gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous FIAT gene in only that cell type (Gu et al., *Science* 265:103, 1984). The regulatory sequences required for such a cell-type specific inactivation will depend upon the particular cell type of interest, and will be apparent to those of skill in the art. These techniques are useful for preparing "knock outs" having no functional FIAT gene.

Once transgenic animals have been generated, the expression of the recombinant FIAT gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of FIAT gene-expressing tissue can also be evaluated immunocytochemically using antibodies specific for wild type FIAT or the FIAT transgene product.

For a review of techniques that can be used to generate and assess transgenic animals, skilled artisans can consult Gordon (*Intl. Rev. Cytol.* 115:171-229, 1989), and may obtain additional guidance from, for example: Hogan et al. *Manipulating the Mouse Embryo*, Cold Spring Harbor Press, Cold Spring Harbor, N.Y., 1986); Krimpenfort et al. (*Bio/Technology* 9:86, 1991), Palmiter et al. (Cell 41:343, 1985), Kraemer et al. (*Genetic Manipulation of the Early Mammalian Embryo*, Cold Spring Harbor Press, Cold Spring Harbor, N.Y., 1985), Hammer et al. (*Nature* 315:680, 1985), Purcel et al. (*Science*, 244:1281, 1986), Wagner et al. (U.S. Pat. No. 5,175,385), and Krimpenfort et al. (U.S. Pat. No. 5,175,384).

EXAMPLES

The invention is illustrated in part by the following example, which is not to be taken as limiting the invention in any way.

Materials and Methods

Yeast Two-hybrid cDNA libraries from osteoblastic MC3T3-E1 cells or cultured primary osteoblasts were prepared in the pAD-GAL4 vector (Stratagene Cloning Systems, LaJolla, Calif.) using the HYBRIZAP® Two-Hybrid cDNA Gigapack cloning kit and following the manufacturer's instruction (Stratagene). The FIAT bait was prepared by subcloning the cDNA into the GAL4-DBD expression plasmid (Stratagene). The screen was performed according to the manufacturer's protocols and interaction between molecules was identified in yeast that were grown in selective medium lacking the essential nutrients tryptophan, leucine, and uracil.

Western Blotting, Immunocytochemistry, and Coimmunoprecipitation

A peptide corresponding to FIAT residues 111-125 of SEQ ID NO:2 was synthesized, coupled to ovalbumin, and used to raise rabbit polyclonal antibodies following standard protocols. The polyclonal antisera (1:1500 dilution) was used to probe immunoblots of nuclear extracts from osteoblastic MC3T3-E1 cells. Anti-rabbit antibodies conjugated with horseradish peroxidase (1:25,000 dilution) were used as secondary antibodies and detected by ECL™ Western Blotting Detection Reagents (Amersham). The antibody was also used for indirect immunofluorescence. Primary cultures of osteoblasts were obtained from 6-8 days old calvaria. Briefly, calvaria were minced and digested sequentially (5×10 minutes) with αMEM containing 0.2% collagen D (Roche) and 0.1% hyaluronidase (Roche). Fractions 3 to 5 were collected and plated in a 6-well plate with αMEM containing 10% FBS, 2% Glutamax, 1% penicillin, 1% streptomycin, and 1% Fungizone™ (Invitrogen). Cells were allowed to attach for seven days and were cultured in the presence of $10^{-8}$ M dexamethasone (Porter et al., 2003, J. Cell. Biochem. 90:13-22; Yang et al., 2003, Chinese Med. J. 116:1357-60). The primary osteoblasts were fixed in 4% paraformaldehyde and permeabilized with 0.2% Triton® X-100. Following blocking with 1% Blocking Reagent (Roche Molecular Diagnostics) supplemented with 0.2% Tween®-20, the cells were incubated with the anti-FIAT antibody (1:200). The cells were then incubated for 1-2 hours at room temperature with a rhodamine-conjugated anti-rabbit IgG secondary antibody (dilution 1:500) to detect endogenous FIAT protein. Coverslips were mounted in Vectashield™ (with DAPI) mounting medium (Vector Laboratories).

For co-immunoprecipitation, 100-200 μg of nuclear proteins from ROS 17/2.8 osteoblastic cells in buffer D (20 mM HEPES-KOH, pH 7.9, 25% glycerol, 150 mM NaCl, 1.5 mM $MgCl_2$, 0.2 mM EDTA with inhibitors of proteases: 5 μg/ml leupeptin, aprotinin, pepstatin A, and 1 mM PMSF) were pre-cleared with 50 μl of protein A-Sepharose® slurry (Amersham) for 1 hour at 4° C. with gentle rocking. Following centrifugation, the cleared extract was incubated overnight at 4° C. with gentle rocking, with or without 1-2 μg of specific or unrelated antibody and 50 μl of protein A-Sepharose® slurry. The precipitates were washed with hypotonic buffer (10 mM HEPES-KOH, pH 7.9, 1.5 mM $MgCl_2$, 10 mM KCl, and protease inhibitors as above) and resuspended in 25 μl of PBS. A 10 μl aliquot was mixed with SDS-sample buffer, separated on 12% SDS-PAGE, transferred to PVDF, and the blots were probed with anti-ATF4 antibodies (Santa Cruz Biotechnology, Santa Cruz, Calif.) or anti-FIAT antiserum, then with anti-rabbit secondary antibody conjugated to horseradish peroxidase. Proteins were detected by chemiluminescence with ECL™ Plus Western Blotting Detection Reagents (Amersham).

Transfection Experiments

COS-7 or MC3T3-E1 cells were plated at $1.5 \times 10^5$ cells/well in a 6-well plate and transfected with 400 ng of the ATF sites reporter (Liang and Hai, 1997, J. Biol. Chem. 272: 24088-95) or 1 µg of the OSE1-luc reporter (Ducy and Karsenty, 1995, Mol. Cell. Biol. 15:1858-69), 400 ng of pCMV5ATF4, 25 ng of pK3HRSK2, 400 or 800 ng of pcDNA3.1/V5-HIS-TOPOFIAT, 50 ng of $pSV_6TKCAT$, and varying amount of pBluescript™ reporter vectors using Lipofectamine™ (Invitrogen Life Technologies, Burlington, Ontario) reagents according to manufacturer's instructions. Luciferase assay and chloramphenicol acetyltransferase ELISA (Roche Applied Science, Laval, Quebec) were performed 24 hrs after transfection following the manufacturer's protocol. Data represent ratios of luciferase/chloramphenicol transferase activity and values are means of 3 independent transfection experiments performed in duplicate.

Electrophoretic Mobility Shift Assays (EMSAs)

Complementary oligonucleotides corresponding to the OSE1 binding site within the murine osteocalcin proximal promoter region (5'-CCTGCT CCTCCTGCTTACATCAGAGA-3') (SEQ ID NO:9) were synthesized with an overhang, annealed, and labeled with [$^{32}$P]-labeled dNTPs by Klenow fill-in using standard protocols (Ausubel et al., supra).

The recombinant FIAT protein was purified using the IMPACT™ system (New England Biolabs, Beverly, Mass.) as described previously (Quelo et al., 2002, Gene Expr. 10:255-62). ROS17/2.8 nuclear extracts were prepared following the technique of Andrews and Faller (1991, Nucleic Acids Res. 19:2499).

Recombinant protein (300 or 600 ng) or nuclear extracts (10 µg) were incubated for 30 minutes at 4° C. in 20 µl of binding buffer (20 mM HEPES, pH 7.9, 60 mM KCl, 1 mM DTT, 1 mM EDTA, 100 ng of polydI-dC, 12% Glycerol). Labeled probe (10,000 dpm) was added to the binding reaction mixture. For supershift assays, anti-ATF4 or unrelated antibody (2-4 µg; Santa Cruz Biotechnology, Santa Cruz, Calif.) was added to the binding reaction for 30 minutes prior to the addition of the labeled probe. The bound mixtures were separated on a non-denaturing 5% polyacrylamide gel at 160 V for 100 minutes in 0.5×TBE (Tris-Borate-EDTA) buffer. The gel was subsequently dried and subjected to autoradiography.

Generation of FIAT Transgenic Mice

FIAT transgenic mice were generated using a pCI (Promega, Nepean, Ontario)-based vector containing the osteoblast-specific 2.3 kb α1(I)collagen promoter (Rossert et al., 1995, J. Cell Biol. 129:1421-32), an SV40 small intron, the 1.8 kb full length FIAT cDNA, and the 240 bp SV40 polyadenylation signal. The linearized construct was injected at 1 µg/mL into fertilized eggs using standard methodology (Hogan et al. *Manipulating the Mouse Embryo*, Cold Spring Harbor Press, Cold Spring Harbor, N.Y., 1994). Founder animals containing the transgene were detected by Southern blot. Tissue specificity of transgene expression was examined by RT-PCR. The transgenic line was maintained by crossing with wild type C57BL/6 mice and genotyped by PCR using FIAT primers (5'-ATCCATCAAAGCGCCATCAAAGCG-3' (SEQ ID NO:10) and 5'-ACAAATAAAGCAATAGCATCA-CAA-3' (SEQ ID NO:11)) and glyceraldehyde-3-phosphate dehydrogenase (Gapdh) primers (5'-CACCATGGAGAAG-GCCGGG-3' (SEQ ID NO:12) and 5'-GACGGACACAT-TGGGGGTAG-3' (SEQ ID NO:13)). Mice were sacrificed and analyzed at 3 months of age. Demeclocycline (Sigma-Aldrich, Canada) was injected at 30 ng/g of mice twice at 5 days intervals before sacrifice. At least 10 animals of each genotype were used for all experiments, and statistical significance was assessed by Student's t-test. Error bars represent standard errors of the means (SEM). All animal experimentation was approved by the Institutional Animal Care and Use Committee.

Reverse Transcription-PCR

RNA from primary osteoblasts or 3 months old calvaria was extracted with TRIzol™ (Invitrogen) following the manufacturer's instructions. Five µg of RNA were reverse transcribed into cDNA with 500 ng random primers, 25 mM dNTPs, 5 µl of 0.1 M DTT, 10 µl 5× First Strand Buffer, 3.5 µl RNAguard™ (Roche), and 2 µM-MLV Reverse Transcriptase (Promega). Endogenous or transgenic Fiat and Gapdh genes were amplified by PCR using the primers described above.

Morphological Analysis

Bone mineral density was determined by Dual Energy X-ray Absorptiometry (DEXA) and data were analyzed by Lunar PIXImus software before mice were sacrificed. Bone samples were fixed in 4% paraformaldehyde (PFA), either embedded in methyl methacrylate, or decalcified and embedded in paraffin for future studies. For histological analysis, methyl methacrylate embedded tibiae sections (5 µm) were stained with Goldner, Toluidine Blue and von Kossa reagents. Histomorphometric measurements were performed using BioQuant Nova Prime (BioQuant Image Analysis Corporation, Nashville, Tenn.) software. Femurs preserved in PBS were first scanned with microcomputerized tomography (MicroCT) before performing 3-point bending test at the Centre for Bone and Periodontal Research of McGill University.

Osteoblast Proliferation and Apoptosis Experiments

De-mineralized paraffin embedded calvarial sections (6 µm) were used for all immunohistochemical experiments. Proliferation rate of osteoblasts was determined by the Proliferating Cell Nuclear Antigen (PCNA) Staining Kit (Zymed Laboratories Inc., Markham, Ontario) following the manufacturer's instructions. Sections were counterstained with DAPI (Vector Laboratories, Burlington, Ontario), and values were expressed as the number of proliferating osteoblasts over the number of DAPI positive cells. Apoptotic rate of osteoblasts was assessed using the TdT-mediated dUTP-biotin end labeling (TUNEL)-based in situ Cell Death Detection Kit, POD (Roche) followed by staining with diaminobenzene (DAB) substrate (Vector). Experiments were performed according to the manufacturers' instructions except that sections were unmasked with 0.1% trypsin and counterstained with methyl green.

Colorimetric Determination of Alkaline Phosphatase and Alizarin Red Staining

Primary cultures of osteoblasts were obtained from 6-8 days old calvaria or 3 months old bone marrow stromal cells. Osteoblasts from calvaria were prepared as described above. For osteoblasts from bone marrow stromal cells, epiphysis from both ends of femurs were cut off. Bone marrow cells were flushed out with a 22 gauge needle with the previous medium, resuspended, and plated at $10^6$ cells per well in a 6-well plate. After cell attachment on day 4, medium was changed every 3 days provided with additional 50 µg/ml ascorbic acid (Franceschi and Iyer, 1992, J. Bone Mineral Res. 7:235-246), 10 mM β-glycerophosphate (Quarles et al., 1992, J. Bone Mineral Res. 7:683-92), and $10^{-8}$ M dexamethasone (Porter et al., 2003, J. Cell. Biochem. 90:13-22;

Yang et al., 2004, Cell 117:387-98). Cells were assayed for alkaline phosphatase level after 7 days, or stained with alizarin red after 14 days. Cells were trypsinized with 0.05% trypsin-EDTA, and plated at $5 \times 10^4$ cells/well in two 12-well plates separately. For colorimetric determination of alkaline phosphatase level, cells were fixed by 4% PFA and lysed. One mg/mL 4-nitrophenyl phosphate (Sigma) was added to each well and incubated for 30 minutes before reading at 405 nm. Protein concentration in cell lysate was determined by the Bradford assay. Alkaline phosphatase concentration was normalized by protein concentration per well. For alizarin red staining, cells were fixed with 4% PFA and stained with 0.5% alizarin red (Sigma) at pH 5.0. Dark red mineralized nodules were expressed per square millimeter, and cells were photographed with bright-field microscopy.

Real Time Reverse Transcription-PCR

RNA from 3 months old calvaria was extracted with TRIzol™ (Invitrogen) following the manufacturer's instructions. Five μg of RNA were reverse transcribed into cDNA using the High Capacity cDNA Archive kit as per manufacturer's recommendations (Applied Biosystems, Foster City, Calif.). Real Time PCR amplification was performed on an Applied Biosystems 7700 instrument using specific TaqMan™ assays for Osteocalcin (OCN), Fiat, Atf4, Runx2/Cbfa1, Osterix (Osx), Bone Sialoprotein (Bsp) or type I collagen (col1A1) and the TaqMan™ Universal PCR Master Mix (Applied Biosystems). Expression level of each mRNA was quantified by the relative standard curve method (User bulletin #2, ABI Prism 7700 Sequence Detection System) and normalized to Gapdh levels.

van Gieson Staining

The van Gieson stain was prepared by dissolving 0.5 g of Sirius Red F3B (Direct Red, Sigma) in 500 ml of saturated picric acid in water. De-paraffinized, re-hydrated sections were stained for 1 hour in van Gieson stain, rinsed in 0.5% acetic acid, dehydrated in three changes of 100% ethanol, cleared in xylene, and mounted.

Analysis of Collagen Content and Synthesis

The collagen content of bones was analyzed as hydroxyproline content by the method of Burleigh et al. (1974, Biochem. J. 137:387-98). Briefly, demineralized tibial bone (typically 2-5 mg) was hydrolyzed in 6 M HCl (40 μl/mg) at 110° C. for 20 hours. A 35 μl aliquot of the digest was neutralized by the addition of 35 μl 6 M NaOH, and the solution was then diluted by the addition of 1 ml of water and clarified by the addition of activated charcoal resin. After centrifugation, a 20 μl aliquot of the supernatant was analyzed for hydroxyproline content following treatment with chloramine T reagent and color development with dimethylaminobenzaldehyde. Absorbance was measured at 560 nm and compared to hydroxyproline standards (0.1-5 μg in 20 μl). Collagen synthesis by osteoblasts was determined following the technique described by Yang et al. (2004, Cell 117:387-98) with the following modifications: wild-type and FIAT-transgenic primary osteoblasts were labeled for 12 hours with 50 μCi/ml of [$^3$H] proline (Amersham) in high-glucose DMEM (GIBCO) supplemented with 2% dialyzed FBS, 2 mM Glutamax™ (GIBCO), and 55 μM β-mercaptoethanol, in the presence or absence of non-essential amino acids mix. Cells were homogenized in 500 μl of PBS with protease inhibitors (5 μg/ml leupeptin, aprotinin, pepstatin A, and 1 mM PMSF). Fifty microliters were used for protein quantification using the Bradford assay. An additional fraction (200 μl) served for β-actin determination by Western blotting. The remaining 250 μl of cell homogenate were digested to collagen with 50 μg/ml of pepsin, precipitated, and resolved by SDS-PAGE on a 7% gel with 2M urea as described (Yang et al., 2004, Cell 117:387-98). The wet gels were soaked in amplifying reagent (Amplify™; Amersham), dried, and exposed to Hyperfilm™ MP (Amersham). The intensity of the signal was quantified using the GeneTools™ software (v. 2.11.03; Syngene USA, Frederick, Md.) and normalized to β-actin expression.

Example 1

FIAT Interacts with ATF4

The full-length 1.8 kb FIAT cDNA translates into a 66 kDa protein that localizes to the nucleus in calvarial osteoblasts (FIGS. 3A-3C) and in ROS 17/2.8 osteoblastic cells (Majeska et al., 1980, Endocrinol. 107:1494-503). The human FIAT protein (accession number NP_060830 (SEQ ID NO:2), encoded by a gene mapping to chromosome p22.1, accession number NM_018360 (SEQ ID NO:1)) is predicted to form a long coiled-coil at its C-terminus, a structure that favors protein-protein interactions. Moreover, computer modeling predicts the presence of putative leucine zippers within the FIAT protein (FIG. 1B). The FIAT mRNA is around 4.5 kb in length with an extended 3'-untranslated region and is ubiquitously expressed (Nogami et al., 2004, Biochem. Biophys. Res. Commun. 319:936-43).

Figure 4B:
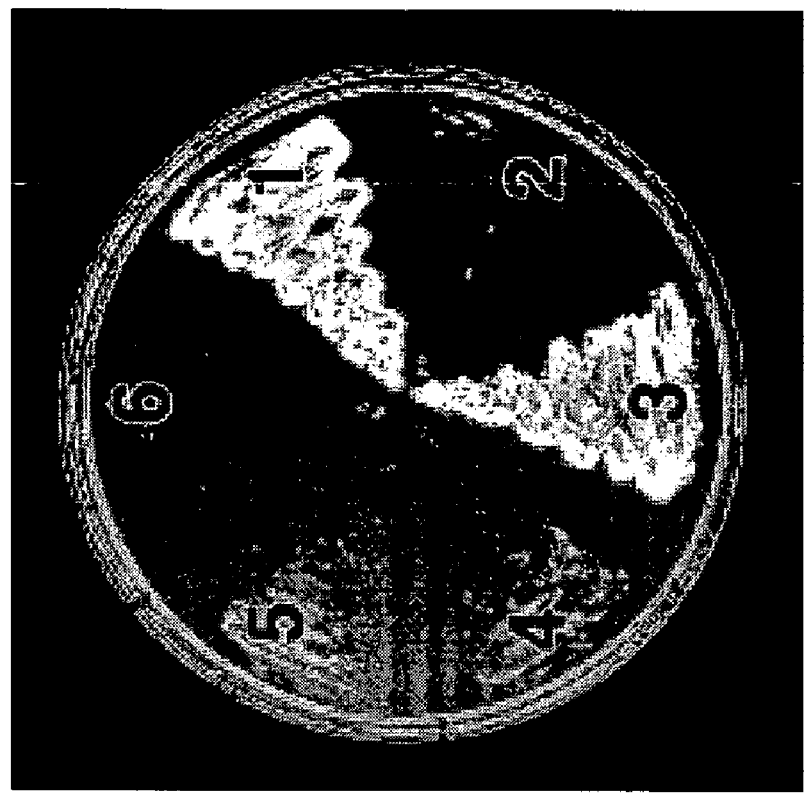
FIGS. 4A-4B are pictures of growth plates used in yeast two-hybrid protein interaction assays.
Figure 4A:
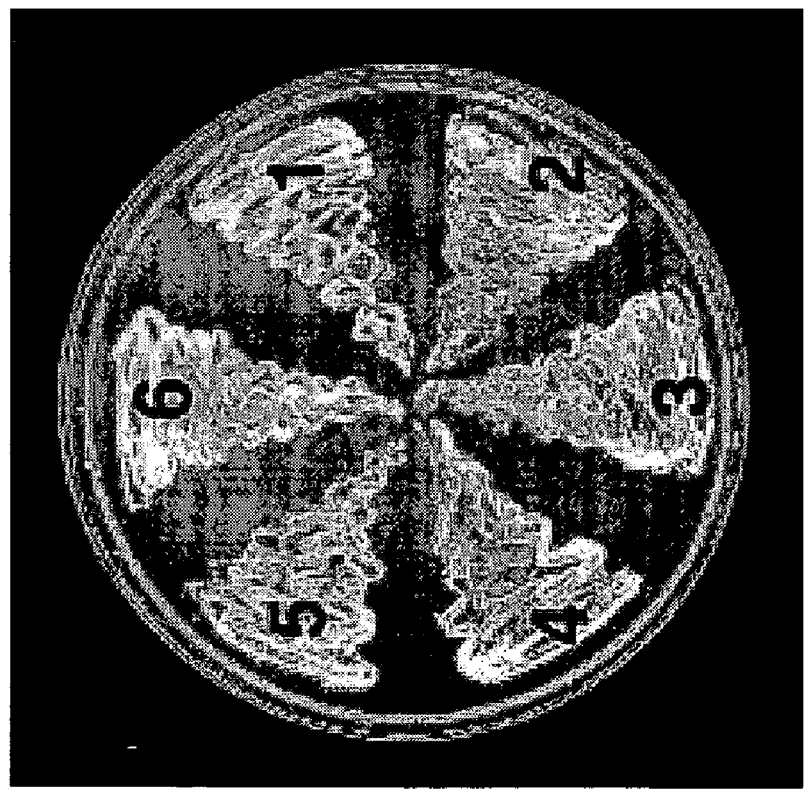

The presence of a putative leucine zipper within the FIAT protein sequence (FIG. 1B) prompted an investigation as to whether FIAT could form homodimeric or heterodimeric interactions. Yeast two-hybrid assays using FIAT as both the bait and target molecules revealed that FIAT could not detectably homodimerize (FIGS. 4A-4B). In a search for putative heterodimerization partners, FIAT was used as bait to screen cDNA libraries from MC3T3-E1 osteoblastic cells (Sudo et al., 1983, J. Cell Biol. 96:191-8) or primary cultures of osteoblasts (Ecarot-Charrier et al., 1983, J. Cell Biol. 96:639-43) in the two-hybrid assay. Three independent clones encoding the ATF4 transcription factor were isolated from the MC3T3-E1 library, while two different clones were obtained from the primary osteoblasts library, thus identifying ATF4 as a target molecule (FIGS. 4A-4B). Position 1: FIAT 'bait'+ATF4 'target'; position 2: negative control; position 3: positive control; position 4: FIAT 'bait'+FIAT 'target' without leucine zipper; position 5: FIAT 'bait'+FIAT 'target'; position 6: negative control. Note that on three-minus selection media, only yeasts at position 1 (FIAT+ATF4) and position 3 (positive control) grow, demonstrating a positive interaction between FIAT and ATF4.

Figures 4C, 4D:
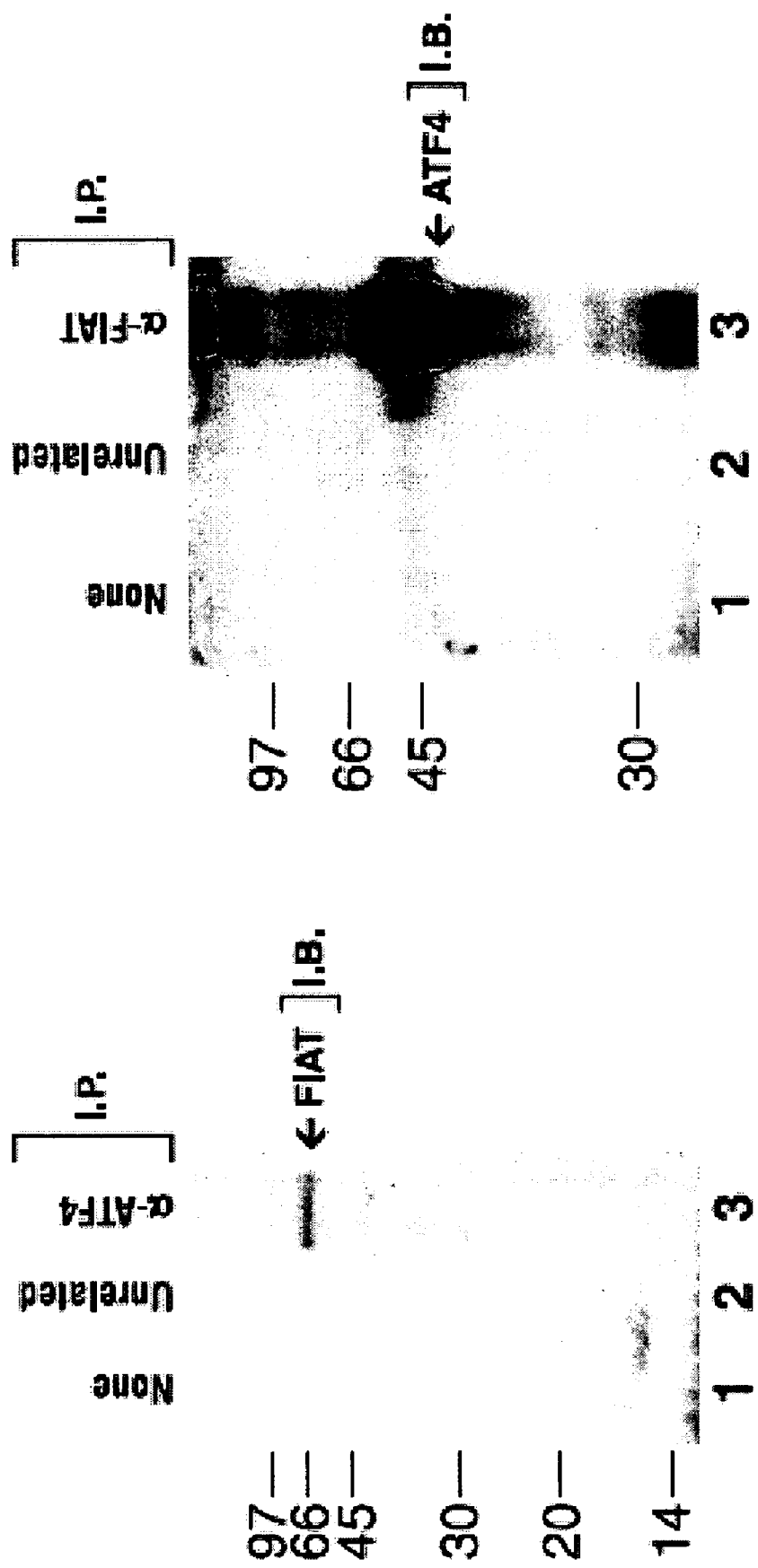
FIG. 4C-4D are reproductions of immunoblots depicting the results of co-immunoprecipitation against FIAT or ATF4.

To confirm this interaction, reciprocal co-immunoprecipitation assays were performed using ROS 17/2.8 osteoblastic cells. Immunoprecipitation of endogenous ATF4 co-precipitated endogenous FIAT (FIG. 4C). Reciprocally, the ATF4 protein co-immunoprecipitated with endogenous FIAT (FIG. 4C). The use of unrelated antibodies or protein A Sepharose® alone confirmed the specificity of the immunoprecipitation reactions (FIG. 4C). These results demonstrate that FIAT and ATF4 interact in mammalian osteoblasts.

Example 2

FIAT Represses ATF4 DNA Binding and Transcriptional Activity

Figure 5:
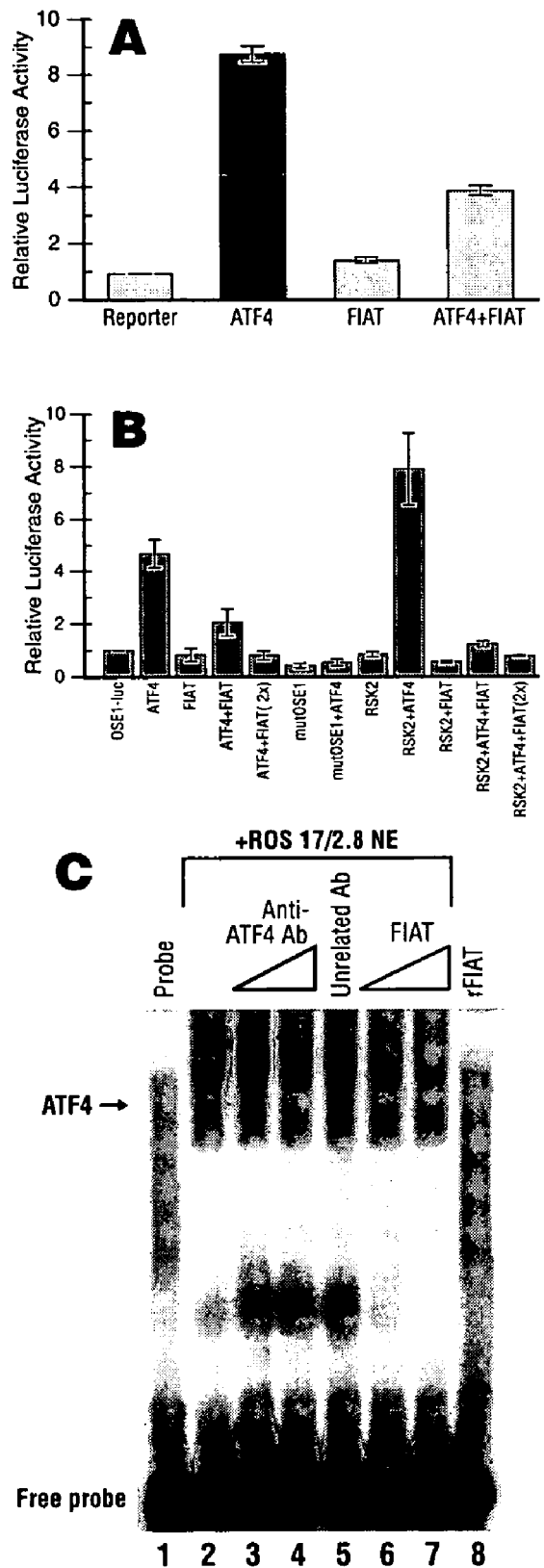
FIGS. 5A-5B are bar graphs illustrating that FIAT represses ATF4-dependent transcription.
FIG. 5C is a reproduction of an autoradiograph of an electrophoretic mobility shift assay with an OSE1 oligonucleotide probe, ROS 17/2.8 nuclear extract, and recombinant FIAT. The ATF4 binding complex was identified using specific anti-ATF4 antibodies (lanes 3-5). FIAT did not bind the probe but inhibited binding of ATF4 to the DNA.

ATF4 was recently characterized as an important transcriptional regulator of osteoblast differentiation, binding to the OSE1 site of the osteocalcin promoter to regulate osteocalcin gene transcription (Yang et al., 2004, Cell 117:387-98). ATF4 was shown to be a substrate for the RSK2 kinase and phosphorylation by RSK2 enhanced the transcriptional activity of ATF4 (Yang et al., 2004, Cell 117:387-98). Based on this, it was examined whether the interaction of FIAT with ATF4 would impact on the DNA-binding and transcriptional activity of ATF4 and regulate osteocalcin gene transcription in mammalian cells. In a first series of experiments, COS-7 cells were co-transfected with expression vectors for ATF4 and FIAT, and a reporter construct in which canonical ATF4 binding sites were subcloned upstream of the thymidine kinase minimal promoter region. The recombinant ATF4 protein strongly induced the transcription of the reporter gene, while FIAT by itself had no effect (FIG. 5A). Co-expression of FIAT with ATF4 significantly inhibited ATF4-mediated transcription (FIG. 5A). To test the impact of FIAT on the ATF4-mediated activation of osteocalcin gene transcription, osteoblastic MC3T3-E1 cells were transfected with a reporter construct in which six copies of the OSE-1 regulatory element from the osteocalcin gene promoter, which binds ATF4 (Yang et al., 2004, Cell 117:387-98), were introduced upstream of the adenovirus type 2 major late promoter fused to the luciferase reporter gene (vector OSE1-luc) (Ducy and Karsenty, 1995, Mol. Cell Biol. 15:1858-69). The cells also received expression vectors for ATF4, FIAT, and RSK2. As previously reported (Yang et al., 2004, Cell 117:387-98), ATF4 induced the transcription of the OSE1-luc reporter, and this effect was enhanced by RSK2 co-expression (FIG. 5B). FIAT suppressed the transcriptional activity of ATF4, even in the presence of RSK2 (FIG. 5B). A control reporter vector in which the OSE1 response element was mutated did not respond to ATF4 expression (mut OSE1, FIG. 3B). FIAT by itself was without effect (FIG. 5B). Similar results were obtained when MC3T3-E1 or COS-7 cells were transfected with a reporter construct under the control of the proximal 147 bp osteocalcin gene promoter. These experiments demonstrated that FIAT was able to inhibit ATF4-mediated transcription, and that this inhibition was maintained even when ATF4 was activated by phosphorylation.

To examine the mechanisms involved, electrophoretic mobility shift assays (EMSAs) were performed with nuclear extracts from ROS 17/2.8 osteoblastic cells and recombinant FIAT protein. The probe used was a 26 bp oligonucleotide corresponding to the OSE1 binding element and flanking nucleotides from the mouse osteocalcin promoter sequence. We observed the previously reported multiple retarded complexes between nuclear ROS 17/2.8 proteins and the probe (Ducy and Karsenty, 1995, Mol. Cell Biol. 15:1858-69; Schinke and Karsenty, 1999, J. Biol. Chem. 274:30182-9; Yang et al., 2004, Cell 117:387-98), and the ATF4 binding complex was identified using specific inhibition of DNA binding by anti-ATF4 antibodies (FIG. 5C). Recombinant FIAT protein did not bind the OSE1 probe (FIG. 5C), but dose-dependently inhibited the binding of ATF4 to the OSE1 element (FIG. 5C). Together with the data presented in FIG. 4, we interpret these results to mean that FIAT heterodimerizes with nuclear ATF4 to prevent its binding to DNA and repress ATF-mediated gene transcription.

Example 3

Reduced Bone Mass in Mice Expressing a FIAT Transgene

Figure 6A:
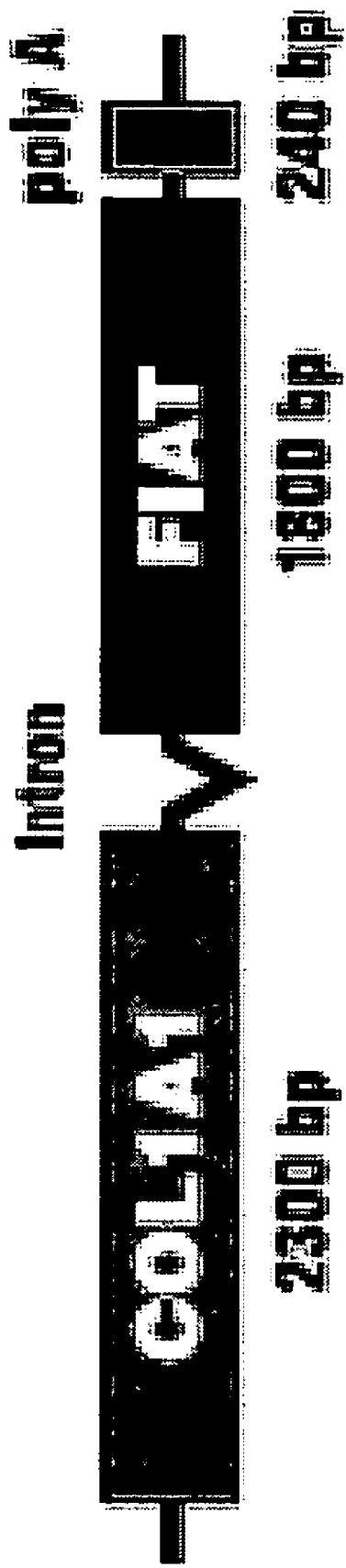
FIG. 6A is a schematic representation of the Col 1-FIAT transgene. Poly A represents an SV40 polyadenylation signal.
Figure 6B:
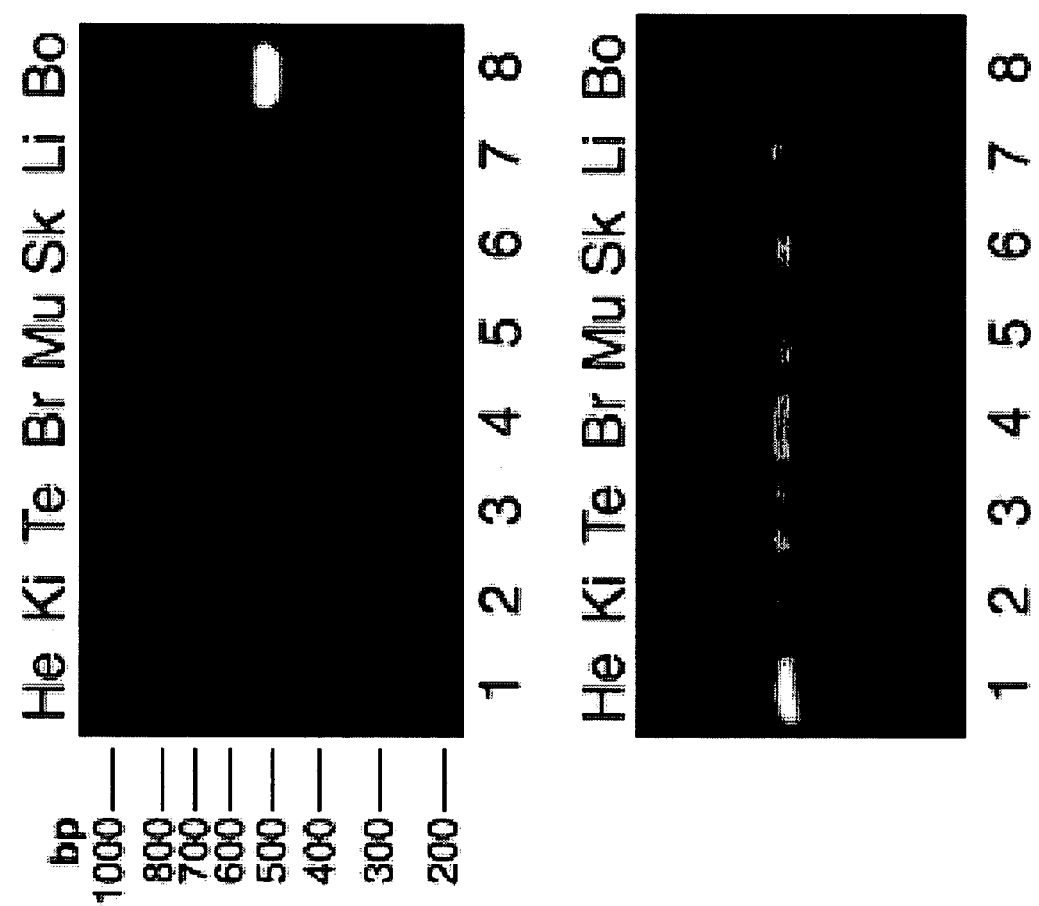
FIG. 6B-6C are reproductions of RT-PCR assays of FIAT gene expression. 6B: RT-PCR assay of transgene expression. Upper panel shows specific FIAT transgene expression using primers from the FIAT sequence and the SV40 polyadenylation sequence. Bottom panel shows GAPDH control expression. He, heart; Ki, kidney; Te, tendons; Br, brain; Mu, skeletal muscle; Sk, skin; Li, liver; Bo, bone. 6C: Endogenous FIAT and transgene expression in osteoblasts and bone. Reverse-transcription PCR with primers for endogenous FIAT (lanes 1, 2) or primers specific for the transgene (lane 3). RNA was from osteoblast primary cultures (lane 1) or calvaria. Wt, wild-type; Tg, transgenic.
Figure 6C:
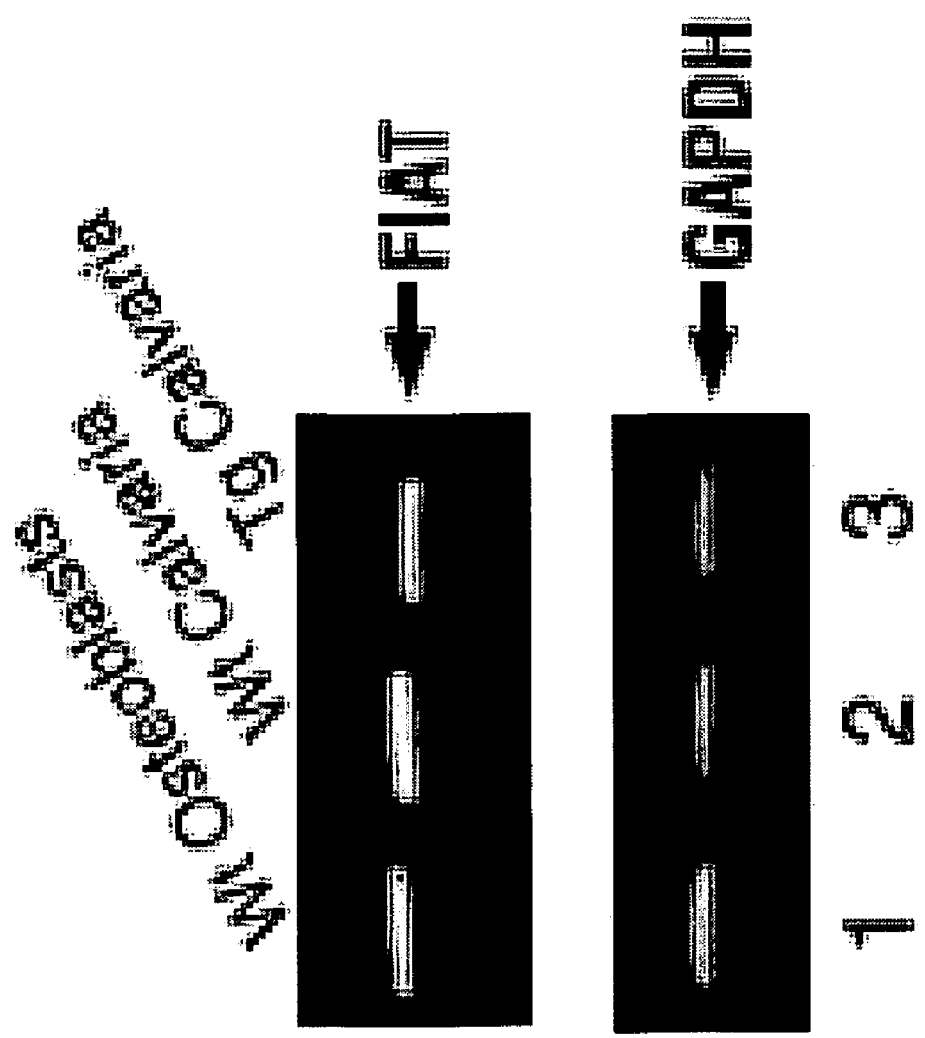
Figure 6D:
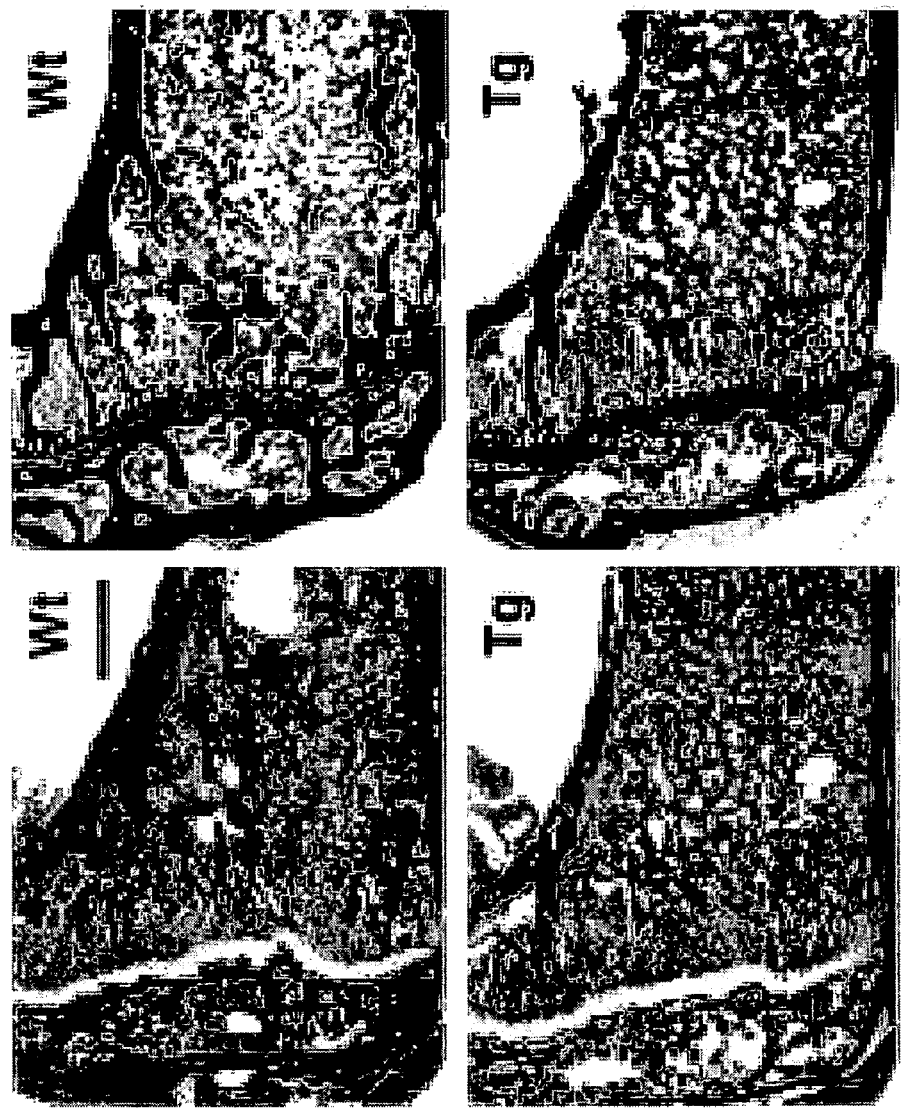
FIG. 6D is a set of micrographs of Goldner (left) and von Kossa (right) stains of tibial sections from FIAT transgenic mice (bottom panels) and wild-type littermates (upper panels) at 3 months of age.

To study the impact of FIAT on osteoblast development in vivo, transgenic mice expressing a FIAT transgene were generated. The transgene contained the full-length 1.8 kb FIAT cDNA fused to the 2.3 kb α1(I) collagen promoter (FIG. 6A). This promoter fragment is known to direct transgene expression specifically in osteoblasts, but not in other type I collagen-producing cells (Dacquin et al., 2002, Dev. Dyn. 224: 245-51; Rossert et al., 1995, J. Cell Biol. 129:1421-32). Tissue specificity of transgene expression was assessed by RT-PCR, and results confirmed that the transgene was expressed only in bone but not in other tissues (FIG. 6B). The level of transgene expression in bone tissue was comparable to endogenous FIAT gene expression (FIG. 6C). Histological analysis of tibial sections obtained from 3 month-old mice revealed an osteopenic phenotype in transgenic mice. The bone mass reduction was manifested as decreased number and size of trabeculae as well as disturbed secondary centers of ossification (FIG. 6C). The same phenotype was observed in another strain of transgenic mice, confirming that the phenotype was not integration site-dependent.

Figures 7A, 7B, 7C:
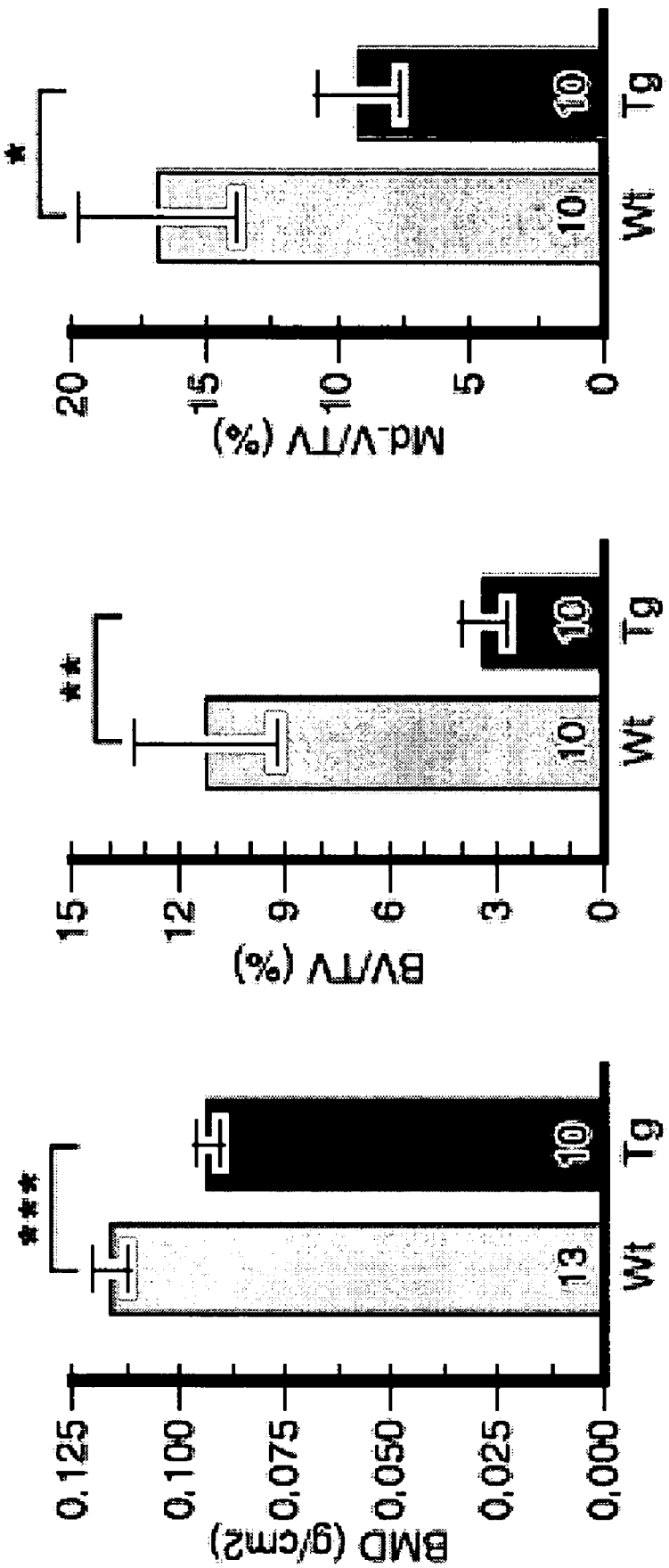
FIGS. 7A-7I are bar graphs depicting histomorphometric analysis of bones from FIAT transgenic mice (Tg) and wild type littermate controls (Wt) at three months of age. *, $p<0.05$; , $p<0.01$; *, $p<0.001$.
Figures 7D, 7E, 7F:
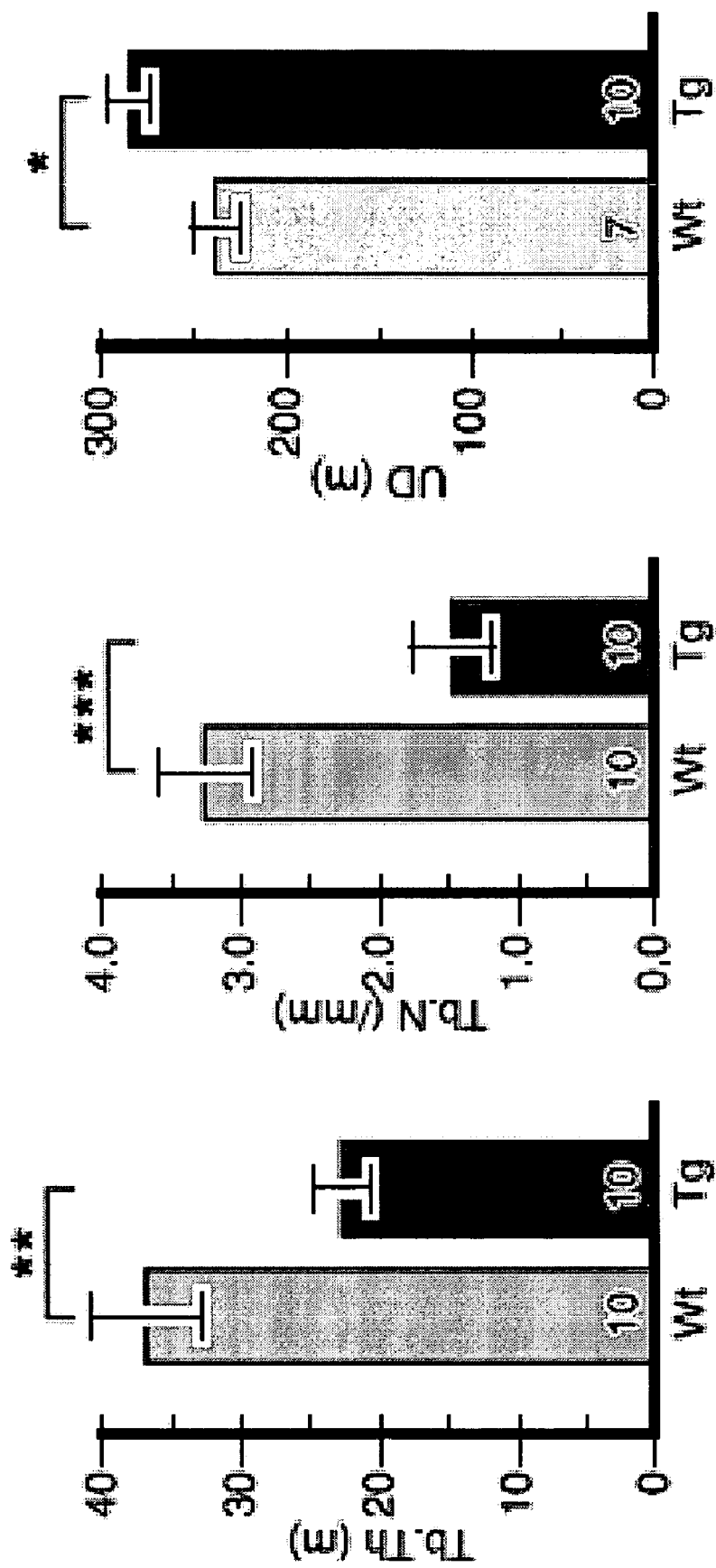
Figures 7G, 7H, 7I:
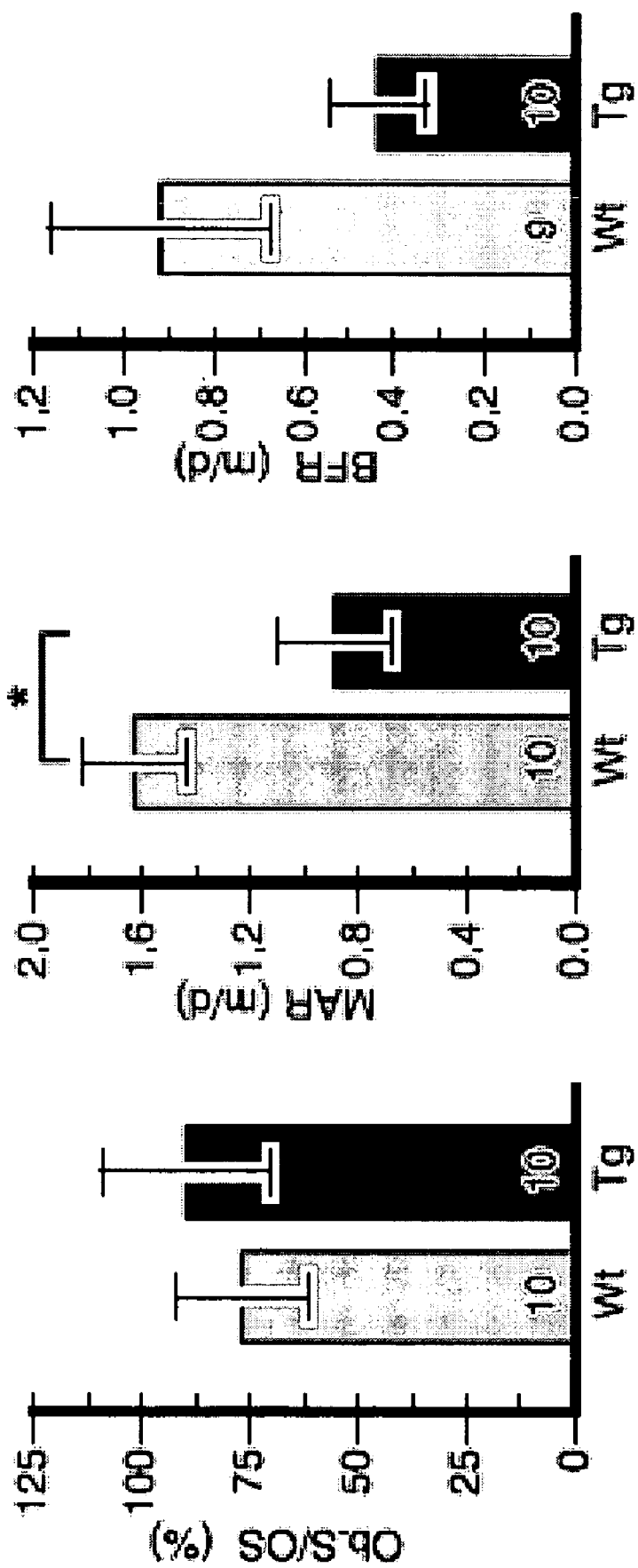

The osteopenic phenotype of the FIAT transgenic mice was further characterized using Dual Energy X-ray Absorptiometry (DEXA), histomorphometry, and biomechanical analyses. DEXA scanning reveealed a significant decrease (21%) in bone mineral density between transgenic animals and wild type littermates (FIG. 7A). Detailed histomorphometric measurements demonstrated a dramatic decrease in bone volume (70%), mineralized bone volume (45%), trabecular thickness (38%), and trabecular number (55%) (FIGS. 7B-7E). While the number of osteoblasts was not statistically different between transgenic animals and littermate controls (FIG. 7G), measurements of double-labeled tetracycline tibial sections revealed a lowered mineral apposition rate (46%) and bone formation rate (52%) in the transgenics (FIGS. 7H and 7I). The same trends were observed in younger transgenic animals at 3 weeks of age. In 6 month-old mice where bone formation rates are decreased, static histomorphometric parameters were similar between wild-type and transgenic littermates.

To determine if the measured changes had any effect on the mechanical properties of bone, femurs were subjected to mechanical testing using the 3-point bending method. Bones from transgenic animals exhibited a 20% increase in ultimate displacement compared to wild type controls (FIG. 7F), demonstrating that the reduced bone mineral density, lowered bone mass, and disrupted trabecular architecture resulted in a loss of rigidity in bones of transgenic animals.

Example 4

FIAT Impairs Osteoblast Activity

A decrease in bone mass can be secondary to endocrine dysfunction or result from defects in bone resorption or formation. Biochemical analysis of calcium, phosphate, and alkaline phosphatase levels in blood revealed no differences between blood parameters in wild type and transgenics, ruling out perturbations in mineral homeostasis and abnormal turnover as the cause of the phenotype. Similarly, histomorphometric measurement of osteoclast number, TRAP staining, and assessment of osteoclastic activity by collagen crosslink assays showed similar results between the two genotypes, eliminating the possibility of an effect of the transgene on the number and activity of osteoclasts.

Figure 8:
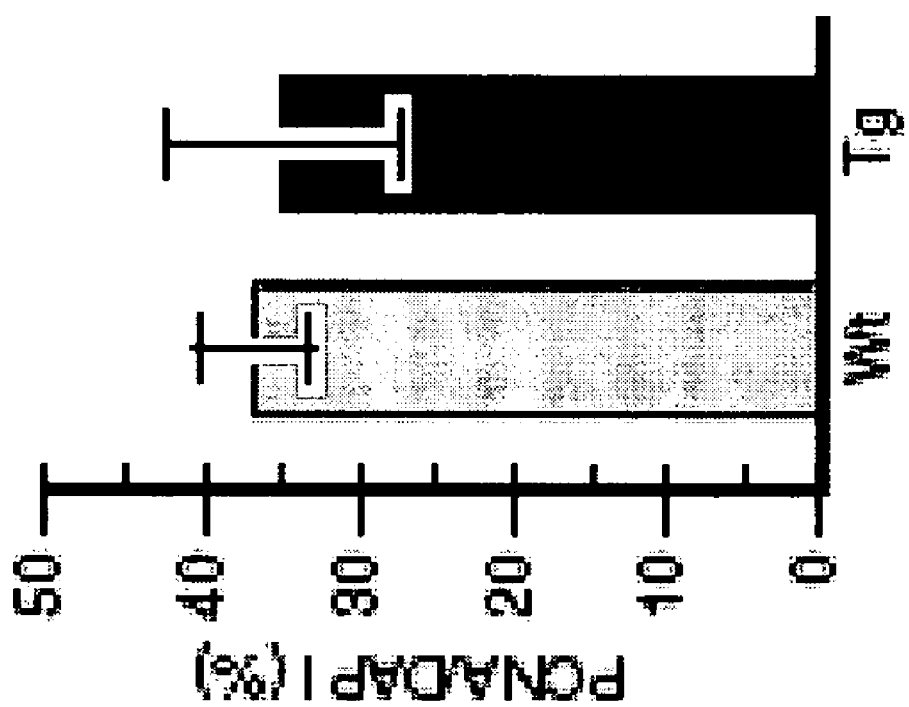
FIG. 8 is a bar graph depicting proliferation as PCNA positive cells divided by DAPI positive cells.
Figures 10A, 10B, 10C:
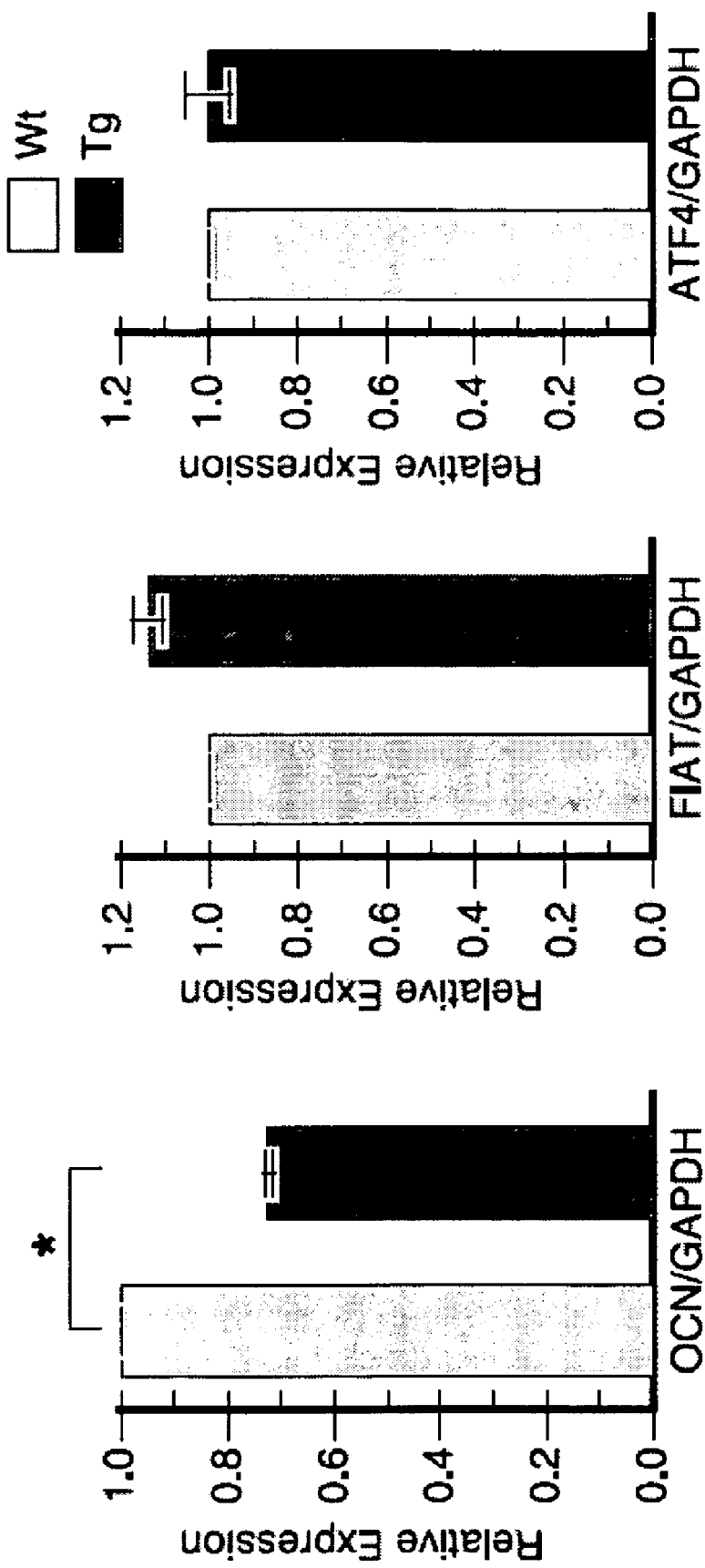
FIGS. 10A-10F are bar graphs of expression of osteoblast expression markers. RNA was extracted from 3 month old calvaria, reverse-transcribed, and amplified with specific TaqMan™ probes using Real Time PCR. Relative expression between wild-type (Wt) and transgenic (Tg) animals was calculated by the relative standard curve method and normalized to GAPDH. *, p<0.05.
Figures 10D, 10E, 10F:
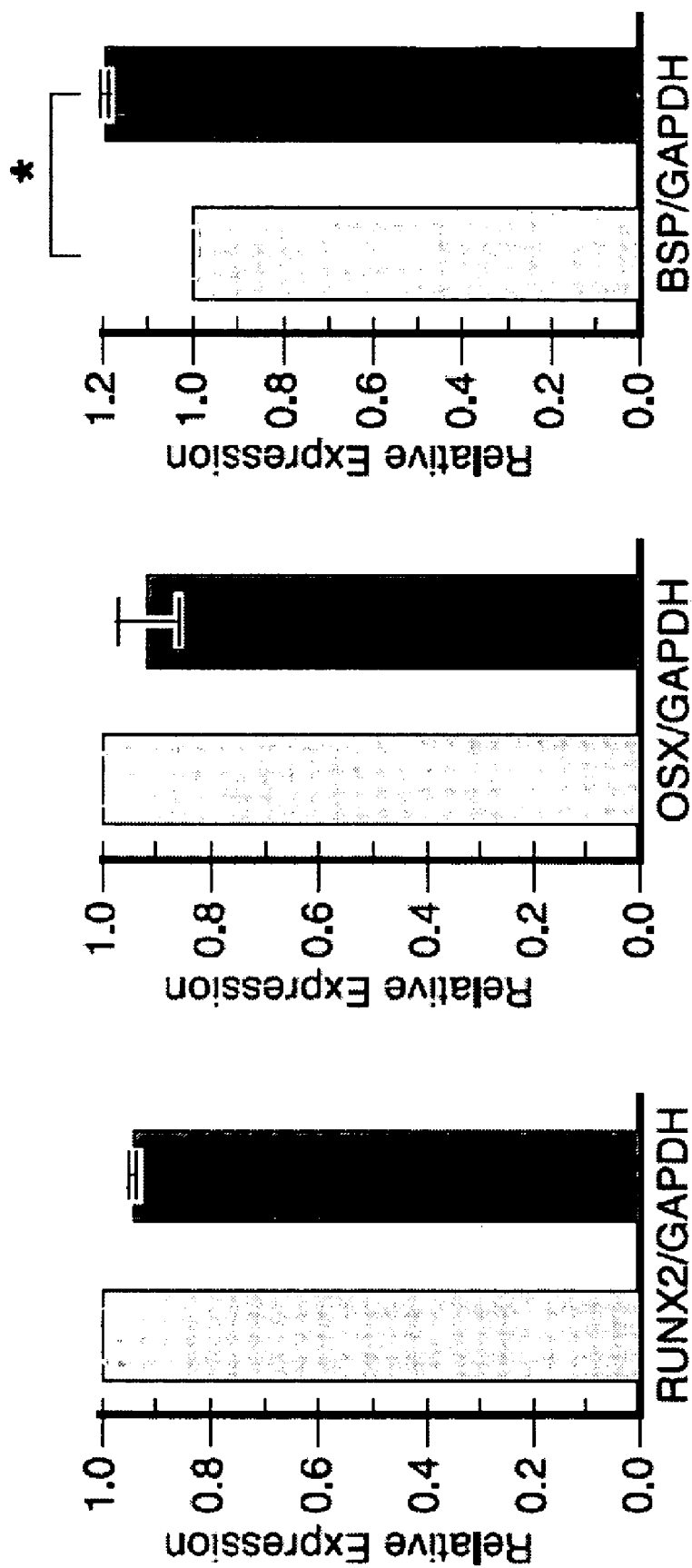

To determine if FIAT transgene expression altered osteoblast proliferation and/or apoptosis, osteoblasts were stained with PCNA to determine the rate of osteoblast proliferation, as well as by the TUNEL assay to evaluate apoptosis. These assays showed that FIAT did not affect the apoptotic rate or the proliferation of osteoblasts (FIG. 8), thus ruling out such mechanisms as causes of the osteopenic phenotype. Histomorphometric data had shown an attenuated mineral apposition rate and bone formation rate in transgenic mice (FIGS. 7H-7I), hinting at the possibility of a defect in osteoblastic activity. When primary osteoblast cultures obtained from 7 days old calvaria were analyzed for the production of alkaline phosphatase, a marker of osteoblastic differentiation and function, a statistically significant 34% decrease was observed in transgenic mice compared to wild type (FIG. 9A). Similarly, alizarin red staining of mineralized nodules formed by primary osteoblast cultures exhibited a 70% reduction in transgenic animals compared to wild type (FIG. 9B). Primary osteoblast cultures established from 3 months old bone marrow stromal cells also displayed a similar pattern (FIGS. 9C and 9D). The decrease in mineralization was readily evident in alizarin-red stained cultures.

To evaluate the impact of FIAT transgene expression on the transcription of markers of osteoblast differentiation, RNA levels of bone markers such as Ocn, Fiat, Atf4, Runx2/Cbfa1, Osx, and Bsp, were quantitated by Real Time Reverse Transcription-PCR (FIGS. 10A-10F). FIAT transgene expression inhibited Ocn transcription (FIG. 10A), as was observed in transient transfection assays (FIGS. 5A and 5B). Fiat expression was elevated in the transgenics, since the Real Time assay could detect transcripts from both the endogenous and transgenic Fiat alleles. Atf4, Runx2/Cbfa1, and Osx gene expression were unchanged, whereas Bsp mRNA levels were increased. Taken together, these data suggest that deregulated FIAT expression in bone cells caused an osteopenic phenotype due to a perturbation in osteoblastic activity, without much impact on differentiation.

Figure 11B:
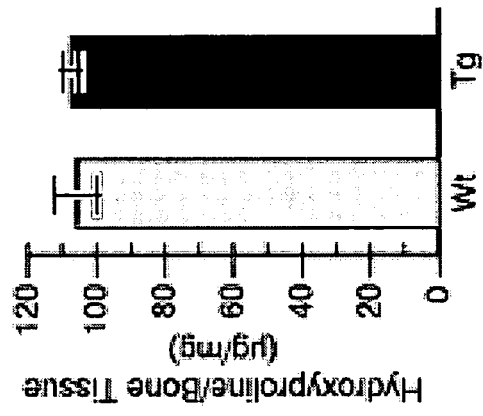
FIGS. 11A-11C are bar graphs depicting collagen-related parameters.
Figure 11A:
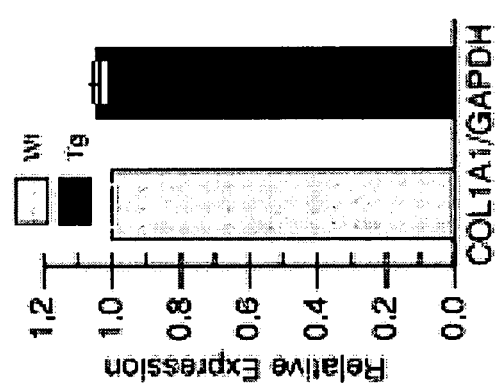
Figure 11C:
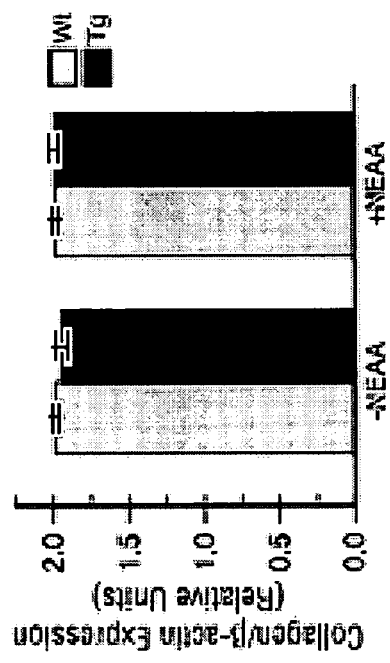

ATF4 controls the transcription of genes regulating the cellular import of amino acids (Harding et al., 2003, Mol. Cell 11:619-33). This was shown to affect the production of the major secreted protein of osteoblasts, type I collagen, and thus ATF4-deficient bones have less type I collagen in the matrix (Yang et al., 2004, Cell 117:387-98). It was examined whether FIAT transgenic bones were similarly affected. van Gieson staining of tibial sections from wild-type and transgenic littermates did not reveal major changes in type I collagen content in the matrix between the two genotypes. This was confirmed using quantification of Col1A1 transcription by Real Time Reverse Transcription-PCR (FIG. 11A) and by measuring hydroxyproline content in bone tissue (FIG. 11B). In addition, type I collagen synthesis from primary cultures of osteoblasts, in the presence or absence of non-essential amino acids, was unaffected by the expression of the FIAT transgene (FIG. 11C). Thus, deregulated FIAT transgene expression mimics some, but not all, aspects of the phenotype of ATF4-deficient bone. Nevertheless, the results show that perturbing FIAT expression in osteoblasts impacts on bone mass accrual, and strongly suggest that FIAT is a key determinant of osteoblast function.

These data demonstrate that FIAT is a transcriptional repressor controlling bone mass and identify a target for pharmacological intervention in bone cells. Compounds that inhibit FIAT activity in bone cells would lead to anabolic bone responses (increases in bone mass), such responses being useful for treating metabolic bone diseases and osteoporosis.

The transgenic strains of mice that overexpress FIAT in bone cells are useful, for example, as tools for testing the efficacy of such small molecules. The nucleic acids, polypeptides, vectors, cell lines, and antibodies described herein can be used to screen for candidate compounds and FIAT-modulating agents. Such a screen can be conducted in vitro and/or in vivo.

Example 5

Inhibition of FIAT in Cultured Osteoblasts Using RNA Knockdown

FIAT expression can be inhibited using RNA interference. The 'siRNA Target Finder' (Ambion) was used to find suitable 21 bp siRNA sequence to knockdown FIAT. The following sequences were identified and sequenced:

```
siRNA 762: sense strand:            (SEQ ID NO:14)
5'-GAACGACGUAAAGAAGCAAUU-3'
antisense strand: (SEQ ID NO:15)
5'-UUGCUUCUUUACGUCGUUCUU-3' siRNA 1312: sense strand:           (SEQ ID NO:16)
5'-CUGUCCGUGAUAAAGAGUAUU-3'
antisense strand: (SEQ ID NO:17)
5'-UACUCUUUAUCACGGACAGUU-3' siRNA 702: sense strand:            (SEQ ID NO:18)
5'-CUUCAGCGUCAUAAUAAGAUU-3'
antisense strand: (SEQ ID NO:19)
5'-UCUUAUUAUGACGCUGAAGUU-3'
```

Figure 12:
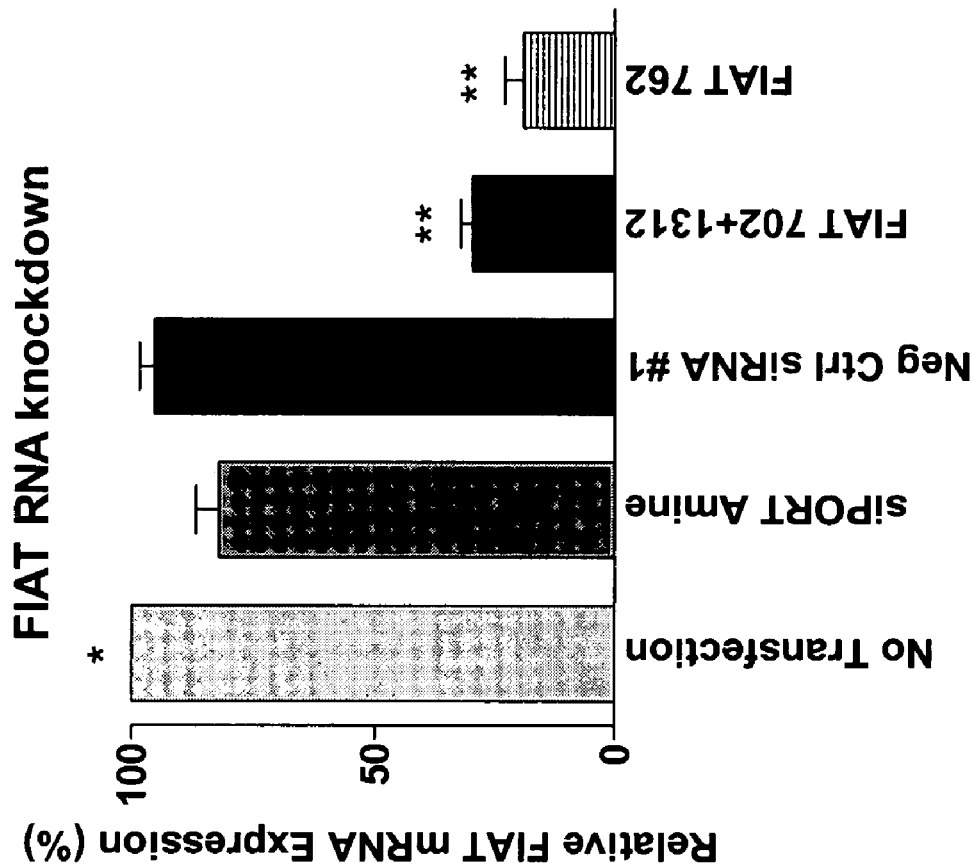
FIG. 12 is a bar graph depicting FIAT mRNA expression measured using Real Time Reverse Transcription PCR with a specific TaqMan™ probe. The expression levels measured in untransfected cells were assigned a value of 100%. Results are means±SEM of two experiments performed in duplicate. *, p<0.05; **, p<0.01 vs. siPORT™ Amine-treated cells.

MC3T3-E1 osteoblastic cells were transfected with the chemically synthesized siRNAs (Ambion) using siPORT™ Amine (Ambion) according to the manufacturer's instructions. Control wells were treated with the siPORT™ reagent only, or transfected with an siRNA control sequence that shows no homology to any inventoried gene in the mouse databases (control siRNA #1, Ambion). RNA and proteins were harvested 48 hours post-transfection and quantified by Real Time PCR amplification and Western blotting. This validated that all selected siRNAs were effective against FIAT. The selection criteria were low toxicity and efficient inhibition of FIAT mRNA (FIG. 12) and protein levels.

The validated siRNAs can be independently synthesized as complementary oligonucleotides with a loop sequence to generate siRNA hairpins with the sequences listed below:

```
siRNA 762: sense strand:            (SEQ ID NO:20)
5'-GATCCGAACGACGTAAAGAAGCAATTCAAGAGATTGCTTCTTTACG
TCGTTCTTA-3' antisense strand:                   (SEQ ID NO:21)
5'-AGCTTAAGAACGACGTAAAGAAGCAATCTCTTGAATTGCTTCTTTA
CGTCGTTCG-3' siRNA 1312: sense strand:           (SEQ ID NO:22)
5'-GATCCCTGTCCGTGATAAAGAGTATTCAAGAGATACTCTTTATCACG
GACAGTTA-3' antisense strand:                   (SEQ ID NO:23)
5'-AGCTTAACTGTCCGTGATAAAGAGTATCTCTTGAATACTCTTTATCA
CGGACAGG-3' siRNA 702: sense strand:            (SEQ ID NO:24)
5'-GATCCCTTCAGCGTCATAATAAGATTCAAGAGATCTTATTATGACGC
TGAAGTTA-3' antisense strand:                   (SEQ ID NO:25)
5'-AGCTTAACTTCAGCGTCATAATAAGATCTCTTGAATCTTATTATGAC
GCTGAAGG-3'
```

The oligonucleotides can be hybridized (annealed) and inserted into the pSilencer™ 4.1-CMV expression vector (Ambion). The effects of the selected siRNAs can be compared to the effect of a control, unrelated siRNA (Ambion) and to empty vector-transfected cells.

MC3T3-E1 preosteoblasts exhibiting high differentiation/mineralization potential can be transfected with the FIAT siRNA plasmid vectors, the control siRNA vector, or the empty pSilencer™ plasmid backbone. Assays will include FIAT expression, onset and level of osteocalcin gene transcription, type I collagen synthesis, and mineralization.

The extent of the FIAT knockdown can be assessed by parallel monitoring of endogenous FIAT mRNA and protein. For quantification of FIAT mRNA levels, Real Time Reverse Transcription PCR can be used. FIAT protein levels can be measured by Western blotting using conventional protocols and the anti-FIAT peptide antibody.

RNA can be harvested from control cells (empty plasmid- and control siRNA-transfected) and FIAT siRNA-expressing cells at intervals after plating: subconfluence, confluence, and 3, 7, 10, 14, and 21 days post-confluence. The cells undergo a temporal sequence of gene expression starting with collagen synthesis followed by induction of specific genes associated with the osteoblast phenotype, including osteocalcin. Osteocalcin expression can be quantified using Real Time Reverse Transcription PCR with a specific osteocalcin TaqMan™ probe. This can determine if FIAT knockdown modifies the onset of osteocalcin gene transcription or impacts on the overall level of osteocalcin expression.

Since ATF4 regulates the synthesis of type I collagen and FIAT modulates ATF4 activity, collagen synthesis can also be measured in osteoblasts deficient for FIAT following RNA interference. Briefly, osteoblasts can be labeled with $^3$H-proline (Amersham) for 12 hours in proline-free DMEM, in the presence or absence of nonessential amino acid mix. Cells can be homogenized, the procollagen digested to collagen using pepsin, and precipitated collagen can be resolved by SDS-PAGE.

The impact of FIAT RNA knockdown on osteoblast function can be assessed by culturing the cells in mineralizing media and measuring alkaline phosphatase activity and mineralization. The growth medium can be supplemented with ascorbic acid and β-glycerophosphate. Cells can be assayed for alkaline phosphatase level after 7 days, or stained with alizarin red after 14 days. For colorimetric determination of alkaline phosphatase level, 4-nitrophenyl phosphate (Sigma) can be added to each well and incubated for 30 minutes before reading at 405 nm. Alkaline phosphatase concentration can be normalized by protein concentration per well. For alizarin red staining, cells can be fixed and stained with alizarin red (Sigma). Dark red mineralized nodules can be photographed with bright-field microscopy and quantified by counting the number of nodules per square millimeter.

Example 6

FIAT Mutation Analysis

The FIAT amino acid sequence includes three putative leucine zippers predicted to be important for protein-protein interactions, e.g., binding to ATF4. Deletion mutants of FIAT were produced using inverse-PCR (Ausubel et al., supra) to delete amino acids 135-156, 194-222, or 434-455 that encode these putative zippers. The resulting mutant proteins were named A135-156, A194-222, and A434-455, and encoded by the following nucleic acid sequences:

(SEQ ID NO:26)
ATGGCGACGCGGGTAGAGGAGGCGGCGCGGGGAAGAGGCGGCGGCGCCGA
AGAGGCGACTGAGGCCGGACGGGGCGGACGGCGACGCAGCCCGCGGCAGA
AGTTTGAAATTGGCACAATGGAAGAAGCTGGAATTTGTGGGCTAGGGGCG
AAAGCAGATATGTTGTGTAACTCTCAATCAAATGATATTCTTCAACATCA
AGGCTCAAATTGTGGTGGCACAAGTAACAAGCATTCATTGGAAGAGGATG
AAGGCAGTGACTTTATAACAGAGAACAGGAATTTGGTGAGCCCAGCATAC
TGCACGCAAGAATCAAGAGAGGGAAATCCCTGGGGGAGAAGCTCGAACAGA
TCCCCCTGATGGTCAGCAAGATTCAGAGTGCAACAGGAACAAAGAAAAAA
CTGCAGCTCTCTGTAAGAAATATGCTGATCTTCTGGAGGAGAGCAGGAGT
GTTCAGAAGCAAATGAAGATCCTGCAGAAGAAGCAAGCCCAGATTGTGAA
AGAGAAAGTTCACTTGCAGAGTGAACATAGCAAGGCTATCTTGGCAAGAA
GCAAGCTAGAATCTCTTTGCAGAGAACTTCAGCGTCACAATAAGACGTTA
AAGGAGGAAAATATGCAGCAGGCACGAGAGGAAGAAGAACGACGTAAAGA
AGCAACTGCACATTTCCAGATTACCTTAGATGAAATTCAAGCCCAGCTGG
AGCAGCATGACATCCACAACGCCAAACTCCGACAGGAAAACATTGAGCTG
GGGGAGAAGCTAAAGAAGCTCATCGAACAGTACGCACTGAGGGAAGAGCA
CATTGATAAGGTGTTCAAACGTAAGGAACTGCAACAGCAGCTCGTGGATG
CCAAACTGCAGCAAACGACACAACTGATAAAAGAAGCTGATGAAAAACAT
CAGAGAGAGAGAGAGTTTTTATTAAAAGAAGCGACAGAATCGAGGCACAA
ATACGAACAAATGAAACAGCAGGAAGTACAACTAAAACAGCAGCTTTCTC
TTTATATGGATAAGTTTGAAGAATTCCAGACTACCATGGCAAAAAGCAAT
GAACTGTTTACAACCTTCAGACAGGAAATGGAAAAGATGACAAAGAAAAT
TAAAAAACTGGAAAAAGAAACAATAATTTGGCGTACCAAATGGGAAAACA
ATAATAAAGCACTTCTGCAAATGGCTGAAGAGAAAACAGTCCGTGATAAA
GAGTACAAGGCCCTTCAAATAAAACTGGAACGGTTAGAGAAGCTGTGCAG
GGCTCTTCAAACAGAAAGGAATGAGCTCAATGAGAAGGTGGAAGTCCTGA
AAGAGCAGGTATCCATCAAAGCGGCCATCAAAGCGGCGAACAGGGATTTA
GCAACACCTGTGATGCAGCCCTGTACTGCCCTGGATTCTCACAAGGAGCT
GAACACTTCCTCGAAAAGAGCCCTGGGAGCGCACCTGGAGGCTGAGCCCA
AGAGTCAGAGAAGCGCTGTGCAAAAGCCCCCGTCCACAGGCTCTGCTCCG
GCCATCGAGTCGGTTGACTAA (SEQ ID NO:27)
ATGGCGACGCGGGTAGAGGAGGCGGCGCGGGGAAGAGGCGGCGGCGCCGA
AGAGGCGACTGAGGCCGGACGGGGCGGACGGCGACGCAGCCCGCGGCAGA
AGTTTGAAATTGGCACAATGGAAGAAGCTGGAATTTGTGGGCTAGGGGTG
AAAGCAGATATGTTGTGTAACTCTCAATCAAATGATATTCTTCAACATCA
AGGCTCAAATTGTGGTGGCACAAGTAACAAGCATTCATTGGAAGAGGATG
AAGGCAGTGACTTTATAACAGAGAACAGGAATTTGGTGAGCCCAGCATAC
TGCACGCAAGAATCAAGAGAGGAAATCCCTGGGGGAGAAGCTCGAACAGA
TCCCCCTGATGGTCAGCAAGATTCAGAGTGCAACAGGAACAAAGAAAAAA
CTTTAGGAAAAGAAGTTTTATTACTGATGCAAGCCCTAAACACCCTTTCA
ACCCCAGAGGAGAAGCTGGCAGCTCTCTGTAAGAAATATGCTGATCTTCT
GGAGGAGAGCAGGAGTGTTCAGAAGCAAATGAAGATCCTGCAGAAGAAGC
AAGCCCAGATTGTGAAAGAGAAAGTTCACAAGGAGGAAAATATGCAGCAG
GCACGAGAGGAAGAAGAACGACGTAAAGAAGCAACTGCACATTTCCAGAT
TACCTTAGATGAAATTCAAGCCCAGCTGGAGCAGCATGACATCCACAACG
CCAAACTCCGACAGGAAAACATTGAGCTGGGGGAGAAGCTAAAGAAGCTC
ATCGAACAGTACGCACTGAGGGAAGAGCACATTGATAAGGTGTTCAAACG
TAAGGAACTGCAACAGCAGCTCGTGGATGCCAAACTGCAGCAAACGACAC
AACTGATAAAAGAAGCTGATGAAAAACATCAGAGAGAGAGAGAGTTTTTA
TTAAAAGAAGCGACAGAATCGAGGCACAAATACGAACAAATGAAACAGCA
GGAAGTACAACTAAAACAGCAGCTTTCTCTTTATATGGATAAGTTTGAAG
AATTCCAGACTACCATGGCAAAAAGCAATGAACTGTTTACAACCTTCAGA
CAGGAAATGGAAAAGATGACAAAGAAAATTAAAAAACTGGAAAAAGAAAC
AATAATTTGGCGTACCAAATGGGAAAACAATAATAAAGCACTTCTGCAAA
TGGCTGAAGAGAAAACAGTCCGTGATAAAGAGTACAAGGCCCTTCAAATA
AAACTGGAACGGTTAGAGAAGCTGTGCAGGGCTCTTCAAACAGAAAGGAA
TGAGCTCAATGAGAAGGTGGAAGTCCTGAAAGAGCAGGTATCCATCAAAG
CGGCCATCAAAGCGGCGAACAGGGATTTAGCAACACCTGTGATGCAGCCC
TGTACTGCCCTGGATTCTCACAAGGAGCTGAACACTTCCTCGAAAAGAGC
CCTGGGAGCGCACCTGGAGGCTGAGCCCAAGAGTCAGAGAAGCGCTGTGC
AAAAGCCCCCGTCCACAGGCTCTGCTCCGGCCATCGAGTCGGTTGACTAA (SEQ ID NO:28)
ATGGCGACGCGGGTAGAGGAGGCAGCGCGGGGAAGAGGCGGCGGCGCCGA
AGAGGCGACTGAGGCCGGACGGGGCGGACGGCGACGCAGCCCGCGGCAGA
AGTTTGAAATTGGCACAATGGAAGAAGCTGGAATTTGTGGGCTAGGGGTG
AAAGCAGATATGTTGTGTAACTCTCAATCAAATGATATTCTTCAACATCA
AGGCTCAAATTGTGGTGGCACAAGTAACAAGCATTCATTGGAAGAGGATG
AAGGCAGTGACTTTATAACAGAGAACAGGAATTTGGTGAGCCCAGCATAC
TGCACGCAAGAATCAAGAGAGGAAATCCCTGGGGGAGAAGCTCGAACAGA
TCCCCCTGATGGTCAGCAAGATTCAGAGTGCAACAGGAACAAAGAAAAAA
CTTTAGGAAAAGAAGTTTTATTACTGATGCAAGCCCTAAACACCCTTTCA
ACCCCAGAGGAGAAGCTGGCAGCTCTCTGTAAGAAATATGCTGATCTTCT
GGAGGAGAGCAGGAGTGTTCAGAAGCAAATGAAGATCCTGCAGAAGAAGC
AAGCCCAGATTGTGAAAGAGAAAGTTCACTTGCAGAGTGAACATAGCAAG
GCTATCTTGGCAAGAAGCAAGCTAGAATCTCTTTGCAGAGAACTTCAGCG
TCACAATAAGACGTTAAAGGAGGAAAATATGCAGCAGGCACGAGAGGAAG
AAGAACGACGTAAAGAAGCAACTGCACATTTCCAGATTACCTTAGATGAA
ATTCAAGCCCAGCTGGAGCAGCATGACATCCACAACGCCAAACTCCGACA
GGAAAACATTGAGCTGGGGGAGAAGCTAAAGAAGCTCATCGAACAGTACG
CACTGAGGGAAGAGCACATTGATAAGGTGTTCAAACGTAAGGAACTGCAA
CAGCAGCTCGTGGATGCCAAACTGCAGCAAACGACACAACTGATAAAAGA
AGCTGATGAAAAACATCAGAGAGAGAGAGTTTTTATTAAAAGAAGCGA
CAGAATCGAGGCACAAATACGAACAAATGAAACAGCAAGAAGTACAACTA

```
                                          -continued
AAACAGCAGCTTTCTCTTTATATGGATAAGTTTGAAGAATTCCAGACTAC
CATGGCAAAAAGCAATGAACTGTTTACAACCTTCAGACAGGAAATGGAAA
AGATGACAAAGAAAATTAAAAAACTGGAAAAAGGAACAATAATTTGGCGT
ACCAAATGGGCAAAACAATAATAATAAAGCACTTCTGCAAATGGCTGAAG
AGAAAACAGTCCGTGATAAAGAGTACAAGGCCCTTCAAATAAAACTGAAA
CGGAAAGAGCAGGTATCCATCAAAGCGGCCATCAAAGCGGCGAACAGGGA
TTTAGCAACACCTGTGATGCAGCCCTGTACTGCCCTGGATTCTCACAAGG
AGCTGAACACTTCCTCGAAAAGAGTCCTGGGAGCGCACCTGGAGGCTGAG
CCCAAGAGTCAGAGAAGCGCTGTGCAAAAGCCCCCGTCCACAGGCTCTGC
TCCGGCCATCGAGTCGGTTGACTAA
```

Figure 13:
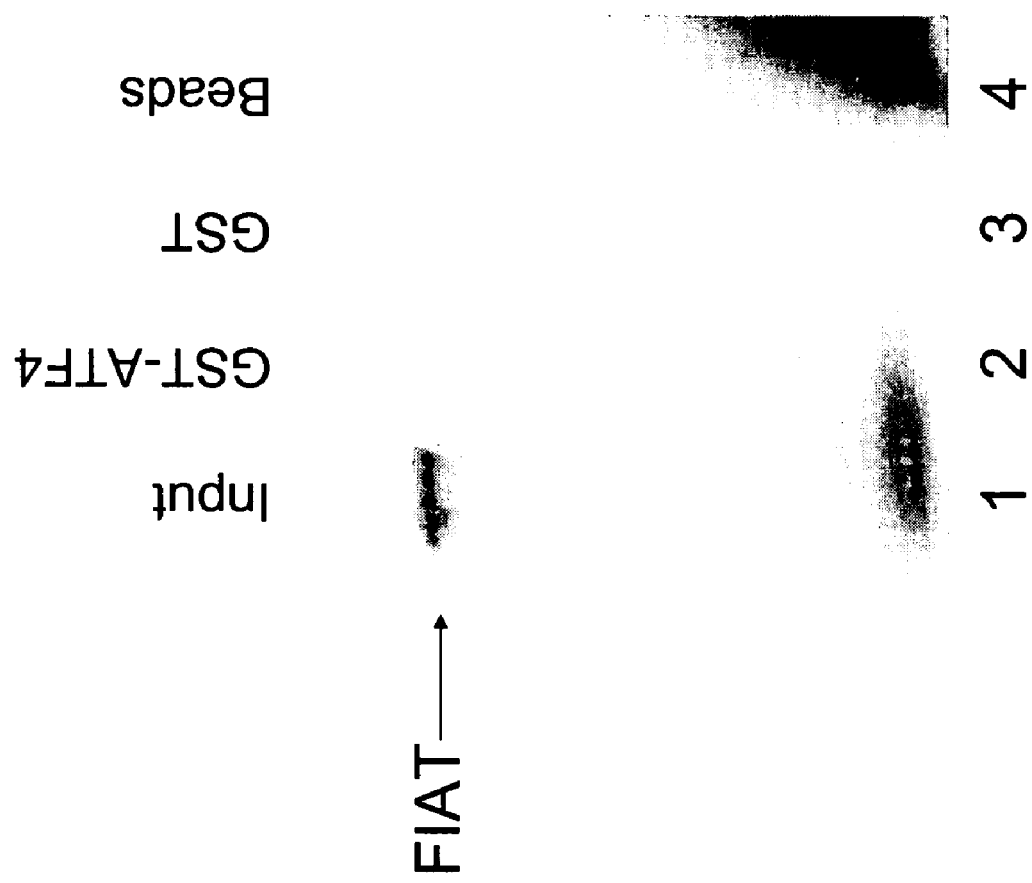
FIG. 13 is a reproduction of the results of an in vitro assay to detect binding between FIAT and ATF4. In vitro translated wild-type FIAT was incubated with recombinant GST-ATF4 and glutathione-sepharose beads. The bound proteins were washed and analyzed by SDS-PAGE and autoradiography. Controls included binding to the GST moiety (lane 3) or to the glutathione-sepharose beads alone (lane 4). A signal is detected in lane 2, demonstrating the interaction of labeled wild-type FIAT with GST-ATF4.

To identify the functional leucine zipper within the FIAT sequence, protein pull-down assays can be performed with labeled, in vitro translated wild-type FIAT and deletion mutants, and recombinant GST-ATF4 (Abnova Corporation, Taipei, Taiwan). One microgram of GST-ATF4 or of the empty GST moiety can be bound to glutathione Sepharose® beads in wash buffer (20 mM Tris-HCl, pH 7.5, 150 mM NaCl, 0.1% NP-40, 10 mM DTT) and pre-incubated with 1 mg/ml of BSA for 2 hours, then incubated with the labeled target proteins in wash buffer overnight at 4° C. The bound proteins are then washed 5 times with wash buffer. Bound proteins can be eluted by boiling the beads in SDS sample buffer and subsequently subjected to SDS-PAGE. FIG. 13 depicts the results of such an assay performed with wild-type FIAT.

The results obtained with the protein pull-down assay can be confirmed at the functional level in transient transfection assays. MC3T3-E1 osteoblastic cells can be transfected with the OSE1-luc reporter (Ducy and Karsenty, 1995, Mol. Cell Biol. 15:1858-1869), an internal control for monitoring the efficiency of transformation (pSV$_6$TKCAT), and expression vectors for ATF4 and the various FIAT deletion mutants using the Lipofectamine™ (Invitrogen Life Technologies, Burlington, Ontario) reagent according to manufacturer's instructions. Luciferase assay and chloramphenicol acetyltransferase ELISA (Roche Applied Science, Laval, Quebec) can be performed 24 hours after transfection according to the manufacturer's protocol. Inhibition of ATF4-mediated transcription (assessed by measuring luciferase/chloramphenicol acetyltransferase ratios) can be compared between wild-type and leucine-zipper-deleted FIAT mutants.

It is expected that one of the zipper-deleted mutants (Δ135-156, Δ194-222, or Δ434-455) will be inactive in these assays, i.e. it will not interact with ATF4 in the pull-down assay and should not repress ATF4-dependent transcription. This structure-function analysis can map the functional leucine zipper within the FIAT sequence responsible for interaction with ATF4.

Alternately, the FIAT zipper-deleted mutants can be tagged with the FLAG epitope and expressed in ROS 17/2.8 osteoblastic cells. Co-immunoprecipitation with anti-FLAG antibodies, followed by immunoblotting for ATF4, can allow mapping of the functional zipper in mammalian cells. FLAG epitope tagging can eliminate any potential background signal caused by the endogenous FIAT protein in the co-immunoprecipitation assay.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. An isolated nucleic acid molecule comprising:
   (i) a first nucleic acid sequence consisting of 87 nucleotides encoding a fragment of a Factor Inhibiting ATF4-mediated Transcription (FIAT) polypeptide consisting of amino acids 194-222 of SEQ ID NO:2; and
   (ii) a second non-FIAT nucleic acid sequence unrelated to the first nucleic acid sequence that is directly contiguous with the 3' or 5' end of the first nucleic acid sequence.

2. The isolated nucleic acid molecule of claim 1, wherein the second non-FIAT nucleic acid sequence encodes a non-FIAT polypeptide selected from the group consisting of: a hexa-histidine tag; a hemagglutinin tag; an immunoglobulin constant (Fc) region; a secretory sequence; and a detectable marker selected from the group consisting of: β-galactosidase, invertase, green fluorescent protein, luciferase, chloramphenicol acetyltransferase, beta-glucuronidase, exo-glucanase and glucoamylase.

3. The isolated nucleic acid of claim 2, wherein in the non-FIAT polypeptide is contiguous with the N-terminus or C-terminus of the FIAT polypeptide.

4. A cell comprising an exogenously-introduced nucleic acid molecule of claim 1.

5. A cell comprising an exogenously-introduced nucleic acid molecule of claim 2.

6. A cell comprising an exogenously-introduced nucleic acid molecule of claim 3.

7. An isolated nucleic acid molecule encoding a polypeptide that:
   (a) consists of:
      (i) a Factor Inhibiting ATF4-mediated Transcription (FIAT) polypeptide sequence consisting of amino acids 194-222 of SEQ ID NO:2; and
      (ii) a fusion partner selected from the group consisting of: a hexa-histidine tag; a hemagglutinin tag; an immunoglobulin constant (Fc) region; a secretory sequence; and a detectable marker selected from the group consisting of: β-galactosidase, invertase, green fluorescent protein, luciferase, chloramphenicol acetyltransferase, beta-glucuronidase, exo-glucanase and glucoamylase, wherein in the encoded polypeptide the fusion partner is directly contiguous with the N-terminus or C-terminus of the FIAT polypeptide; and
   (b) displays activating transcription factor-4 (ATF4) protein binding ability.

8. A cell comprising an exogenously-introduced nucleic acid molecule of claim 7.

9. An isolated polypeptide encoded by the isolated nucleic acid molecule of claim 1.

10. An isolated polypeptide encoded by the isolated nucleic acid molecule of claim 2.

11. An isolated polypeptide encoded by the isolated nucleic acid molecule of claim 3.

12. An isolated polypeptide encoded by the isolated nucleic acid molecule of claim 7.

13. A recombinant protein comprising amino acids 194-222 of SEQ ID NO:2 directly linked at its C-terminal end, N-terminal end, or both C-terminal and N-terminal ends, to at least one non-Factor Inhibiting ATF4-mediated Transcription (FIAT) polypeptide amino acid sequence.

14. The recombinant protein of claim 13, wherein the non-FIAT amino acid sequence is selected from the group consisting of: a hexa-histidine tag; a hemagglutinin tag; an immunoglobulin constant (Fc) region; a secretory sequence; and a detectable marker selected from the group consisting of: β-galactosidase, invertase, green fluorescent protein, luciferase, chloramphenicol acetyltransferase, beta-glucuronidase, exo-glucanase and glucoamylase.

15. An isolated nucleic acid molecule encoding the recombinant protein of claim 13.

* * * * *

SEQUENCE LISTING

```
<160> NUMBER OF SEQ ID NOS: 28

<210> SEQ ID NO 1
<211> LENGTH: 2045
<212> TYPE: DNA
<213> ORGANISM: Homo sapiens

<400> SEQUENCE: 1
gagattctgt gccccttgtc gggccgcttg tttggctgct gccgtcacct catggcgacg      60
cgggtagagg aggcagcgcg gggaagaggc ggcggcgccg aagaggcgac tgaggccgga     120
cggggcggac ggcgacgcag cccgcggcag aagtttgaaa ttggcacaat ggaagaagct     180
ggaatttgtg ggctaggggt gaaagcagat atgttgtgta actctcaatc aaatgatatt     240
cttcaacatc aaggctcaaa ttgtggtggc acaagtaaca agcattcatt ggaagaggat     300
gaaggcagtg actttataac agagaacagg aatttggtga gcccagcata ctgcacgcaa     360
gaatcaagag aggaaatccc tggggagaa  gctcgaacag atcccctga  tggtcagcaa     420 gattcagagt gcaacaggaa caaagaaaaa actttaggaa agaagttttt attactgatg     480
caagccctaa acacccttc  aacccagag  gagaagctgg cagctctctg taagaaatat     540
gctgatcttc tggaggagag caggagtgtt cagaagcaaa tgaagatcct gcagaagaag     600
caagcccaga ttgtgaaaga gaaagttcac ttgcagagtg aacatagcaa ggctatcttg     660
gcaagaagca agctagaatc tctttgcaga gaacttcagc gtcacaataa gacgttaaag     720
gaggaaaata tgcagcaggc acgagaggaa gaagaacgac gtaaagaagc aactgcacat     780
```

```
ttccagatta ccttagatga aattcaagcc cagctggagc agcatgacat ccacaacgcc    840
aaactccgac aggaaaacat tgagctgggg gagaagctaa agaagctcat cgaacagtac    900
gcactgaggg aagagcacat tgataaggtg ttcaaacgta aggaactgca acagcagctc    960
gtggatgcca aactgcagca acgacacaa ctgataaaag aagctgatga aaacatcag     1020 agagagagag agttttatt aaaagaagcg acagaatcga ggcacaaata cgaacaaatg    1080
aaacagcagg aagtacaact aaaacagcag cttctctctt atatggataa gtttgaagaa    1140
ttccagacta ccatggcaaa aagcaatgaa ctgtttacaa ccttcagaca ggaaatggaa    1200
aagatgacaa agaaaattaa aaactggaa aagaaacaa taatttggcg taccaaatgg      1260
gaaaacaata taaagcact tctgcaaatg gctgaagaga aacagtccg tgataaagag       1320 tacaaggccc ttcaaataaa actggaacgg ttagagaagc tgtgcagggc tcttcaaaca    1380
gaaaggaatg agctcaatga aaggtggaa gtcctgaaag agcaggtatc catcaaagcg     1440
gccatcaaag cggcgaacag ggatttagca acacctgtga tgcagccctg tactgccctg    1500
gattctcaca aggagctgaa cacttcctcg aaaagagccc tgggagcgca cctggaggct    1560
gagcccaaga gtcagagaag cgctgtgcaa agcccccgt ccacaggctc tgctccggcc     1620
atcgagtcgg ttgactaaga tgaggtgtga tcactgtatt gagagatata ttttgtgtat    1680
aactttctct gttagtagtt aactattggt tttgtggtga aaattttctt acttttcta     1740 ccatatctgt attttcttag aactactgga cttatgtggt acaggaggct gcttagcagt    1800
tttgaatagt ttaatctata aattttcctc agctgtgttg cacatcagcc tcgttctccc    1860
tccactggaa tgcatgtgtt cactgccttg tcctttctct ccctgctcct tgcacattat    1920
catcctaatg aaaatttcac tgacagggcc gaccattaca agggaacttt gttctgacga    1980
tggttccttg atgtgaaaac aatattaatt taaacgtctt agccccccc cccataatat      2040 tattc                                                               2045
```

<210> SEQ ID NO 2
<211> LENGTH: 528
<212> TYPE: PRT
<213> ORGANISM: Homo sapiens

<400> SEQUENCE: 2

```
Met Ala Thr Arg Val Glu Glu Ala Ala Arg Gly Arg Gly Gly Gly Ala
  1               5                  10                  15

Glu Glu Ala Thr Glu Ala Gly Arg Gly Gly Arg Arg Ser Pro Arg
             20                  25                  30

Gln Lys Phe Glu Ile Gly Thr Met Glu Glu Ala Gly Ile Cys Gly Leu
         35                  40                  45

Gly Val Lys Ala Asp Met Leu Cys Asn Ser Gln Ser Asn Asp Ile Leu
     50                  55                  60

Gln His Gln Gly Ser Asn Cys Gly Gly Thr Ser Asn Lys His Ser Leu
 65                  70                  75                  80

Glu Glu Asp Glu Gly Ser Asp Phe Ile Thr Glu Asn Arg Asn Leu Val
                 85                  90                  95

Ser Pro Ala Tyr Cys Thr Gln Glu Ser Arg Glu Glu Ile Pro Gly Gly
            100                 105                 110

Glu Ala Arg Thr Asp Pro Pro Asp Gly Gln Gln Asp Ser Glu Cys Asn
        115                 120                 125

Arg Asn Lys Glu Lys Thr Leu Gly Lys Glu Val Leu Leu Leu Met Gln
    130                 135                 140
```

```
Ala Leu Asn Thr Leu Ser Thr Pro Glu Glu Lys Leu Ala Leu Cys
145                 150                 155                 160

Lys Lys Tyr Ala Asp Leu Leu Glu Glu Ser Arg Ser Val Gln Lys Gln
                165                 170                 175

Met Lys Ile Leu Gln Lys Lys Gln Ala Gln Ile Val Lys Glu Lys Val
            180                 185                 190

His Leu Gln Ser Glu His Ser Lys Ala Ile Leu Ala Arg Ser Lys Leu
        195                 200                 205

Glu Ser Leu Cys Arg Glu Leu Gln Arg His Asn Lys Thr Leu Lys Glu
210                 215                 220

Glu Asn Met Gln Gln Ala Arg Glu Glu Glu Arg Arg Lys Glu Ala
225                 230                 235                 240

Thr Ala His Phe Gln Ile Thr Leu Asp Glu Ile Gln Ala Gln Leu Glu
                245                 250                 255

Gln His Asp Ile His Asn Ala Lys Leu Arg Gln Glu Asn Ile Glu Leu
            260                 265                 270

Gly Glu Lys Leu Lys Lys Leu Ile Glu Gln Tyr Ala Leu Arg Glu Glu
        275                 280                 285

His Ile Asp Lys Val Phe Lys Arg Lys Glu Leu Gln Gln Gln Leu Val
    290                 295                 300

Asp Ala Lys Leu Gln Gln Thr Thr Gln Leu Ile Lys Glu Ala Asp Glu
305                 310                 315                 320

Lys His Gln Arg Glu Arg Glu Phe Leu Leu Lys Glu Ala Thr Glu Ser
                325                 330                 335

Arg His Lys Tyr Glu Gln Met Lys Gln Gln Glu Val Gln Leu Lys Gln
            340                 345                 350

Gln Leu Ser Leu Tyr Met Asp Lys Phe Glu Glu Phe Gln Thr Thr Met
        355                 360                 365

Ala Lys Ser Asn Glu Leu Phe Thr Thr Phe Arg Gln Glu Met Glu Lys
    370                 375                 380

Met Thr Lys Lys Ile Lys Lys Leu Glu Lys Glu Thr Ile Ile Trp Arg
385                 390                 395                 400

Thr Lys Trp Glu Asn Asn Asn Lys Ala Leu Leu Gln Met Ala Glu Glu
                405                 410                 415

Lys Thr Val Arg Asp Lys Glu Tyr Lys Ala Leu Gln Ile Lys Leu Glu
            420                 425                 430

Arg Leu Glu Lys Leu Cys Arg Ala Leu Gln Thr Glu Arg Asn Glu Leu
        435                 440                 445

Asn Glu Lys Val Glu Val Leu Lys Glu Gln Val Ser Ile Lys Ala Ala
    450                 455                 460

Ile Lys Ala Ala Asn Arg Asp Leu Ala Thr Pro Val Met Gln Pro Cys
465                 470                 475                 480

Thr Ala Leu Asp Ser His Lys Glu Leu Asn Thr Ser Ser Lys Arg Ala
                485                 490                 495

Leu Gly Ala His Leu Glu Ala Glu Pro Lys Ser Gln Arg Ser Ala Val
            500                 505                 510

Gln Lys Pro Pro Ser Thr Gly Ser Ala Pro Ala Ile Glu Ser Val Asp
        515                 520                 525

<210> SEQ ID NO 3
<211> LENGTH: 3810
<212> TYPE: DNA
<213> ORGANISM: Mus musculus
```

<400> SEQUENCE: 3

```
tggcccctga gaggttccgt gcccctggtc cagccgcttg tttggctgct gccgtcacct      60
catggcgact cggcttgagg aggtaacgcg aggaagaggc ggcggtactg aggaggctag     120
tgagggcgga cggggcggac ggcgacgtag ccccccgcag aagtttgaaa ttggcacaat     180
ggaagaagct agaatttgtg ggttaggagt aaaagcagac atggtatgta actctcaagc     240
aaatgatatt cttcaacatc aagacccag ttgtggtggc acgactaaga aacattcact      300
ggaaggggat gaaggcagtg actttattac aaagaacaga aatttggtga gctcagtatt     360
ctgtacacag gagaaaagag aagaaattcc tggacgagaa gctcgaacag gtcctcctga     420
tggccagcaa gattcagagt gcagcaggaa caaagagaag accttaggaa aagaagtttt     480
attactgatg caagcgctaa acaccctttc aaccccagag gagaagctgg cagctctctg     540
taagaaatat gctgatctcc tggaagaaag caggaatgtt cagaaacaaa tgaagattct     600
gcagaagaag caagcccaga ttgtgaaaga gaaagttcac cttcagagtg aacacagcaa     660
ggccatcttg gcaagaagca aactggaatc tctttgcagg gaacttcagc gtcataataa     720
gaccttaaag gaggagaata tgcagcaggc acgagaggag gaagaacgac gtaaagaagc     780
aacagcacat ttccagataa ctctaaatga aatccaagct cagttggaac aacatgacat     840
ccacaatgcc aaactgcgac aggagaacat tgaactggga gagaagttga agaagcttat     900
tgagcagtat gcactaaggg aagagcatat tgataaagta ttcaaacaca aggaattgca     960
acaacagctt gtggatgcca aacttcagca aacaacacag ctgataaaag aagctgatga    1020
aaaacatcag agagagagag agttttatt aaaagaagca acagaatcca ggcacaaata    1080
tgaacaaatg aaacagcaag aagtacaact aaaacagcag cttctctctt atatggataa    1140
atttgaagaa ttccagacta ctatggcaaa aagcaatgaa cttttttacaa ccttcaggca    1200
ggaaatggaa aagatgacaa agaaaattaa aaaactggaa aaagaaacaa taatatggcg    1260
taccaaatgg gaaaacaata taaagcact tctgcagatg gccgaagaga aaactgtccg    1320
tgataaagag tacaaggctt ttcaaataaa actggaacgg ttagagaagc tgtgcagggc    1380
tcttcagaca gagagaaatg agctcaacga gaaggtcgaa gtcctgaaag agcaggtctc    1440
tatcaaagca gcagatgggg acttggtgtc acctgcaacg cagccctgtg ctgtcctgga    1500
ttccttcaaa gagacttcaa gaagaaccct gggaatgcac ttggaggcta gagccaagtc    1560
agtgtgtgag aaaagtgctg cacaaaagcc ctcatcttca ggttctcctg ctcaaggcat    1620
tgagtcagtt gactagggtg aagtatgatc actgtattga gagatatatt ttgtgtataa    1680
cttcctctgt tagtagtaac tattggtttt gtggtgaaga ttttcttact tttttctacca    1740
tatctgtatt ttcttagaac tactggactt atgtggtaca ggaggctgct tagcagtttg    1800
gaatagtttt actctataaa tttccctcaa ctatgttgca catctgcctc attttccccc    1860
tttggagtgc atgccttcag cacataattt tcataactaa aaaacaaggc cattagagga    1920
attatattct cccgatggtt ccttgatgtg aaaacaatat cccactaata ttagtgaaag    1980
gaaaatacct ttaataaccc atttaaatac gggattagaa ttcgggaact ggtcagaaac    2040
attttttcatt tgaatcagct tttcttgatt cacttgacaa agtaaaataa ccttgaagtt    2100
ctgacaaaac taacttagta ctcataaagt agtcctaata tattgatttg aggatagatg    2160
acataaaaag gtgattattc cttgaaaagt gcttttttgc agtttccagc aaaaacataa    2220
aagctccctt cctccaccata cattctggct ttgttgaagt tttgtgttca tttgcattaa    2280
gactcaacaa gcagggctgt acatgtgtgt agctcagtgg caagcatttg cctatcataa    2340
```

```
gaggctctgg gttgacaagt tcatcagca aagaacacta gttatttgt ttcctaatag      2400 agaatttaaa ttatagatca gataacataa gataacattt ccaaagtaaa aacactggaa      2460
ccagcttggg aaaacttggc agattgttta catagtcaaa aagacgccta gctttctagt      2520
ctatttctcc gttttttgat gctatcactt taaaacaata aaaaccagta ttaatgtttg      2580
acactttgat atttatggct cagccatgca aattactagg tctttggtaa agtaaattta      2640
ttaaaggttc tagtaaagca ccatattcag agactgactt gttcaattgg ctaaaaattt      2700
catttatact ccttagcaca ttttattttt atggtcaaat ctaggttcaa ataattgaaa      2760
aaatggccaa agccagaaa acagtccctg tagatggtta ttttctaaa ctaatcaagg       2820 ggtcaaaagt aaaagaagtg aaaaagtga agtcagaaac aacaaaaaaa cccttttcagt     2880 agcctcttat caaatactgg actttttccc catgaacgtg tcagaaatat tgaaattact      2940
actaatgatt acatttcaca agtctgctgg atacacagct cttaacattt gattaagcca      3000
tgtgtgtagc ctgccacatt tttgtggtac ttgtcctgtg tggaatattg catattttca      3060
agggctttat aaagcaatgc gattaacagt cctggcctgc tgctttcggc ttacatgcat      3120
tttcagctag atctttagag gacagagatt ctgtatgaaa tatgcatatg caaaatctct      3180
cctcctgtga tgaaaacag atgggacctc aaagaaggat gccctccctc cctcccttaa      3240
agtgatcacc tcagcagccc agtgttgtgg ctttgtagca cgccctgtac taccgtattc      3300
tagaacactg taatgctact gtgctggccc agaaaagatt tctatgttga attcacttac      3360
tgcatatggt gcactaccat gcaatcttga tgtatatttt tagtgtcagt agaccccaaa      3420
atgtagcgaa acttgggtat caggccattt catcctcaga cttgtagaag tacattttct      3480
ggtcttgaga cctgtatttt ttagttatgt atgcaactgc ctttattaca cacctggtta      3540
tcacaattca actctcaggt gttgcagaaa aaaaaaatct acctctttca gactgtagat      3600
ggaaataact gtgaaaaaat gatgcagata tagtttgtgc taaacacact gctttatttt      3660
tacagcccac gtctttcatg aggatatgaa ttgttaagag gcagtcttgt tttgcttttc      3720
aaagacattt tgtagagatt tttcactacc gtaaatctga ttttatctac tcaattctgt      3780
agagattaag taaatatgta tgatgaaatt                                       3810
```

<210> SEQ ID NO 4
<211> LENGTH: 524
<212> TYPE: PRT
<213> ORGANISM: Homo sapiens

<400> SEQUENCE: 4

```
Met Ala Thr Arg Leu Glu Glu Val Thr Arg Gly Arg Gly Gly Thr
 1               5                  10                  15

Glu Glu Ala Ser Glu Gly Gly Arg Gly Gly Arg Arg Ser Pro Pro
                20                  25                  30

Gln Lys Phe Glu Ile Gly Thr Met Glu Glu Ala Arg Ile Cys Gly Leu
            35                  40                  45

Gly Val Lys Ala Asp Met Val Cys Asn Ser Gln Ala Asn Asp Ile Leu
        50                  55                  60

Gln His Gln Asp Pro Ser Cys Gly Gly Thr Lys Lys His Ser Leu
65                  70                  75                  80

Glu Gly Asp Glu Gly Ser Asp Phe Ile Thr Lys Asn Arg Asn Leu Val
                85                  90                  95

Ser Ser Val Phe Cys Thr Gln Glu Lys Arg Glu Glu Ile Pro Gly Arg
            100                 105                 110
```

```
Glu Ala Arg Thr Gly Pro Pro Asp Gly Gln Gln Asp Ser Glu Cys Ser
        115                 120                 125

Arg Asn Lys Glu Lys Thr Leu Gly Lys Glu Val Leu Leu Leu Met Gln
        130                 135                 140

Ala Leu Asn Thr Leu Ser Thr Pro Glu Glu Lys Leu Ala Ala Leu Cys
145                 150                 155                 160

Lys Lys Tyr Ala Asp Leu Leu Glu Glu Ser Arg Asn Val Gln Lys Gln
                165                 170                 175

Met Lys Ile Leu Gln Lys Lys Gln Ala Gln Ile Val Lys Glu Lys Val
                180                 185                 190

His Leu Gln Ser Glu His Ser Lys Ala Ile Leu Ala Arg Ser Lys Leu
                195                 200                 205

Glu Ser Leu Cys Arg Glu Leu Gln Arg His Asn Lys Thr Leu Lys Glu
        210                 215                 220

Glu Asn Met Gln Gln Ala Arg Glu Glu Glu Arg Arg Lys Glu Ala
225                 230                 235                 240

Thr Ala His Phe Gln Ile Thr Leu Asn Glu Ile Gln Ala Gln Leu Glu
                245                 250                 255

Gln His Asp Ile His Asn Ala Lys Leu Arg Gln Glu Asn Ile Glu Leu
                260                 265                 270

Gly Glu Lys Leu Lys Lys Leu Ile Glu Gln Tyr Ala Leu Arg Glu Glu
        275                 280                 285

His Ile Asp Lys Val Phe Lys His Lys Glu Leu Gln Gln Gln Leu Val
        290                 295                 300

Asp Ala Lys Leu Gln Gln Thr Thr Gln Leu Ile Lys Glu Ala Asp Glu
305                 310                 315                 320

Lys His Gln Arg Glu Arg Glu Phe Leu Leu Lys Glu Ala Thr Glu Ser
                325                 330                 335

Arg His Lys Tyr Glu Gln Met Lys Gln Gln Glu Val Gln Leu Lys Gln
                340                 345                 350

Gln Leu Ser Leu Tyr Met Asp Lys Phe Glu Glu Phe Gln Thr Thr Met
        355                 360                 365

Ala Lys Ser Asn Glu Leu Phe Thr Thr Phe Arg Gln Glu Met Glu Lys
        370                 375                 380

Met Thr Lys Lys Ile Lys Lys Leu Glu Lys Glu Thr Ile Ile Trp Arg
385                 390                 395                 400

Thr Lys Trp Glu Asn Asn Asn Lys Ala Leu Leu Gln Met Ala Glu Glu
                405                 410                 415

Lys Thr Val Arg Asp Lys Glu Tyr Lys Ala Phe Gln Ile Lys Leu Glu
                420                 425                 430

Arg Leu Glu Lys Leu Cys Arg Ala Leu Gln Thr Glu Arg Asn Glu Leu
        435                 440                 445

Asn Glu Lys Val Glu Val Leu Lys Glu Gln Val Ser Ile Lys Ala Ala
        450                 455                 460

Asp Gly Asp Leu Val Ser Pro Ala Thr Gln Pro Cys Ala Val Leu Asp
465                 470                 475                 480

Ser Phe Lys Glu Thr Ser Arg Arg Thr Leu Gly Met His Leu Glu Ala
                485                 490                 495

Arg Ala Lys Ser Val Cys Glu Lys Ser Ala Ala Gln Lys Pro Ser Ser
                500                 505                 510

Ser Gly Ser Pro Ala Gln Gly Ile Glu Ser Val Asp
        515                 520
```

```
<210> SEQ ID NO 5
<211> LENGTH: 1429
<212> TYPE: DNA
<213> ORGANISM: Homo sapiens

<400> SEQUENCE: 5
gtctgcgcgt gtgcgttttc cctcctcccc gccctcaggg tccacggcca ccatggcgta      60
ttaggggcag cagtgcctgc ggcagcattg gcctttgcag cggcggcagc agcaccaggc     120
tctgcagcgg caaccccag cggcttaagc catggcgctt ctcacggcat tcagcagcag     180
cgttgctgta accgacaaag acaccttcga attaagcaca ttcctcgatt ccagcaaagc     240
accgcaacat gaccgaaatg agcttcctga gcagcgaggt gttggtgggg gacttgatgt     300
cccccttcga ccagtcgggt ttggggctg aagaaagcct aggtctctta gatgattacc     360
tggaggtggc caagcacttc aaacctcatg ggttctccag cgacaaggct aaggcgggct     420
cctccgaatg gctggctgtg gatgggttgg tcagtccctc caacaacagc aaggaggatg     480
ccttctccgg gacagattgg atgttggaga aaatggattt gaaggagttc gacttggatg     540
ccctgttggg tatagatgac ctggaaacca tgccagatga ccttctgacc acgttggatg     600
acacttgtga tctctttgcc ccctagtcc aggagactaa taagcagccc cccagacgg      660
tgaacccaat tggccatctc ccagaaagtt aacaaaacc cgaccaggtt gcccccttca     720
ccttcttaca acctcttccc cttcccag gggtcctgtc ctccactcca gatcattcct     780
ttagtttaga gctgggcagt gaagtggata tcactgaagg agataggaag ccagactaca     840
ctgcttacgt tgccatgatc cctcagtgca taaggagga agacacccct tcagataatg     900
atagtggcat ctgtatgagc ccagagtcct atctggggtc tcctcagcac agcccctcta     960
ccagggctc tccaaatagg agcctcccat ctccaggtgt tctctgtggg tctgcccgtc    1020
ccaaaccta cgatcctcct ggagagaaga tggtagcagc aaaagtaaag ggtgagaaac    1080
tggataagaa gctgaaaaaa atggagcaaa acaagacagc agccactagg taccgccaga    1140
agaagagggc ggagcaggag gctcttactg tgagtgcaa agagctggaa agaagaacg     1200
aggctctaaa agagagggcg gattccctgg ccaaggagat ccagtacctg aaagatttga    1260
tagaagaggt ccgcaaggca agggggaaga aaaagggtccc ctagttgagg atagtcagga    1320
gcgtcaatgt gcttgtacat agagtgctgt agctgtgtgt tccaataaat tattttgtag    1380
ggaaaaaaaa aaaaaaaaaa aaaaaaaaaa aaaaaaaaaa aaaaaaaa                 1429

<210> SEQ ID NO 6
<211> LENGTH: 351
<212> TYPE: PRT
<213> ORGANISM: Homo sapiens

<400> SEQUENCE: 6

Met Thr Glu Met Ser Phe Leu Ser Glu Val Leu Val Gly Asp Leu
1               5                   10                  15

Met Ser Pro Phe Asp Gln Ser Gly Leu Gly Ala Glu Glu Ser Leu Gly
            20                  25                  30

Leu Leu Asp Asp Tyr Leu Glu Val Ala Lys His Phe Lys Pro His Gly
        35                  40                  45

Phe Ser Ser Asp Lys Ala Lys Ala Gly Ser Ser Glu Trp Leu Ala Val
    50                  55                  60

Asp Gly Leu Val Ser Pro Ser Asn Asn Ser Lys Glu Asp Ala Phe Ser
65                  70                  75                  80
```

Gly Thr Asp Trp Met Leu Glu Lys Met Asp Leu Lys Glu Phe Asp Leu
                85                  90                  95

Asp Ala Leu Leu Gly Ile Asp Asp Leu Glu Thr Met Pro Asp Asp Leu
                100                 105                 110

Leu Thr Thr Leu Asp Asp Thr Cys Asp Leu Phe Ala Pro Leu Val Gln
                115                 120                 125

Glu Thr Asn Lys Gln Pro Pro Gln Thr Val Asn Pro Ile Gly His Leu
            130                 135                 140

Pro Glu Ser Leu Thr Lys Pro Asp Gln Val Ala Pro Phe Thr Phe Leu
145                 150                 155                 160

Gln Pro Leu Pro Leu Ser Pro Gly Val Leu Ser Ser Thr Pro Asp His
                165                 170                 175

Ser Phe Ser Leu Glu Leu Gly Ser Glu Val Asp Ile Thr Glu Gly Asp
                180                 185                 190

Arg Lys Pro Asp Tyr Thr Ala Tyr Val Ala Met Ile Pro Gln Cys Ile
                195                 200                 205

Lys Glu Glu Asp Thr Pro Ser Asp Asn Asp Ser Gly Ile Cys Met Ser
            210                 215                 220

Pro Glu Ser Tyr Leu Gly Ser Pro Gln His Ser Pro Ser Thr Arg Gly
225                 230                 235                 240

Ser Pro Asn Arg Ser Leu Pro Ser Pro Gly Val Leu Cys Gly Ser Ala
                245                 250                 255

Arg Pro Lys Pro Tyr Asp Pro Pro Gly Glu Lys Met Val Ala Ala Lys
                260                 265                 270

Val Lys Gly Glu Lys Leu Asp Lys Lys Leu Lys Lys Met Glu Gln Asn
                275                 280                 285

Lys Thr Ala Ala Thr Arg Tyr Arg Gln Lys Lys Arg Ala Glu Gln Glu
            290                 295                 300

Ala Leu Thr Gly Glu Cys Lys Glu Leu Glu Lys Lys Asn Glu Ala Leu
305                 310                 315                 320

Lys Glu Arg Ala Asp Ser Leu Ala Lys Glu Ile Gln Tyr Leu Lys Asp
                325                 330                 335

Leu Ile Glu Glu Val Arg Lys Ala Arg Gly Lys Lys Arg Val Pro
                340                 345                 350

<210> SEQ ID NO 7
<211> LENGTH: 1391
<212> TYPE: DNA
<213> ORGANISM: Mus musculus

<400> SEQUENCE: 7
gccggtttga gttgtgcgct cgggtgtccc tttcctcttc ccctcccgca gggcttgcgg      60
ccaccatggc gtattagagg cagcagtgcc tgcggcagcg ttggcctttg cagcggcggc     120
agcagcacca ggctctgcag cggcaacccc caccggccta agccatggcg ctcttcacga     180
aatccagcag cagtgttgct gtaacggaca agatacctt cgagttaagc acattcctgg     240
aatccagcaa agccccacaa catgaccgag atgagcttcc tgaacagcga agtgttggcg     300
ggggacttga tgtcccccctt cgaccagtcg ggtttggggg ctgaagaaag cctaggtctc     360
ttagatgact atctggaggt ggccaagcac ttgaaacctc atgggttctc cagcgacaag     420
gcgggctcct cggaatggcc ggctatggat gatggcttgg ccagtgcctc agacaccggc     480
aaggaggatg ccttttccgg gacagattgg atgttggaga aaatggatct gaaagagttt     540
gacttcgatg ctctgtttcg aatggatgac ctggaaacca tgccagatga gctcttgacc     600

-continued

```
acgttggatg acacatgtga tcttttttgcc cctctagtcc aagagactaa taaggagccc    660
cctcagacag tgaacccaat tggccatctc ccagaaagtt taataaaagt cgaccaggtt    720 gccccctttta cattcttgca gccttttcccc tgttccccag gggttctgtc ttccactcca   780
gagcattcct ttagtttaga gctaggcagt gaagttgata tctctgaagg agacaggaag    840
cctgactctg ctgcttacat tactctaatc cctccatgtg taaaggagga agacactccc    900
tctgacaatg acagtggcat ctgtatgagc ccggagtcct acctgggctc tccccagcat    960 agccccctcca cctccagggc cccaccagac aatctgcctt ctccaggtgg ttcccgtggg   1020
tctcctcggc ccaaaccttta tgacccacct ggagttagtt tgacagctaa agtgaagact   1080
gagaaattgg ataagaagct gaaaaagatg gagcaaaaca agacagcagc cactaggtac    1140
cgccagaaga agcgggctga gcaggaggcc ctcactggcg agtgtaagga gctagaaaaa    1200
aagaatgagg ctctgaaaga gaaggcagat tctctggcca aggagatcca gtatctgaaa    1260
gacctgatag aagaggtccg taaggcaagg gggaagaaga gagttccgta ataggggtagt   1320 caggtgctttt gtgcttgtac atagtcttgt gttgctgtgt ttgctgtaat aaattattttt   1380 gtagtgaaag t                                                          1391
```

<210> SEQ ID NO 8
<211> LENGTH: 346
<212> TYPE: PRT
<213> ORGANISM: Mus musculus

<400> SEQUENCE: 8

```
Met Ser Phe Leu Asn Ser Glu Val Leu Ala Gly Asp Leu Met Ser Pro
  1               5                  10                  15

Phe Asp Gln Ser Gly Leu Gly Ala Glu Glu Ser Leu Gly Leu Leu Asp
             20                  25                  30

Asp Tyr Leu Glu Val Ala Lys His Leu Lys Pro His Gly Phe Ser Ser
         35                  40                  45

Asp Lys Ala Gly Ser Ser Glu Trp Pro Ala Met Asp Asp Gly Leu Ala
     50                  55                  60

Ser Ala Ser Asp Thr Gly Lys Glu Asp Ala Phe Ser Gly Thr Asp Trp
 65                  70                  75                  80

Met Leu Glu Lys Met Asp Leu Lys Glu Phe Asp Phe Asp Ala Leu Phe
                 85                  90                  95

Arg Met Asp Asp Leu Glu Thr Met Pro Asp Glu Leu Leu Thr Thr Leu
            100                 105                 110

Asp Asp Thr Cys Asp Leu Phe Ala Pro Leu Val Gln Glu Thr Asn Lys
        115                 120                 125

Glu Pro Pro Gln Thr Val Asn Pro Ile Gly His Leu Pro Glu Ser Leu
    130                 135                 140

Ile Lys Val Asp Gln Val Ala Pro Phe Thr Phe Leu Gln Pro Phe Pro
145                 150                 155                 160

Cys Ser Pro Gly Val Leu Ser Ser Thr Pro Glu His Ser Phe Ser Leu
                165                 170                 175

Glu Leu Gly Ser Glu Val Asp Ile Ser Glu Gly Asp Arg Lys Pro Asp
            180                 185                 190

Ser Ala Ala Tyr Ile Thr Leu Ile Pro Pro Cys Val Lys Glu Glu Asp
        195                 200                 205

Thr Pro Ser Asp Asn Asp Ser Gly Ile Cys Met Ser Pro Glu Ser Tyr
    210                 215                 220

Leu Gly Ser Pro Gln His Ser Pro Ser Thr Ser Arg Ala Pro Pro Asp
```

```
                     225                 230                 235                 240

Asn Leu Pro Ser Pro Gly Gly Ser Arg Gly Ser Pro Arg Pro Lys Pro
                245                 250                 255

Tyr Asp Pro Pro Gly Val Ser Leu Thr Ala Lys Val Lys Thr Glu Lys
            260                 265                 270

Leu Asp Lys Lys Leu Lys Lys Met Glu Gln Asn Lys Thr Ala Ala Thr
        275                 280                 285

Arg Tyr Arg Gln Lys Lys Arg Ala Glu Gln Glu Ala Leu Thr Gly Glu
    290                 295                 300

Cys Lys Glu Leu Glu Lys Lys Asn Glu Ala Leu Lys Glu Lys Ala Asp
305                 310                 315                 320

Ser Leu Ala Lys Glu Ile Gln Tyr Leu Lys Asp Leu Ile Glu Glu Val
                325                 330                 335

Arg Lys Ala Arg Gly Lys Lys Arg Val Pro
            340                 345
```

<210> SEQ ID NO 9
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 9
cctgctcctc ctgcttacat cagaga                                          26

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
atccatcaaa gcgccatcaa agcg                                            24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
acaaataaag caatagcatc acaa                                            24

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
caccatggag aaggccggg                                                  19

<210> SEQ ID NO 13
<211> LENGTH: 20
<212> TYPE: DNA
<213> ORGANISM: Artificial Sequence
<220> FEATURE:
<223> OTHER INFORMATION: Primer

```
<400> SEQUENCE: 13
gacggacaca ttgggggtag                                            20

<210> SEQ ID NO 14
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 14
gaacgacgua aagaagcaau u                                          21

<210> SEQ ID NO 15
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 15
uugcuucuuu acgucguucu u                                          21

<210> SEQ ID NO 16
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 16
cuguccguga uaaagaguau u                                          21

<210> SEQ ID NO 17
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 17
uacucuuuau cacggacagu u                                          21

<210> SEQ ID NO 18
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 18
cuucagcguc auaauaagau u                                          21

<210> SEQ ID NO 19
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 19
ucuuauuaug acgcugaagu u                                          21

<210> SEQ ID NO 20
<211> LENGTH: 55
```

<212> TYPE: DNA
<213> ORGANISM: Artificial Sequence
<220> FEATURE:
<223> OTHER INFORMATION: Synthetically generated oligonucleotide

<400> SEQUENCE: 20
gatccgaacg acgtaaagaa gcaattcaag agattgcttc tttacgtcgt tctta    55

<210> SEQ ID NO 21
<211> LENGTH: 55
<212> TYPE: DNA
<213> ORGANISM: Artificial Sequence
<220> FEATURE:
<223> OTHER INFORMATION: Synthetically generated oligonucleotide

<400> SEQUENCE: 21
agcttaagaa cgacgtaaag aagcaatctc ttgaattgct tctttacgtc gttcg    55

<210> SEQ ID NO 22
<211> LENGTH: 55
<212> TYPE: DNA
<213> ORGANISM: Artificial Sequence
<220> FEATURE:
<223> OTHER INFORMATION: Synthetically generated oligonucleotide

<400> SEQUENCE: 22
gatccctgtc cgtgataaag agtattcaag agatactctt tatcacggac agtta    55

<210> SEQ ID NO 23
<211> LENGTH: 55
<212> TYPE: DNA
<213> ORGANISM: Artificial Sequence
<220> FEATURE:
<223> OTHER INFORMATION: Synthetically generated oligonucleotide

<400> SEQUENCE: 23
agcttaactg tccgtgataa agagtatctc ttgaatactc tttatcacgg acagg    55

<210> SEQ ID NO 24
<211> LENGTH: 55
<212> TYPE: DNA
<213> ORGANISM: Artificial Sequence
<220> FEATURE:
<223> OTHER INFORMATION: Synthetically generated oligonucleotide

<400> SEQUENCE: 24
gatcccttca gcgtcataat aagattcaag agatcttatt atgacgctga agtta    55

<210> SEQ ID NO 25
<211> LENGTH: 55
<212> TYPE: DNA
<213> ORGANISM: Artificial Sequence
<220> FEATURE:
<223> OTHER INFORMATION: Synthetically generated oligonucleotide

<400> SEQUENCE: 25
agcttaactt cagcgtcata ataagatctc ttgaatctta ttatgacgct gaagg    55

<210> SEQ ID NO 26
<211> LENGTH: 1521
<212> TYPE: DNA
<213> ORGANISM: Homo sapiens

<400> SEQUENCE: 26
atggcgacgc gggtagagga ggcggcgcgg ggaagaggcg gcggcgccga agaggcgact    60

```
gaggccggac ggggcggacg gcgacgcagc ccgcggcaga agtttgaaat tggcacaatg    120
gaagaagctg gaatttgtgg gctaggggcg aaagcagata tgttgtgtaa ctctcaatca    180
aatgatattc ttcaacatca aggctcaaat tgtggtggca caagtaacaa gcattcattg    240
gaagaggatg aaggcagtga ctttataaca gagaacagga atttggtgag cccagcatac    300
tgcacgcaag aatcaagaga ggaaatccct gggggagaag ctcgaacaga tcccctgat     360 ggtcagcaag attcagagtg caacaggaac aaagaaaaaa ctgcagctct ctgtaagaaa    420
tatgctgatc ttctggagga gagcaggagt gttcagaagc aaatgaagat cctgcagaag    480
aagcaagccc agattgtgaa agagaaagtt cacttgcaga gtgaacatag caaggctatc    540
ttggcaagaa gcaagctaga atctctttgc agagaacttc agcgtcacaa taagacgtta    600
aaggaggaaa atatgcagca ggcacgagag gaagaagaac gacgtaaaga agcaactgca    660
catttccaga ttaccttaga tgaaattcaa gcccagctgg agcagcatga catccacaac    720
gccaaactcc gacaggaaaa cattgagctg ggggagaagc taaagaagct catcgaacag    780
tacgcactga gggaagagca cattgataag gtgttcaaac gtaaggaact gcaacagcag    840
ctcgtggatg ccaaactgca gcaaacgaca caactgataa agaagctga tgaaaaacat     900 cagagagaga gagagttttt attaaaagaa gcgacagaat cgaggcacaa atacgaacaa    960
atgaaacagc aggaagtaca actaaaacag cagctttctc tttatatgga taagtttgaa   1020
gaattccaga ctaccatggc aaaaagcaat gaactgttta caaccttcag acaggaaatg   1080
gaaaagatga caaagaaaat taaaaaactg gaaaagaaa caataatttg gcgtaccaaa    1140
tgggaaaaca ataataaagc acttctgcaa atggctgaag agaaaacagt ccgtgataaa   1200
gagtacaagg cccttcaaat aaaactggaa cggttagaga agctgtgcag ggctcttcaa   1260
acagaaagga atgagctcaa tgagaaggtg gaagtcctga aagagcaggt atccatcaaa   1320
gcggccatca aagcggcgaa cagggattta gcaacacctg tgatgcagcc ctgtactgcc   1380
ctggattctc acaaggagct gaacacttcc tcgaaaagag ccctgggagc gcacctggag   1440
gctgagccca agagtcagag aagcgctgtg caaaagcccc cgtccacagg ctctgctccg   1500
gccatcgagt cggttgacta a                                             1521

<210> SEQ ID NO 27
<211> LENGTH: 1500
<212> TYPE: DNA
<213> ORGANISM: Homo sapiens

<400> SEQUENCE: 27
atggcgacgc gggtagagga ggcggcgcgg ggaagaggcg gcggcgccga agaggcgact     60
gaggccggac ggggcggacg gcgacgcagc ccgcggcaga agtttgaaat tggcacaatg    120
gaagaagctg gaatttgtgg gctaggggtg aaagcagata tgttgtgtaa ctctcaatca    180
aatgatattc ttcaacatca aggctcaaat tgtggtggca caagtaacaa gcattcattg    240
gaagaggatg aaggcagtga ctttataaca gagaacagga atttggtgag cccagcatac    300
tgcacgcaag aatcaagaga ggaaatccct gggggagaag ctcgaacaga tcccctgat     360 ggtcagcaag attcagagtg caacaggaac aaagaaaaaa cttaggaaa agaagtttta    420 ttactgatgc aagccctaaa cacccttca accccagagg agaagctggc agctctctgt    480
aagaaatatg ctgatcttct ggaggagagc aggagtgttc agaagcaaat gaagatcctg    540
cagaagaagc aagcccagat tgtgaaagag aaagttcaca ggaggaaaa tatgcagcag    600 gcacgagagg aagaagaacg acgtaaagaa gcaactgcac atttccagat taccttagat    660
```

```
gaaattcaag cccagctgga gcagcatgac atccacaacg ccaaactccg acaggaaaac      720
attgagctgg gggagaagct aaagaagctc atcgaacagt acgcactgag ggaagagcac      780
attgataagg tgttcaaacg taaggaactg caacagcagc tcgtggatgc caaactgcag      840
caaacgacac aactgataaa agaagctgat gaaaaacatc agagagagag agagttttta      900
ttaaaagaag cgacagaatc gaggcacaaa tacgaacaaa tgaaacagca ggaagtacaa      960
ctaaaacagc agctttctct ttatatggat aagtttgaag aattccagac taccatggca     1020
aaaagcaatg aactgtttac aaccttcaga caggaaatgg aaaagatgac aaagaaaatt     1080
aaaaaactgg aaaagaaac aataatttgg cgtaccaaat gggaaaacaa taataaagca      1140
cttctgcaaa tggctgaaga gaaaacagtc cgtgataaag agtacaaggc ccttcaaata     1200
aaactggaac ggttagagaa gctgtgcagg gctcttcaaa cagaaaggaa tgagctcaat     1260
gagaaggtgg aagtcctgaa agagcaggta tccatcaaag cggccatcaa agcggcgaac     1320
agggatttag caacacctgt gatgcagccc tgtactgccc tggattctca caaggagctg     1380
aacacttcct cgaaaagagc cctgggagcc cacctggagg ctgagcccaa gagtcagaga     1440
agcgctgtgc aaaagccccc gtccacaggc tctgctccgg ccatcgagtc ggttgactaa     1500
```

<210> SEQ ID NO 28
<211> LENGTH: 1521
<212> TYPE: DNA
<213> ORGANISM: Homo sapiens

<400> SEQUENCE: 28

```
atggcgacgc gggtagagga ggcagcgcgg ggaagaggcg gcggcgccga agaggcgact       60
gaggccggac ggggcggacg gcgacgcagc ccgcggcaga agtttgaaat tggcacaatg      120
gaagaagctg gaatttgtgg gctaggggtg aaagcagata tgttgtgtaa ctctcaatca      180
aatgatattc ttcaacatca aggctcaaat tgtggtggca aagtaacaa gcattcattg       240 gaagaggatg aaggcagtga ctttataaca gagaacagga atttggtgag cccagcatac      300
tgcacgcaag aatcaagaga ggaaatccct gggggagaag ctcgaacaga tcccctgat      360 ggtcagcaag attcagagtg caacaggaac aaagaaaaaa ctttaggaaa agaagtttta     420
ttactgatgc aagcccctaaa caccctttca accccagagg agaagctggc agctctctgt     480
aagaaatatg ctgatcttct ggaggagagc aggagtgttc agaagcaaat gaagatcctg      540
cagaagaagc aagcccagat tgtgaaagag aaagttcact tgcagagtga acatagcaag      600
gctatcttgg caagaagcaa gctagaatct cttttgcagag aacttcagcg tcacaataag      660
acgttaaagg aggaaaatat gcagcaggca cgagaggaag aagaacgacg taaagaagca      720
actgcacatt tccagattac cttagatgaa attcaagccc agctggagca gcatgacatc      780
cacaacgcca aactccgaca ggaaaacatt gagctggggg agaagctaaa gaagctcatc      840
gaacagtacg cactgaggga gagcacatt gataaggtgt tcaaacgtaa ggaactgcaa      900
cagcagctcg tggatgccaa actgcagcaa acgacacaac tgataaaaga agctgatgaa      960
aaacatcaga gagagagag gttttttatta aaagaagcga cagaatcgag gcacaaatac     1020
gaacaaatga acagcaaga agtacaacta aacagcagc tttctcttta tatggataag     1080
tttgaagaat tccagactac catggcaaaa agcaatgaac tgtttacaac cttcagacag     1140 gaaatgggaaa agatgacaaa gaaattaaa aaactggaaa aggaacaat aatttggcgt     1200 accaaatggg aaaacaataa taagcactt ctgcaaatgg ctgaagagaa aacagtccgt     1260
```

```
                                                        -continued
gataaagagt acaaggcoct tcaaataaaa ctggaacgga aagagcaggt atccatcaaa        1320
gcggccatca aagcggcgaa cagggattta gcaacacctg tgatgcagcc ctgtactgcc        1380
ctggattctc acaaggagct gaacacttcc tcgaaaagag tcctgggagc gcacctggag        1440
gctgagccca agagtcagag aagcgctgtg caaaagcccc cgtccacagg ctctgctccg        1500
gccatcgagt cggttgacta a                                                 1521
```